(12) United States Patent
Curtis

(10) Patent No.: US 8,158,769 B2
(45) Date of Patent: Apr. 17, 2012

(54) MEMBERS OF THE CAPSAICIN/VANILLOID RECEPTOR FAMILY OF PROTEINS AND USES THEREOF

(75) Inventor: Rory A. J. Curtis, Southborough, MA (US)

(73) Assignee: Bayer Schering Pharma Aktiengesellschaft, Leverkusen (DE)

( * ) Notice: Subject to any disclaimer, the term of this patent is extended or adjusted under 35 U.S.C. 154(b) by 0 days.

(21) Appl. No.: 12/895,052

(22) Filed: Sep. 30, 2010

(65) Prior Publication Data

US 2011/0033892 A1 Feb. 10, 2011

Related U.S. Application Data

(60) Division of application No. 11/967,558, filed on Dec. 31, 2007, now Pat. No. 7,807,388, which is a continuation of application No. 11/013,090, filed on Dec. 15, 2004, now Pat. No. 7,323,314, which is a division of application No. 09/587,111, filed on Jun. 2, 2000, now Pat. No. 7,063,951, which is a division of application No. 09/439,165, filed on Nov. 12, 1999, now abandoned, which is a continuation-in-part of application No. 09/421,134, filed on Oct. 19, 1999, now abandoned, which is a continuation-in-part of application No. 09/258,633, filed on Feb. 26, 1999, now abandoned.

(60) Provisional application No. 60/114,078, filed on Dec. 28, 1998, provisional application No. 60/108,322, filed on Nov. 13, 1998.

(51) Int. Cl.
*C12N 15/12* (2006.01)
*C07K 14/705* (2006.01)

(52) U.S. Cl. .................. 536/23.5; 435/69.1; 435/252.3; 435/320.1

(58) Field of Classification Search ........................ None
See application file for complete search history.

(56) References Cited

U.S. PATENT DOCUMENTS

| 6,335,180 B1 | 1/2002 | Julius |
| 6,444,440 B1 | 9/2002 | Young |
| 7,063,951 B1 | 6/2006 | Curtis |
| 7,323,314 B2 | 1/2008 | Curtis |

FOREIGN PATENT DOCUMENTS

| EP | 953638 | 11/1998 |
| EP | 943683 | 9/1999 |
| WO | WO9839448 | 9/1998 |
| WO | WO9845436 | 10/1998 |
| WO | WO9909140 | 2/1999 |
| WO | WO9937675 | 7/1999 |
| WO | WO9937765 | 7/1999 |
| WO | WO9946377 | 9/1999 |

OTHER PUBLICATIONS

Caterina et al., The Capsaicin Receptor: A Heat-Activated Ion Channel in the Pain Pathway, (Oct. 23, 1997), NATURE 389:816-824.*
Benham, Christopher D. et al. (2003) "TRPV Channels as Temperature Sensors." Cell Calcium 33:479-487.
Campbell, E., "Clinical Application of Capsaicin and its Analogues" Capsaicin in the Study of Pain, John N. Wood, ed., Academic Press, London, Chapter 12, pp. 255-262 (1993).
Caterina, M. J., et al., "A Capsaicin-receptor Homologue with a High Threshold for Noxious Heat" Nature, vol. 398, pp. 436-441 (1999).
Caterina, M. J., et al., "The Capsaicin Receptor: a Heat-Activated Ion Channel in the Pain Pathway" Nature, vol. 389, pp. 816-824 (1997).
Chien et al. "The Two-Hybrid System: A Method to Identify and Clone Genes for Proteins that Interact with a Protein of Interest." (Nov. 1991) PNAS 88:9578-9582.
Genbank Accession No. AF029310.1 for Rattus Norvegicus Vanilloid Receptor Subtype 1 mRNA (Oct. 8, 1997).
Gunthrope, Martin J. (2002) "The Diversity in the Vanilloid (TRPV) Receptor Family of Ion Channels." TRENDS in Pharmacological Sciences Apr. 23(4):183-191.
James, I. F. et al., "The Capsaicin Receptor," Capsaicin in the Study of Pain, John N. Wood, ed., Academic Press, London, Chapter 5, pp. 83-104 (1993).
Jansco, G. et al., "Pharmacologically Induced Selective Degeneration of Chemosensitive Primary Sensory Neurons" Nature, vol. 270, pp. 741-743 (1977).
Ketchum, K. A. et al., "Isolation of an Ion Channel Gene from *Arabidopsis thaliana* using the H5 signature Sequence from Voltage-Dependent K+ Channels" FEBS Letters vol. 378, pp. 19-26 (1996).
Montell, C. et al., Molecular Characterization of the *Drosophilia* trp Locus: A Putative Integral Membrane Protein Required for Phototransduction,: Neuron, vol. 2, pp. 1313-1323 (1989).
Sattler, N. et al., "Role of the Adapter Protein CRKL in Signal Transduction of Normal Hematopoietic and BCR/ABL-Transformed Cells," Leukemia, vol. 12, pp. 637-644 (1998).
Stenholm, E. et al. (2002) "VR1- and VRl-1-like Immunoreactivity in Normal and Injured Trigeminal Dental Primary Sensory Neurons of the Rat." Acta Odontol Scand. Mar. 60(2):72-79.
Szallasi, A. et al., "Vanilloid Receptors: New Insights Enhance Potential as a Therapeutic Target," Pain, vol. 68, pp. 195-208 (1996).
Szallasi, A. et al., (1996) "Vanilloid Receptors: New Insights Enhance Potential as a Therapeutic Target." Pain 68: 195-208.

(Continued)

Primary Examiner — John Ulm
(74) Attorney, Agent, or Firm — Banner & Witcoff, Ltd.

(57) ABSTRACT

The invention provides isolated nucleic acids molecules, designated hVR-1, hVR-2, and rVR-2 nucleic acid molecules, which encode novel members of the Capsaicin/Vanilloid receptor family. The invention also provides antisense nucleic acid molecules, recombinant expression vectors containing hVR-1, hVR-2, and rVR-2 nucleic acid molecules, host cells into which the expression vectors have been introduced, and nonhuman transgenic animals in which an hVR-1, hVR-2, and rVR-2 gene has been introduced or disrupted. The invention still further provides isolated hVR-1, hVR-2, and rVR-2 proteins, fusion proteins, antigenic peptides and anti-hVR-1, anti-hVR-2, and anti-rVR-2 antibodies. Diagnostic methods utilizing compositions of the invention are also provided.

11 Claims, 37 Drawing Sheets

OTHER PUBLICATIONS

Szolcsanyi, J., "Actions of Capsaicin on Sensory Receptors," Capsaicin in the Study of Pain, John N. Wood, ed., Academic Press, London, Chapter 1, pp. 1-26 (1993).

Zagotta, W. N. et al., "Structure and Function of Cyclic Nucleotide-Gated Channels," Annu. Rev. Neurosci., vol. 19, pp. 235-263 (1996).

* cited by examiner humanVR1 gene with translation of open reading frame

Input file Fchrb87a6.seq; Output File Fchrb87a6.tra
Sequence length 3909

GTGAGCGCAACGCACTGCGGGCAGTGAGCGCAACGCACTGCGGGCAGTGAGCGCAACGCACTGCGGGCAGTGAGCGCAA

CGCACTGCGGGCAGTGAGCGCAACGCACTGCGGGCAGTGAGCGCAACGCACTGCGGGCAGTGAGCGCAACGCACTGCGG

GCAGTGAGCGCAACGCACTTGCGGGCAGTGAGCGCAACGCACTGCGGGCAGTGAGCGCAACGCACTGCGGGCAGTGAGC

GCAACGCACTGCGGGCAGTGAGCGCAACGCACTGCGGGCAGTGAGCGCAACGCACTGCGGGCAGTGAGCGCAACGCACT

GCGGGCAGTGAGCGCAACGCACTGCGGGCAGTGAGCGCAACGCACTGCGGGCAGTGAGCGCAACGCACTGCGGGCAGTG

AGCGCAACGCACTGCGGGCAGTGAGCGCAACGCACTTAATGTGAGTTAGCTCACTCATTAGGCACCCCAGGCTTTACAC

TTTATGCTTCCGGCTCGTATGTTGTGTGGAATTGTGAGCGGATAACAATTTCACACAGGAAACAGCTATGACCATGATT

ACGCCAAGCTCTAATACGACTCACTATAGGGAAAGCTGGTACGCCTGCAGGTACCGGTCCGGAATTCCCGGGTCGACCC

ACGCGTCCGAAAACACACCTCTCTGCTGTGGGAAGACTGTGCAATGGCACAGCCGCAGAGCTTGGTTTGGGAGGTTGAA

GTGCTCTGGGGAGAATTCGTAGATCATCCTCAGAAAAGCCTTGCCCTGGTGTTCTACCAGAAAAACGTCTCCCAATCAC

CCAGAAAAGCTGTCCACAGTAGTCCCCCCTTATCCACGGGTGTCACTTTCCATGGGTTCAGTTATTTGCGGTCAACCAC

GGTCTGCCAATATTAAATGGAAAATTCTTCAAACAGTTCCCAAGTTTTCCCTTGTGCATTGTTCTGAGCAGTGTGATGA

AGAGTCTCTGCCGTGCCATCTGGGATGCAAACCGTCCCTGTGTCCCCCACGTCCAGGCCGTAGATGCTCCCCGCCGGTC

AGTCACTTAGTCGTCAGATCGCCCGTCCTGGTATCACAGTGCTTCTGTTCAGGTTGCACACTGGGCCACAGAGGATCCA

```
        M   K   K   W   S   S   T   D   L   G   T   A   A   D   P   L   Q   K    18
GCAAGG ATG AAG AAA TGG AGC AGC ACA GAC TTG GGG ACA GCT GCG GAC CCA CTC CAA AAG    54

D   T   C   P   D   P   L   D   G   D   P   N   S   R   P   P   P   A   K   P    38
  GAC ACC TGC CCA GAC CCC CTG GAT GGA GAC CCT AAC TCC AGG CCA CCT CCA GCC AAG CCC   114

Q   L   P   T   A   K   S   R   T   R   L   F   G   K   G   D   S   E   E   A    58
  CAG CTC CCC ACG GCC AAG AGC CGC ACC CGG CTC TTT GGG AAG GGT GAC TCG GAG GAG GCT   174

F   P   V   D   C   P   H   E   E   G   E   L   D   S   C   P   T   I   T   V    78
  TTC CCG GTG GAT TGC CCC CAC GAG GAA GGT GAG TTG GAC TCC TGC CCG ACC ATC ACA GTC   234

S   P   V   I   T   I   Q   R   P   G   D   G   P   T   G   A   R   L   L   S    98
  AGC CCT GTT ATC ACC ATC CAG AGG CCA GGA GAC GGC CCC ACC GGT GCC AGG CTG CTG TCC   294
```

Fig. 1A

```
  Q   D   S   V   A   A   S   T   E   K   T   L   R   L   Y   D   R   R   S   I   118
CAG GAC TCT GTC GCC GCC AGC ACC GAG AAG ACC CTC AGG CTC TAT GAT CGC AGG AGT ATC  354

F   E   A   V   A   Q   N   N   C   Q   D   L   E   S   L   L   L   F   L   Q   138
TTT GAA GCC GTT GCT CAG AAT AAC TGC CAG GAT CTG GAG AGC CTG CTG CTC TTC CTG CAG  414

K   S   K   K   H   L   T   D   N   E   F   K   D   P   E   T   G   K   T   C   158
AAG AGC AAG AAG CAC CTC ACA GAC AAC GAG TTC AAA GAC CCT GAG ACA GGG AAG ACC TGT  474

L   L   K   A   M   L   N   L   H   D   G   Q   N   T   T   I   P   L   L   L   178
CTG CTG AAA GCC ATG CTC AAC CTG CAC GAC GGA CAG AAC ACC ACC ATC CCC CTG CTC CTG  534

E   I   A   R   Q   T   D   S   L   K   E   L   V   N   A   S   Y   T   D   S   198
GAG ATC GCG CGG CAA ACG GAC AGC CTG AAG GAG CTT GTC AAC GCC AGC TAC ACG GAC AGC  594

Y   Y   K   G   Q   T   A   L   H   I   A   I   E   R   R   N   M   A   L   V   218
TAC TAC AAG GGC CAG ACA GCA CTG CAC ATC GCC ATC GAG AGA CGC AAC ATG GCC CTG GTG  654

T   L   L   V   E   N   G   A   D   V   Q   A   A   H   G   D   F   F   K   238
ACC CTC CTG GTG GAG AAC GGA GCA GAC GTC CAG GCT GCG GCC CAT GGG GAC TTC TTT AAG  714

K   T   K   G   R   P   G   F   Y   F   G   E   L   P   L   S   L   A   A   C   258
AAA ACC AAA GGG CGG CCT GGA TTC TAC TTC GGT GAA CTG CCC CTG TCC CTG GCC GCG TGC  774

T   N   Q   L   G   I   V   K   F   L   L   Q   N   S   W   Q   T   A   D   I   278
ACC AAC CAG CTG GGC ATC GTG AAG TTC CTG CTG CAG AAC TCC TGG CAG ACG GCC GAC ATC  834

S   A   R   D   S   V   G   N   T   V   L   H   A   L   V   E   V   A   D   N   298
AGC GCC AGG GAC TCG GTG GGC AAC ACG GTG CTG CAC GCC CTG GTG GAG GTG GCC GAC AAC  894

T   A   D   N   T   K   F   V   T   S   M   Y   N   E   I   L   M   L   G   A   318
ACG GCC GAC AAC ACG AAG TTT GTG ACG AGC ATG TAC AAT GAG ATT CTG ATG CTG GGG GCC  954

K   L   H   P   T   L   K   L   E   E   L   T   N   K   K   G   M   T   P   L   338
AAA CTG CAC CCG ACG CTG AAG CTG GAG GAG CTC ACC AAC AAG AAG GGA ATG ACG CCG CTG 1014

A   L   A   A   G   T   G   K   I   G   V   L   A   Y   I   L   Q   R   E   I   358
GCT CTG GCA GCT GGG ACC GGG AAG ATC GGG GTC TTG GCC TAT ATT CTC CAG CGG GAG ATC 1074

Q   E   P   E   C   R   H   L   S   R   K   F   T   E   W   A   Y   G   P   V   378
CAG GAG CCC GAG TGC AGG CAC CTG TCC AGG AAG TTC ACC GAG TGG GCC TAC GGG CCC GTG 1134

H   S   S   L   Y   D   L   S   C   I   D   T   C   E   K   N   S   V   L   E   398
CAC TCC TCG CTG TAC GAC CTG TCC TGC ATC GAC ACC TGC GAG AAG AAC TCG GTG CTG GAG 1194

V   I   A   Y   S   S   S   E   T   P   N   R   H   D   M   L   L   V   E   P   418
GTG ATC GCC TAC AGC AGC AGC GAG ACC CCT AAT CGC CAC GAC ATG CTC TTG GTG GAG CCG 1254
```

Fig. 1B

```
      L   N   R   L   L   Q   D   K   W   D   R   F   V   K   R   I   F   Y   F   N   438
     CTG AAC CGA CTC CTG CAG GAC AAG TGG GAC AGA TTC GTC AAG CGC ATC TTC TAC TTC AAC 1314

F   L   V   Y   C   L   Y   M   I   I   F   T   M   A   A   Y   Y   R   P   V   458
     TTC CTG GTC TAC TGC CTG TAC ATG ATC ATC TTC ACC ATG GCT GCC TAC TAC AGG CCC GTG 1374

D   G   L   P   P   F   K   M   E   K   I   G   D   Y   F   R   V   T   G   E   478
     GAT GGC TTG CCT CCC TTT AAG ATG GAA ARA ATT GGA GAC TAT TTC CGA GTT ACT GGA GAG 1434

I   L   S   V   L   G   G   V   Y   F   F   F   R   G   I   Q   Y   F   L   Q   498
     ATC CTG TCT GTG TTA GGA GGA GTC TAC TTC TTT TTC CGA GGG ATT CAG TAT TTC CTG CAG 1494

R   R   P   S   M   K   T   L   F   V   D   S   Y   S   E   M   L   F   F   L   518
     AGG CGG CCG TCG ATG AAG ACC CTG TTT GTG GAC AGC TAC AGT GAG ATG CTT TTC TTT CTG 1554

Q   S   L   F   M   L   A   T   V   V   L   Y   F   S   H   L   K   E   Y   V   538
     CAG TCA CTG TTC ATG CTG GCC ACC GTG GTG CTG TAC TTC AGC CAC CTC AAG GAG TAT GTG 1614

A   S   M   V   F   S   L   A   L   G   W   T   N   M   L   Y   Y   T   R   G   558
     GCT TCC ATG GTA TTC TCC CTG GCC TTG GGC TGG ACC AAC ATG CTC TAC TAC ACC CGC GGT 1674

F   Q   Q   M   G   I   Y   A   V   M   I   E   K   M   I   L   R   D   L   C   578
     TTC CAG CAG ATG GGC ATC TAT GCC GTC ATG ATA GAG AAG ATG ATC CTG AGA GAC CTG TGC 1734

R   F   M   F   V   Y   I   V   F   L   F   G   F   S   T   A   V   V   T   L   598
     CGT TTC ATG TTT GTC TAC ATC GTC TTC TTG TTC GGG TTT TCC ACA GCG GTG GTG ACG CTG 1794

I   E   D   G   K   N   D   S   L   P   S   E   S   T   S   H   R   W   R   G   618
     ATT GAA GAC GGG AAG AAT GAC TCC CTG CCG TCT GAG TCC ACG TCG CAC AGG TGG CGG GGG 1854

P   A   C   R   P   P   D   S   S   Y   N   S   L   Y   S   T   C   L   E   L   638
     CCT GCC TGC AGG CCC CCC GAT AGC TCC TAC AAC AGC CTG TAC TCC ACC TGC CTG GAG CTG 1914

F   K   F   T   I   G   M   G   D   L   E   F   T   E   N   Y   D   F   K   A   658
     TTC AAG TTC ACC ATC GGC ATG GGC GAC CTG GAG TTC ACT GAG AAC TAT GAC TTC AAG GCT 1974

V   F   I   I   L   L   L   A   Y   V   I   L   T   Y   I   L   L   L   N   M   678
     GTC TTC ATC ATC CTG CTG CTG GCC TAT GTA ATT CTC ACC TAC ATC CTC CTG CTC AAC ATG 2034

L   I   A   L   M   G   E   T   V   N   K   I   A   Q   E   S   K   N   I   W   698
     CTC ATC GCC CTC ATG GGT GAG ACT GTC AAC AAG ATC GCA CAG GAG AGC AAG AAC ATC TGG 2094

K   L   Q   R   A   I   T   I   L   D   T   E   K   S   F   L   K   C   M   R   718
     AAG CTG CAG AGA GCC ATC ACC ATC CTG GAC ACG GAG AAG AGC TTC CTT AAG TGC ATG AGG 2154
```

Fig. 1C

```
K    A    F    R    S    G    K    L    L    Q    V    G    Y    T    P    D    G    K    D    D    738
AAG  GCC  TTC  CGC  TCA  GGC  AAG  CTG  CTG  CAG  GTG  GGG  TAC  ACA  CCT  GAT  GGC  AAG  GAC  GAC  2214

Y    R    W    C    F    R    V    D    E    V    N    W    T    T    W    N    T    N    V    G    758
TAC  CGG  TGG  TGC  TTC  AGG  GTG  GAC  GAG  GTG  AAC  TGG  ACC  ACC  TGG  AAC  ACC  AAC  GTG  GGC  2274

I    I    N    E    D    P    G    N    C    E    G    V    K    R    T    L    S    F    S    L    778
ATC  ATC  AAC  GAA  GAC  CCG  GGC  AAC  TGT  GAG  GGC  GTC  AAG  CGC  ACC  CTG  AGC  TTC  TCC  CTG  2334

R    S    S    R    V    S    G    R    H    W    K    N    F    A    L    V    P    L    L    R    798
CGG  TCA  AGC  AGA  GTT  TCA  GGC  AGA  CAC  TGG  AAG  AAC  TTT  GCC  CTG  GTC  CCC  CTT  TTA  AGA  2394

E    A    S    A    R    D    R    Q    S    A    Q    P    E    E    V    Y    L    R    Q    F    818
GAG  GCA  AGT  GCT  CGA  GAT  AGG  CAG  TCT  GCT  CAG  CCC  GAG  GAA  GTT  TAT  CTG  CGA  CAG  TTT  2454

S    G    S    L    K    P    E    D    A    E    V    F    K    S    P    A    A    S    G    E    838
TCA  GGG  TCT  CTG  AAG  CCA  GAG  GAC  GCT  GAG  GTC  TTC  AAG  AGT  CCT  GCC  GCT  TCC  GGG  GAG  2514

K    *                                                                                              840
AAG  TGA                                                                                            2520
```

GGACGTCACGCAGACAGCACTGTCAACACTGGGCCTTAGGAGACCCCGTTGCCACGGGGGGCTGCTGAGGGAACACCAG

TGCTCTGTCAGCAGCCTGGCCTGGTCTGTGCCTGCCCAGCATGTTCCCAAATCTGTGCTGGACAAGCTGTGGGAAGCGT

TCTTGGAAGCATGGGGAGTGATGTACATCCAACCGTCACTGTCCCCAAGTGAATCTCCTAACAGACTTTCAGGTTTTTA

CTCACTTTACTAAAAAAAAAAAAAAAAAAGGGCGGCCGCTTA

Fig. 1D

Full-length human VR2

Input file Flh21e11.seq; Output File Flh21e11.tra
Sequence length 2809

GGCTAGCCTGTCCTGACAGGGGAGAGTTAAGCTCCCGTTCTCCACCGTGCCGGCTGGCCAGGTGGGCTGAGGGTGACCG

AGAGACCAGAACCTGCTTGCTGGAGCTTAGTGCTCAGAGCTGGGGAGGGAGGTTCCGCCGCTCCTCTGCTGTCAGCGCC

GGCAGCCCCTCCCGGCTTCACTTCCTCCCGCAGCCCCTGCTACTGAGAAGCTCCGGGATCCCAGCAGCCGCCACGCCCT

GGCCTCAGCCTGCGGGGCTCCAGTCAGGCCAACACCGACGCGCAGCTGGGAGGAAGACAGGACCCTTGACATCTCCATC

```
                                                          M   T   S   P   S   S   P      8
TGCACAGAGGTCCTGGCTGGACCGAGCAGCCTCCTCCTCCTAGG            ATG ACC TCA CCC TCC AGC TCT CCA   24

V   F   R   L   E   T   L   D   G   G   Q   E   D   G   S   E   A   D   R   G           28
GTT TTC AGG TTG GAG ACA TTA GAT GGA GGC CAA GAA GAT GGC TCT GAG GCG GAC AGA GGA           84

K   L   D   F   G   S   G   L   P   P   M   E   S   Q   F   Q   G   E   D   R           48
AAG CTG GAT TTT GGG AGC GGG CTG CCT CCC ATG GAG TCA CAG TTC CAG GGC GAG GAC CGG          144

K   F   A   P   Q   I   R   V   N   L   N   Y   R   K   G   T   G   A   S   Q           68
AAA TTC GCC CCT CAG ATA AGA GTC AAC CTC AAC TAC CGA AAG GGA ACA GGT GCC AGT CAG          204

P   D   P   N   R   F   D   R   D   R   L   F   N   A   V   S   R   G   V   P           88
CCG GAT CCA AAC CGA TTT GAC CGA GAT CGG CTC TTC AAT GCG GTC TCC CGG GST GTC CCC          264

E   D   L   A   G   L   P   E   Y   L   S   R   T   S   R   Y   L   T   D   S          108
GAG GAT CTG GCT GGA CTT CCA GAG TAC CTG AGC AAG ACC AGC AAG TAC CTC ACC GAC TCG          324

E   Y   T   E   G   S   T   G   K   T   C   L   M   K   A   V   L   N   L   K          128
GAA TAC ACA GAG GGC TCC ACA GGT AAG ACG TGC CTG ATG AAG GCT GTG CTG AAC CTT AAG          384

D   G   V   N   A   C   I   L   P   L   L   Q   I   D   R   D   S   G   N   P          148
GAC GGA GTC AAT GCC TGC ATT CTG CCA CTG CTG CAG ATC GAC AGG GAC TCT GGC AAT CCT          444

Q   P   L   V   N   A   Q   C   T   D   D   Y   Y   R   G   H   S   A   L   H          168
CAG CCC CTG GTA AAT GCC CAG TGC ACA GAT GAC TAT TAC CGA GGC CAC AGC GCT CTG CAC          504

I   A   I   E   K   R   S   L   Q   C   V   K   L   L   V   E   N   G   A   N          188
ATC GCC ATT GAG AAG AGG AGT CTG CAG TGT GTG AAG CTC CTG GTG GAG AAT GGG GCC AAT          564

V   H   A   R   A   C   G   R   F   F   Q   K   G   Q   G   T   C   F   Y   F          208
GTG CAT GCC CGG GCC TGC GGC CGC TTC TTC CAG AAG GGC CAA GGG ACT TGC TTT TAT TTC          624

G   E   L   P   L   S   L   A   A   C   T   K   Q   W   D   V   V   S   Y   L          228
GGT GAG CTA CCC CTC TCT TTG GCC GCT TGC ACC AAG CAG TGG GAT GTG GTA AGC TAC CTC          684
```

Fig. 2A

```
  L   E   N   P   H   Q   P   A   S   L   Q   A   T   D   S   Q   G   N   T   V   248
CTG GAG AAC CCA CAC CAG CCC GCC AGC CTG CAG GCC ACT GAC TCC CAG GGC AAC ACA GTC  744

L   H   A   L   V   M   I   S   D   N   S   A   E   N   I   A   L   V   T   S   268
CTG CAT GCC CTA GTG ATG ATC TCG GAC AAC TCA GCT GAG AAC ATT GCA CTG GTG ACC ACC  804

M   Y   D   G   L   L   Q   A   G   A   R   L   C   P   T   V   Q   L   E   D   288
ATG TAT GAT GGG CTC CTC CAA GCT GGG GCC CGC CTC TGC CCT ACC GTG CAG CTT GAG GAC  864

I   R   N   L   Q   D   L   T   P   L   K   L   A   A   K   E   G   K   I   E   308
ATC GCC AAC CTG CAG GAT CTC ACG CCT CTG AAG CTG GCC GCC AAG GAG GGC AAG ATC GAG  924

I   F   R   H   I   L   Q   R   E   F   S   G   L   S   H   L   S   R   K   F   328
ATT TTC AGG CAC ATC CTG CAG CGG GAG TTT TCA GGA CTG AGC CAC CTT TCC CGA AAG TTC  984

T   E   W   C   Y   G   P   V   R   V   S   L   Y   D   L   A   S   V   D   S   348
ACC GAG TGG TGC TAT GGG CCT GTC CGG GTG TCG CTG TAT GAC CTG GCT TCT GTG GAC AGC 1044

C   E   E   N   S   V   L   E   I   I   A   F   H   C   K   S   P   H   R   H   368
TGT GAG GAG AAC TCA GTG CTG GAG ATC ATT GCC TTT CAT TGC AAG AGC CCG CAC CGA CAC 1104

R   M   V   V   L   E   P   L   N   K   L   L   Q   A   K   W   D   L   L   I   388
CGA ATG GTC GTT TTG GAG CCC CTG AAC AAA CTG CTG CAG GCG AAA TGG GAT CTG CTC ATC 1164

P   K   F   F   L   N   F   L   C   N   L   I   Y   M   F   I   F   T   A   V   408
CCC AAG TTC TTC TTA AAC TTC CTG TGT AAT CTG ATC TAC ATG TTC ATC TTC ACC GCT GTT 1224

A   Y   H   Q   P   T   L   K   K   Q   A   A   P   H   L   K   A   E   V   G   428
GCC TAC CAT CAG CCT ACC CTG AAG AAG CAG GCC GCC CCT CAC CTG AAA GCG GAG GTT GGA 1284

N   S   M   L   L   T   G   H   I   L   I   L   L   G   I   Y   L   L   V   448
AAC TCC ATG CTG CTG ACG GGC CAC ATC CTT ATC CTG CTA GGG GGG ATC TAC CTC CTC GTG 1344

G   Q   L   W   Y   F   W   R   R   H   V   F   I   W   I   S   F   I   D   S   468
GGC CAG CTG TGG TAC TTC TGG CGG CGC CAC GTG TTC ATC TGG ATC TCG TTC ATA GAC AGC 1404

Y   F   E   I   L   F   L   F   Q   A   L   L   T   V   V   S   Q   V   L   C   488
TAC TTT GAA ATC CTC TTC CTG TTC CAG GCC CTG CTC ACA GTG GTG TCC CAG GTG CTG TGT 1464

F   L   A   I   E   W   Y   L   P   L   L   V   S   A   L   V   L   G   W   L   508
TTC CTG GCC ATC GAG TGG TAC CTG CCC CTG CTT GTG TCT GCG CTG GTG CTG GGC TGG CTG 1524

N   L   L   Y   Y   T   R   G   F   Q   H   T   G   I   Y   S   V   M   I   Q   528
AAC CTG CTT TAC TAT ACA CGT GGC TTC CAG CAC ACA GGC ATC TAC AGT GTC ATG ATC CAG 1584
```

Fig. 2B

```
K   V   I   L   R   D   L   L   R   F   L   L   I   Y   L   V   F   L   F   G   548
AAG GTC ATC CTG CGG GAC CTG CTG CGC TTC CTT CTG ATC TAC TTA GTC TTC CTT TTC GGC 1644

F   A   V   A   L   V   S   L   S   Q   E   A   W   R   P   E   A   P   T   G   568
TTC GCT GTA GCC CTG GTG AGC CTG AGC CAG GAG GCT TGG CGC CCC GAA GCT CCT ACA GGC 1704

P   N   A   T   E   S   V   Q   P   M   E   G   Q   E   D   E   G   N   G   A   588
CCC AAT GCC ACA GAG TCA GTG CAG CCC ATG GAG GGA CAG GAG GAC GAG GGC AAC GGG GCC 1764

Q   Y   R   G   I   L   E   A   S   L   E   L   F   K   F   T   I   G   M   G   608
CAG TAC AGG GGT ATC CTG GAA GCC TCC TTG GAG CTC TTC AAA TTC ACC ATC GGC ATG GGC 1824

E   L   A   F   Q   E   Q   L   H   F   R   G   M   V   L   L   L   L   L   A   628
GAG CTG GCC TTC CAG GAG CAG CTG CAC TTC CGC GGC ATG GTG CTG CTG CTG CTG CTG GCC 1884

Y   V   L   L   T   Y   I   L   L   L   N   M   L   I   A   L   M   S   E   T   648
TAC GTG CTG CTC ACC TAC ATC CTG CTG CTC AAC ATG CTC ATC GCC CTC ATG AGC GAG ACC 1944

V   N   S   V   A   T   D   S   W   S   I   W   K   L   Q   K   A   I   S   V   668
GTC AAC AGT GTC GCC ACT GAC AGC TGG AGC ATC TGG AAG CTG CAG AAA GCC ATC TCT GTC 2004

L   E   M   E   N   G   Y   W   W   C   R   K   K   Q   R   A   G   V   M   L   688
CTG GAG ATG GAG AAT GGC TAT TGG TGG TGC AGG AAG AAG CAG CGG GCA GGT GTG ATG CTG 2064

T   V   G   T   K   P   D   G   S   P   D   E   R   W   C   F   R   V   E   E   708
ACC GTT GGC ACT AAG CCA GAT GGC AGC CCG GAT GAG CGC TGG TGC TTC AGG GTG GAG GAG 2124

V   N   W   A   S   W   E   Q   T   L   P   T   L   C   E   D   P   S   G   A   728
GTG AAC TGG GCT TCA TGG GAG CAG ACG CTG CCT ACG CTG TGT GAG GAC CCG TCA GGG GCA 2184

G   V   P   R   T   L   E   N   P   V   L   A   S   P   P   K   E   D   E   D   748
GGT GTC CCT CGA ACT CTC GAG AAC CCT GTC CTG GCT TCC CCT CCC AAG GAG GAT GAG GAT 2244

G   A   S   E   E   N   Y   V   P   V   Q   L   L   Q   S   N   *               765
GGT GCC TCT GAG GAA AAC TAT GTG CCC GTC CAG CTC CTC CAG TCC AAC TGA             2295

TGGCCCAGATGCAGCAGGAGGCCAGAGGACAGAGCAGAGGATCTTTCCAACCACATCTGCTGGCTCTGGGGTCCCAGTG

AATTCTGGTGGCAAATATATATTTTCACTAACTCAAAAAAAAAAAAAAAAAAAAAAAAAAAAAAAAAAAAAAAAAAAA
```

Fig. 2C

Partial human VR2 alternate form

Input file frhob12c4.seg; Output File frhob12c4.tra
Sequence length 1489

```
         G   R   F   F   Q   K   G   Q   G   T   C   F   Y   F   G   E   L   P   L    19
        GC GGC CGC TTC TTC CAG AAG GGC CAA GGG ACT TGC TTT TAT TTC GGT GAG CTA CCC CTC   57

S   L   A   A   C   T   K   Q   W   D   V   V   S   Y   L   L   E   N   P   H    39
    TCT TTG GCC GCT TGC ACC AAG CAG TGG GAT GTG GTA AGC TAC CTC CTG GAG AAC CCA CAC   117

Q   P   A   S   L   Q   A   T   D   S   Q   G   N   T   V   L   H   A   L   V    59
    CAG CCC GCC AGC CTG CAG GCC ACT GAC TCC CAG GGC AAC ACA GTC CTG CAT GCC CTA GTG   177

M   I   S   D   N   S   A   E   N   I   A   L   V   T   S   M   Y   D   G   L    79
    ATG ATC TCG GAC AAC TCA GCT GAG AAC ATT GCA CTG GTG ACC AGC ATG TAT GAT GGG CTC   237

L   Q   A   G   A   R   L   C   P   T   V   Q   L   E   D   I   R   N   L   Q    99
    CTC CAA GCT GGG GCC CGC CTC TGC CCT ACC GTG CAG CTT GAG GAC ATC CGC AAC CTG CAG   297

D   L   T   P   L   K   L   A   A   K   E   G   K   I   E   I   F   R   H   I   119
    GAT CTC ACG CCT CTG AAG CTG GCC GCC AAG GAG GGC AAG ATC GAG ATT TTC AGG CAC ATC   357

L   Q   R   E   F   S   G   L   S   H   L   S   R   K   F   T   E   W   C   Y   139
    CTG CAG CGG GAG TTT TCA GGA CTG AGC CAC CTT TCC CGA AAG TTC ACC GAG TGG TGC TAT   417

G   P   V   R   V   S   L   Y   D   L   A   S   V   D   S   C   E   E   N   S   159
    GGG CCT GTC CGG GTG TCG CTG TAT GAC CTG GCT TCT GTG GAC AGC TGT GAG GAG AAC TCA   477

V   L   E   I   I   A   F   H   C   K   S   P   H   R   H   R   M   V   V   L   179
    GTG CTG GAG ATC ATT GCC TTT CAT TGC AAG AGC CCG CAC CGA CAC CGA ATG GTC GTT TTG   537

E   P   L   N   K   L   L   Q   A   K   W   D   L   L   I   P   K   F   F   L   199
    GAG CCC CTG AAC AAA CTG CTG CAG GCG AAA TGG GAT CTG CTC ATC CCC AAG TTC TTC TTA   597

N   F   L   C   N   L   I   Y   M   F   I   F   T   A   V   A   Y   H   Q   P   219
    AAC TTC CTG TGT AAT CTG ATC TAC ATG TTC ATC TTC ACC GCT GTT GCC TAC CAT CAG CCT   657

T   L   K   K   Q   A   A   P   H   L   K   A   E   V   G   N   S   M   L   L   239
    ACC CTG AAG AAG CAG GCC GCC CCT CAC CTG AAA GCG GAG GTT GGA AAC TCC ATG CTG CTG   717

T   G   H   I   L   I   L   L   G   G   I   Y   L   L   V   G   Q   L   W   Y   259
    ACG GGC CAC ATC CTT ATC CTG CTA GGG GGA ATC TAC CTC CTC GTG GGC CAG CTG TGG TAC   777

F   W   R   R   H   V   F   I   W   I   S   F   I   D   S   Y   F   E   I   L   279
    TTC TGG CGG CGC CAC GTG TTC ATC TGG ATC TCG TTC ATA GAC AGC TAC TTT GAA ATC CTC   837
```

Fig. 3A

```
      F   L   F   Q   A   L   L   T   V   V   S   Q   V   L   C   F   L   A   I   E   299
     TTC CTG TTC CAG GCC CTG CTC ACA GTG GTG TCC CAG GTG CTG TGT TTC CTG GCC ATC GAG  897

W   Y   L   P   L   L   V   S   A   L   V   L   G   W   L   N   L   L   Y   Y   319
     TGG TAC CTG CCC CTG CTT GTG TCT GCG CTG GTG CTG GGC TGG CTG AAC CTG CTT TAC TAT  957

T   R   G   F   Q   H   T   G   I   Y   S   V   M   I   Q   K   K   A   I   S   339
     ACA CGT GGC TTC CAG CAC ACA GGC ATC TAC AGT GTC ATG ATC CAG AAG AAA GCC ATC TCT 1017

V   L   E   M   E   N   G   Y   W   W   C   R   K   K   Q   R   A   G   V   M   359
     GTC CTG GAG ATG GAG AAT GGC TAT TGG TGG TGC AGG AAG AAG CAG CGG GCA GGT GTG ATG 1077

L   T   V   G   T   K   P   D   G   S   P   D   E   R   W   C   F   R   V   E   379
     CTG ACC GTT GGC ACT AAG CCA GAT GGC AGC CCG GAT GAG CGC TGG TGC TTC AGG GTG GAG 1137

E   V   N   W   A   S   W   E   Q   T   L   P   T   L   C   E   D   P   S   G   399
     GAG GTG AAC TGG GCT TCA TGG GAG CAG ACG CTG CCT ACG CTG TGT GAG GAC CCG TCA GGG 1197

A   G   V   P   R   T   L   E   N   P   V   L   A   S   P   P   K   E   D   E   419
     GCA GGT GTC CCT CGA ACT CTC GAG AAC CCT GTC CTG GCT TCC CCT CCC AAG GAG GAT GAG 1257

D   G   A   S   E   E   N   Y   V   P   V   Q   L   L   Q   S   N   *           437
     GAT GGT GCC TCT GAG GAA AAC TAT GTG CCC GTC CAG CTC CTC CAG TCC AAC TGA          1311

TGGCCCAGATGCAGCAGGAGGCCAGAGGACAGAGCAGAGGATCTTTCCAACCACATCTGCTGGCTCTGGGGTCCCAGTG

AATTCTGGTGGCAAATATATATTTTTCACTAACTCAAAAAAAAAAAAAAAAAAAAAAAAAAAAAAAAAAAAAAAAAGGA

GCGGACGCGTGGGTCGAC
```

Fig. 3B

Partial rat VR2

Input file Flrxb147g11.seq; Output File Flrxb147g11.tra
Sequence length 1794

```
      S   T   H   A   S   A   L   S   L   A   A   C   T   K   Q   W   D   V   V    19
    G TCG ACC CAC GCG TCC GCT CTT TCT CTG GCT GCG TGC ACC AAG CAG TGG GAT GTG GTG    57

T   Y   L   L   E   N   P   H   Q   P   A   S   L   E   A   T   D   S   L   G  39
    ACC TAC CTC CTG GAG AAC CCA CAC CAG CCG GCC AGC CTG GAG GCC ACC GAC TCC CTG GGC 117

N   T   V   L   H   A   L   V   M   I   A   D   N   S   P   E   N   S   A   L  59
    AAC ACA GTC CTG CAT GCT CTG GTA ATG ATT GCA GAT AAC TCG CCT GAG AAC AGT GCC CTG 177

V   I   H   M   Y   D   G   L   L   Q   M   G   A   R   L   C   P   T   V   Q  79
    GTG ATC CAC ATG TAC GAC GGG CTT CTA CAA ATG GGG GCG CGC CTC TGC CCC ACT GTG CAG 237

L   E   E   I   S   N   H   Q   G   L   T   P   L   K   L   A   A   K   E   G  99
    CTT GAG GAA ATC TCC AAC CAC CAA GGC CTC ACA CCC CTG AAA CTA GCC GCC AAG GAA GGC 297

K   I   E   I   F   R   H   I   L   Q   R   E   F   S   G   P   Y   Q   P   L 119
    AAA ATC GAG ATT TTC AGG CAC ATT CTG CAG CGG GAA TTC TCA GGA CCG TAC CAG CCC CTT 357

S   R   K   F   T   E   W   C   Y   G   P   V   R   V   S   L   Y   D   L   S 139
    TCC CGA AAG TTT ACT GAG TGG TGT TAC GGT CCT GTG CGG GTA TCG CTG TAC GAC CTG TCC 417

S   V   D   S   W   E   K   N   S   V   L   E   I   I   A   F   H   C   K   S 159
    TCT GTG GAC AGC TGG GAA AAG AAC TCG GTG CTG GAG ATC ATC GCT TTT CAT TGC AAG AGC 477

P   N   R   H   R   M   V   V   L   E   P   L   N   K   L   L   Q   E   K   W 179
    CCG AAC CGG CAC CGC ATG GTG GTT TTA GAA CCA CTG AAC AAG CTT CTG CAG GAG AAA TGG 537

D   R   L   V   S   R   P   F   F   N   F   A   C   Y   L   V   Y   M   F   I 199
    GAT CGG CTC GTC TCA AGA TTC TTC TTC AAC TTC GCC TGC TAC TTG GTC TAC ATG TTC ATC 597

F   T   V   V   A   Y   H   Q   P   S   L   D   Q   P   A   I   P   S   S   K 219
    TTC ACC GTC GTT GCC TAC CAC CAG CCT TCC CTG GAT CAG CCA GCC ATC CCC TCA TCA AAA 657

A   T   F   G   E   S   M   L   L   G   H   I   L   I   L   L   G   G   I 239
    GCG ACT TTT GGG GAA TCC ATG CTG CTG CTG GGC CAC ATT CTG ATC CTG CTT GGG GGT ATT 717

Y   L   L   L   G   Q   L   W   Y   F   W   R   R   L   F   I   W   I   S 259
    TAC CTC TTA CTG GGC CAG CTG TGG TAC TTT TGG CGG CGG CGC CTG TTT ATC TGG ATC TCA 777

F   M   D   S   Y   F   E   I   L   F   L   L   Q   A   L   L   T   V   L   S 279
    TTC ATG GAC AGC TAC TTT GAA ATC CTC TTT CTC CTT CAG GCT CTG CTC ACA GTG CTG TCC 837
```

Fig. 4A

```
    Q   V   L   R   F   M   E   T   E   W   Y   L   P   L   L   V   L   S   L   V    299
   CAG GTG CTG CGC TTC ATG GAG ACT GAA TGG TAC CTA CCC CTG CTA GTG TTA TCC CTA GTG    897

L   G   W   L   N   L   L   Y   Y   T   R   G   F   Q   H   T   G   I   Y   S    319
   CTG GGC TGG CTG AAC CTG CTT TAC TAC ACA CGG GGC TTT CAG CAC ACA GGC ATC TAC AGT    957

V   M   I   Q   K   V   I   L   R   D   L   L   R   F   L   L   V   Y   L   V    339
   GTC ATG ATC CAG AAG GTC ATC CTT CGA GAC CTG CTC CGT TTC CTG CTG GTC TAC CTG GTC   1017

F   L   F   G   F   A   V   A   L   V   S   L   S   R   E   A   R   S   P   K    359
   TTC CTT TTC GGC TTT GCT GTA GCC CTA GTA AGC TTG AGC'AGA GAG GCC CGA AGT CCC AAA   1077

A   P   E   D   N   N   S   T   V   T   E   Q   P   T   V   G   Q   E   E   E    379
   GCC CCT GAA GAT AAC AAC TCC ACA GTG ACG GAA CAG CCC ACG GTG GGC CAG GAG GAG GAG   1137

P   A   P   Y   R   S   I   L   D   A   S   L   E   L   F   K   F   T   I   G    399
   CCA GCT CCA TAT CGG AGC ATT CTG GAT GCC TCC CTA GAG CTG TTC AAG TTC ACC ATT GGT   1197

M   G   E   L   A   F   Q   E   Q   L   R   F   R   G   V   V   L   L   L   L    419
   ATG GGG GAG CTG GCT TTC CAG GAA CAG CTG CGT TTT CGT GGG GTG GTC CTG CTG TTG CTG   1257

L   A   Y   V   L   L   T   Y   V   L   L   N   M   L   I   A   L   M   S    439
   TTG GCC TAC GTC CTT CTC ACC TAC GTC CTG CTG CTC AAC ATG CTC ATT GCT CTC ATG AGC   1317

E   T   V   N   H   V   A   D   N   S   W   S   I   W   K   L   Q   K   A   I    459
   GAA ACT GTC AAC CAC GTT GCT GAC AAC AGC TGG AGC ATC TGG AAG TTG CAG AAA GCC ATC   1377

S   V   L   E   M   E   N   G   Y   W   C   R   R   K   K   H   R   E   G    479
   TCT GTC TTG GAG ATG GAG AAT GGT TAC TGG TGG TGC CGG AGG AAG AAA CAT CGT GAA GGG   1437

R   L   L   K   V   G   T   R   G   D   G   T   P   D   E   R   W   C   F   R    499
   AGG CTG CTG AAA GTC GGC ACC AGG GGG GAT GGT ACC CCT GAT GAG CGC TGG TGC TTC AGG   1497

V   E   E   V   N   W   A   A   W   E   K   T   L   P   T   L   S   E   D   P    519
   GTG GAG GAA GTA AAT TGG GCT GCT TGG GAG AAG ACT CTT CCC ACC TTA TCT GAG GAT CCA   1557

S   G   P   G   I   T   G   N   K   K   N   P   T   S   K   P   G   K   N   S    539
   TCA GGG CCA GGC ATC ACT GGT AAT AAA AAG AAC CCA ACC TCT AAA CCG GGG AAG AAC AGT   1617

A   S   E   E   D   H   L   P   L   Q   V   L   Q   S   P   *                     555
   GCC TCA GAG GAA GAC CAT CTG CCC CTT CAG GTC CTC CAG TCC CCC TGA                   1665

TGGCCCAGATGCAGCAGCAGGCTGGCAGGATGGAGTAGGGAATCTTCCCAGCCACACCAGAGGCTACTGAATTTTGGTG

GAAATATAAATATTTTTTTTTGCATAAAAAAAAAAAAAAAAGGGCGGCCGC
```

Fig. 4B

GAP of: humanvr2.pep check: 5746 from: 1 to: 764 humanVR2 Flh21e11 to: humanvr1.pep check: 6877 from: 1 to: 839 humanVR1 _Fbh18547pat - fchrb87a6, 3909 bases, 4554 checksum.

Symbol comparison table:
/ddm_local/gcg/gcg_9.1/gcgcore/data/rundata/blosum62.cmp
CompCheck: 6430

```
         Gap Weight:     12  Average Match:     2.912
      Length Weight:      4  Average Mismatch: -2.003

Quality:   1530         Length:       850
              Ratio:  2.003           Gaps:        10
Percent Similarity: 55.378 Percent Identity:    46.348
```

Match display thresholds for the alignment(s):
| = IDENTITY
: = 2
. = 1 humanvr2.pep x humanvr1.pep

```
  1 .........................................MTSPSSSPVF  10
                                              |. |  . .|
  1 MKKWSSTDLGTAADPLQKDTCPDPLDGDPNSRPPPAKPQLPTAKSRTRLF  50

11 RLETLDGGQEDGSEADRGKLDFGSGLPPMESQFQGEDRKFAPQIRVNLNY  60
           :       |.||     :    .     :      |    |.
 51 GKGDSEEAFPVDCPHEEGELDSCPTI.TVSPVITIQRPGDGPTGARLLSQ  99

61 RKGTGASQPDPNRFDRDRLFNAVSRGVPEDLAGLPEYLSKTSKYLTDSEY 110
     ..:    :||  :| ||..   :||   |  :| |. |:|||.|:
100 DSVAASTEKTLRLYDRRSIFEAVAQNNCQDLESLLLFLQKSKKHLTDNEF 149

111 TEGSTGKTCLMKAVLNLKDGVNACILPLLQIDRDSGNPQPLVNAQCTDDY 160
    :  ||||||:||.||| || |   ||:|| . . ||||   || |
150 KDPETGKTCLLKAMLNLHDGQNTTIPLLLEIARQTDSLKELVNASYTDSY 199

161 YRGHSALHIAIEKRSLQCVKLLVENGANVHARACGRFFQKGQG.TCFYFG 209
    |:| .|||||||:|.:  | ||||||.| | | | ||.|  .|   ||||
200 YKGQTALHIAIERRNMALVTLLVENGADVQAAAHGDFFKKTKGRPGFYFG 249
```

Fig. 5A

```
210 ELPLSLAACTKQWDVVSYLLENPHQPASLQATDSQGNTVLHALVMISDNS 259
    ||||||||||  |  :| :||:|  ||  : | || |||||||||| :.||.
250 ELPLSLAACTNQLGIVKFLLQNSWQTADISARDSVGNTVLHALVEVADNT 299

260 AENIALVTSMYDGLLQAGARLCPTVQLEDIRNLQDLTPLKLAAKEGKIEI 309
    |:|   |||||.  :|  ||:| ||..||::  |  .:||| |||  ||| :
300 ADNTKFVTSMYNEILMLGAKLHPTLKLEELTNKKGMTPLALAAGTGKIGV 349

310 FRHILQREFS..GLSHLSRKFTEWCYGPVRVSLYDLASVDSCEENSVLEI 357
    :|||||      ||||||||| ||||  ||||. :|.||.||||| :
350 LAYILQREIQEPECRHLSRKFTEWAYGPVHSSLYDLSCIDTCEKNSVLEV 399

358 IAF.HCKSPHRHRMVVLEPLNKLLQAKWDLLIPK.FFLNFLCNLIYMFIF 405
    ||:   ..|.|| |...||||:|||  |||  : :  |: |||   :|| ||
400 IAYSSSETPNRHDMLLVEPLNRLLQDKWDRFVKRIFYFNFLVYCLYMIIF 449

406 TAVAYHQPTLKKQAAPHLKAEVGNSMLLTGHILILLGGIYLLVGQLWYFW 455
    |  ||:.|    |    .:|.  .|| ||  .|||:|    :  ||
450 TMAAYYRPV..DGLPPFKMEKIGDYFRVTGEILSVLGGVYFFFRGIQYFL 497

456 RRHVFIWISFIDSYFEILFLFQALLTVVSQVLCFLAIEWYLPLLVSALVL 505
    .|  .  |:|||  |.||  |.|   ||  |   :. |.  :| .| |
498 QRRPSMKTLFVDSYSEMLFFLQSLFMLATVVLYFSHLKEYVASMVFSLAL 547

506 GWLNLLYYTRGFQHTGIYSVMIQKVILRDLLRFLLIYLVFLFGFAVALVS 555
    ||  |:|||||||||   |||.|||:|.|||||  ||: :|:||||||. |.|.
548 GWTNMLYYTRGFQQMGIYAVMIEKMILRDLCRFMFVYIVFLFGFSTAVVT 597

556 LSQEAWRPEAPTGPNATESVQPMEGQEDEGNGAQYRGILEASLELFKFTI 605
    |  ::      |. .|      |    | :   . |  :    |||||||
598 LIEDGKNDSLPSESTSHRWRGPACRPPD....SSYNSLYSTCLELFKFTI 643

606 GMGELAFQEQLHFRGMVLLLLAYVLLTYILLLNMLIALMSETVNSVATD 655
    |||:| |    |:  ::|||||||:|||||||||||||||  ||||   :| :
644 GMGDLEFTENYDFKAVFIILLLAYVILTYILLLNMLIALMGETVNKIAQE 693

656 SWSIWKLQKAISVLEMENGYWWC.RKKQRAGVMLTVGTKPDGSPDERWCF 704
    | .||||:||.:|: |   : | ||  |.| :|| |||  | ||||
694 SKNIWKLQRAITILDTEKSFLKCMRKAFRSGKLLQVGYTPDGKDDYRWCF 743

705 RVEEVNWASWEQTLPTLCEDPSGA.GVPRTLENPVLASPPKEDEDGASEE 753
    ||:||||  .|    : |||  || ||| ||  ..|   |  .
744 RVDEVNWTTWNTNVGIINEDPGNCEGVKRTLSFSLRSS....RVSGRHWK 789

754 NYVPVQLLQSN........................................ 764
    |: | ||.
790 NFALVPLLREASARDRQSAQPEEVYLRQFSGSLKPEDAEVFKSPAASGEK 839
```

Fig. 5B

GAP of: humanvr2.seq check: 8853 from: 1 to: 2809 humanVR2 21e11a, 2809 bases, 8853 checksum.

to: humanvr1.seq check: 4554 from: 1 to: 3909 humanVR1 Fbh18547pat - Import - complete

Symbol comparison table:
/ddm_local/gcg/gcg_9.1/gcgcore/data/rundata/nwsgapdna.cmp
CompCheck: 8760

```
         Gap Weight:        50    Average Match:   10.000
      Length Weight:         3    Average Mismatch: 0.000

Quality:     14359           Length:     3934
              Ratio:     5.112             Gaps:       15
  Percent Similarity:   55.316   Percent Identity:  55.316
```

Match display thresholds for the alignment(s):
```
        | = IDENTITY
        : = 5
        . = 1
``` humanvr2.seq x humanvr1.seq

```
   1 ........................GGCTAGCCTGTCCTGACAGGGGAGAG  26
                              | |  | |   || |||
 801 TGTCCACAGTAGTCCCCCCTTATCCACGGGTGTCACTTTCCATGGGTTCA 850

27 TTAAGCTCCCGTTCTCCACCGTGCCGGCTGGCCAGGTGGGCTGAGGGTGA  76
     | | | | ||   |||| ||             |  |||        | |
 851 GTTATTTGCGGTCAACCACGGTCTGCCAATATTAAATGGAAAATTCTTCA 900

77 CCGAGAGACCAGAACCTGCTTGCTGGAGCTTAGTGCTCAGAGCTGGGGAG 126
       ||   |||    | |  |||  ||   |  ||  ||||| |   |  ||
 901 AACAGTTCCCAAGTTTTCCCTTGTGCATTGTTCTGAGCAGTGTGATGAAG 950

127 GGAGGTTCCGCCGCTCCTCTGCTGTCAGCGCCGGCAGCCCCTCCCGGCTT 176
      |    ||  ||         |    ||   |   |        ||| ||
 951 AGTCTCTGCCGTGCCATCTGGGATGCAAACCGTCCCTGTGTCCCCCACGT 1000
```

Fig. 6A

```
 177 CACTTCCTCCCGCAGCCCCTGCTACTGAGAAGCTCCGGGATCCCAGCAGC  226
     |  ||    ||| ||   || ||  |   ||  |||
1001 CCAGGCCGTAGATGCTCCCCGCCGGTCAGTCACTTAGTCGTCAGATCGCC 1050

227 CGCCACGCCCTGGC.....................CTCAGCCTGCGGG  253
     || |   ||                            ||  |||  ||
1051 CGTCCTGGTATCACAGTGCTTCTGTTCAGGTTGCACACTGGGCCACAGAG 1100

254 GCTCCAGTCAGGCCAACACCGACGCGCAGCTGGGAGGAAG..........  293
     | |||||  |||   |    | |||||| ||        |
1101 GATCCAGCAAGGATGAAGAAATGGAGCAGCACAGACTTGGGGACAGCTGC 1150

294 ...........ACAGGACCCTTGACATCTCCATCTGCACAGAGGTCCTG  331
                | |||||  |  || |   ||  ||| |  ||| |||
1151 GGACCCACTCCAAAAGGACACCTGCCCAGACCCCCTGGATGGAGACCCTA 1200

332 GCTGGACCGAGCAGCCTCCTCCTCCTAGGATGACCTCACCCTCCAGC..T  379
     || |       |||    ||   ||  ||  ||   ||   |||
1201 ACTCCAGGCCACCTCCAGCCAAGCCCCAGCTCCCCACGGCCAAGAGCCGC 1250

380 CTCCAGTTTTCAGGTTGGAGACATTAGATGGAGGCCAAGAAGATGGCTCT  429
     ||  |   ||  ||    |  |   |  ||||||         | |||  |
1251 ACCCGGCTCTTTGGGAAGGGTGACTCGGAGGAGGCTTTCCCGGTGGATTG 1300

430 GAGGCGGACAGAGGAAAGCTGGATTTTGGGAGCGGGCTGCCTCCCATGGA  479
          |   |||  |  ||  |  |  ||  | |         |
1301 CCCCCACGAGGAAGGTGAGTTGGACTCCTGCCCGACCATCACAGTCAGCC 1350

480 GTCACAGTTCCAGGGCGAGGACCGGAAATTCGCCCCTCAGATAAGAGTCA  529
        |    |||   |||| | |||  |   ||  ||   |
1351 CTGTTATCACCATCCAGAGGCCAGGAGACGGCCCCACCGGTGCCAGG...C 1398

530 ACCTCAACTACCGAAAGGGAACAGGTGCCAGTCAGCCGGATCCAAACCGA  579
       ||  ||     |  ||  || || |  |  |  |
1399 TGCTGTCCCAGGACTCTGTCGCCGCCAGCACCGAGAAGACCCTCAGGCTC 1448

580 TTTGACCGAGATCGGCTCTTCAATGCGGTCTCCCGGGGTGTCCCCGAGGA  629
      | ||| ||   |  ||||  | || ||| |  |    |   |||||
1449 TATGATCGCAGGAGTATCTTTGAAGCCGTTGCTCAGAATAACTGCCAGGA 1498

630 TCTGGCTGGACTTCCAGAGTACCTGAGCAAGACCAGCAAGTACCTCACCG  679
     ||||| | |||    ||  | |||| |||| ||| ||| |||||||| |
1499 TCTGGAGAGCCTGCTGCTCTTCCTGCAGAAGAGCAAGAAGCACCTCACAG 1548
```

Fig. 6B

```
 680 ACTCGGAATACACAGAGGGCTCCACAGGTAAGACGTGCCTGATGAAGGCT  729
     ||  || || |||     ||||| |||||  || ||| ||||| ||
1549 ACAACGAGTTCAAAGACCCTGAGACAGGGAAGACCTGTCTGCTGAAAGCC 1598

730 GTGCTGAACCTTAAGGACGGAGTCAATGCCTGCATTCTGCCACTGCTGCA  779
     ||||  |||||  |  ||||||   ||  ||  ||| |  |  || ||| |
1599 ATGCTCAACCTGCACGACGGACAGAACACCACCATCCCCCTGCTCCTGGA 1648

780 GATCGACAGGGACTCTGGCAATCCTCAGCCCCTGGTAAATGCCCAGTGCA  829
     |||||   ||  | ||| |  ||  || || || || ||  |||   | ||
1649 GATCGCGCGGCAAACGGACAGCCTGAAGGAGCTTGTCAACGCCAGCTACA 1698

830 CAGATGACTATTACCGAGGCCACAGCGCTCTGCACATCGCCATTGAGAAG  879
     | ||   ||| ||| |||||  | ||||||||||||||||||||| ||||
1699 CGGACAGCTACTACAAGGGCCAGACAGCACTGCACATCGCCATCGAGAGA 1748

880 AGGAGTCTGCAGTGTGTGAAGCTCCTGGTGGAGAATGGGGCCAATGTGCA  929
     | |  ||    ||||   |||||||||||||||| || || | || ||
1749 CGCAACATGGCCCTGGTGACCCTCCTGGTGGAGAACGGAGCAGACGTCCA 1798

930 TGCCCGGGCCTGCGGCCGCTTCTTCCAGAAGGGCCAAG...GGACTTGCT  976
     | |   |||| ||  ||||||  ||||   |||| || || ||
1799 GGCTGCGGCCCATGGGGACTTCTTTAAGAAAACCAAAGGGCGGCCTGGAT 1848

977 TTTATTTCGGTGAGCTACCCCTCTCTTTGGCCGCTTGCACCAAGCAGTGG 1026
     | || ||||||||| || |||||| || |||||| |||||||| ||| |
1849 TCTACTTCGGTGAACTGCCCCTGTCCCTGGCCGCGTGCACCAACCAGCTG 1898

1027 GATGTGGTAAGCTACCTCCTGGAGAACCCACACCAGCCCGCCAGCCTGCA 1076
     |   | || | | | |||  ||||| |    ||| | ||| | |
1899 GGCATCGTGAAGTTCCTGCTGCAGAACTCCTGGCAGACGGCCGACATCAG 1948

1077 GGCCACTGACTCCCAGGGCAACACAGTCCTGCATGCCCTAGTGATGATCT 1126
     ||||  |||||  |||||||||| || ||||| |||| |||   ||
1949 CGCCAGGGACTCGGTGGGCAACACGGTGCTGCACGCCCTGGTGGAGGTGG 1998

1127 CGGACAACTCAGCTGAGAACATTGCACTGGTGACCAGCATGTATGATGGG 1176
     |||||| | |  || |  ||  || |  |  ||||  ||| ||| | ||
1999 CCGACAACACGGCCGACAACACGAAGTTTGTGACGAGCATGTACAATGAG 2048

1177 CTCCTCCAAGCTGGGGCCCGCCTCTGCCCTACCGTGCAGCTTGAGGACAT 1226
     | ||    ||||||||  ||  ||| ||  || || ||||| ||||| |
2049 ATTCTGATGCTGGGGGCCAAACTGCACCCGACGCTGAAGCTGGAGGAGCT 2098
```

Fig. 6C

```
1227 CCGCAACCTGCAGGATCTCACGCCTCTGAAGCTGGCCGCCAAGGAGGGCA 1276
     |  ||||  | ||| |  ||||||  ||| ||||||  ||  |   ||| |
2099 CACCAACAAGAAGGGAATGACGCCGCTGGCTCTGGCAGCTGGGACCGGGA 2148

1277 AGATCGAGATTTTCAGGCACATCCTGCAGCGGGAGTT......TTCAGGA 1320
     ||||||| | | ||    | || || ||||||||| |      | |
2149 AGATCGGGGTCTTGGCCTATATTCTCCAGCGGGAGATCCAGGAGCCCGAG 2198

1321 CTGAGCCACCTTTCCCGAAAGTTCACCGAGTGGTGCTATGGGCCTGTCCG 1370
       ||  ||||| |||  | ||||||||||||||  ||| ||||| || |
2199 TGCAGGCACCTGTCCAGGAAGTTCACCGAGTGGGCCTACGGGCCCGTGCA 2248

1371 GGTGTCGCTGTATGACCTGGCTTCTGTGGACAGCTGTGAGGAGAACTCAG 1420
     ||||||||  ||||||  | |   | ||| ||| ||| ||||||||| |
2249 CTCCTCGCTGTACGACCTGTCCTGCATCGACACCTGCGAGAAGAACTCGG 2298

1421 TGCTGGAGATCATTGCCTTTCATTGCA...AGAGCCCGCACCGACACCGA 1467
     ||||||||  | || |||| |   ||    ||| ||| | || |||
2299 TGCTGGAGGTGATCGCCTACAGCAGCAGCGAGACCCCTAATCGCCACGAC 2348

1468 ATGGTCGTTTTGGAGCCCCTGAACAAACTGCTGCAGGCGAAATGGGA... 1514
     |||  |    |||||| | |||| | ||||| ||||||  || |||
2349 ATGCTCTTGGTGGAGCCGCTGAACCGACTCCTGCAGGACAAGTGGGACAG 2398

1515 TCTGCTCATCCCCAAGTTCTTCTTAAACTTCCTGTGTAATCTGATCTACA 1564
       |||  | || |||| ||| ||||||||||| |     |  | ||||
2399 ATTCGTCAAGCGCATCTTCTACTTCAACTTCCTGGTCTACTGCCTGTACA 2448

1565 TGTTCATCTTCACCGCTGTTGCCTACCATCAGCCTACCCTGAAGAAGCAG 1614
     ||  |||||||||| |  ||||||| |     |||       |
2449 TGATCATCTTCACCATGGCTGCCTACTA....CAGGCCCGTGGATGGCTT 2494

1615 GCCGCCCCTCACCTGAAAGCGGAGGTTGGAAACTCCATGCTGCTGACGGG 1664
     |||  ||| |  |   | ||  |   ||||| |||  ||  |   | ||
2495 GCCTCCCTTTA..AGATGGAAAAAATTGGAGACTATTTCCGAGTTACTGG 2542

1665 CCACATCCTTATCCTGCTAGGGGGGATCTACCTCCTCGTGGGCCAGCTGT 1714
      |||||    ||  ||| ||  ||| ||  ||   |  |       |
2543 AGAGATCCTGTCTGTGTTAGGAGGAGTCTACTTCTTTTTCCGAGGGATTC 2592

1715 GGTACTTCTGGCGGCGCCACGTGTTCATCTGGATCTCGTTCATAGACAGC 1764
     |||  ||| || |    ||    | ||| ||  |  |  || |||||||
2593 AGTATTTCCTGCAGAGGCGGCCGTCGATGAAGACCCTGTTTGTGGACAGC 2642
```

Fig. 6D

```
1765 TACTTTGAAATCCTCTTCCTGTTCCAGGCCCTGCTCACAGTGGTGTCCCA 1814
     |||  ||| || || ||| |  | ||| | ||| |||    |||   ||
2643 TACAGTGAGATGCTTTTCTTTCTGCAGTCACTGTTCATGCTGGCCACCGT 2692

1815 GGTGCTGTGTTTCCTGGCCATCGAGTGGTACCTGCCCCTGCTTGTGTCTG 1864
     ||||||||   |||      | || || ||| || |     | ||| |
2693 GGTGCTGTACTTCAGCCACCTCAAGGAGTATGTGGCTTCCATGGTATTCT 2742

1865 CGCTGGTGCTGGGCTGGCTGAACCTGCTTTACTATACACGTGGCTTCCAG 1914
     | ||||   |||||||||   ||| ||||  || || || || ||||||
2743 CCCTGGCCTTGGGCTGGACCAACATGCTCTACTACACCCGCGGTTTCCAG 2792

1915 CACACAGGCATCTACAGTGTCATGATCCAGAAGGTCATCCTGCGGGACCT 1964
     || |  |||||||| |   ||||||||  || || | |||||| |||||
2793 CAGATGGGCATCTATGCCGTCATGATAGAGAAGATGATCCTGAGAGACCT 2842

1965 GCTGCGCTTCCTTCTGATCTACTTAGTCTTCCTTTTCGGCTTCGCTGTAG 2014
     |  || ||| |  | |||||  ||||||  | ||||||  ||    ||
2843 GTGCCGTTTCATGTTTGTCTACATCGTCTTCTTGTTCGGGTTTTCCACAG 2892

2015 CCCTGGTGAGCCTGAGCCAGGAGGCTTGGCGCCCCGAAGCTCCTACAGGC 2064
     |  ||||| ||||   |  ||  |    |      |      || | |
2893 CGGTGGTGACGCTGATTGAAGACGGGAAGAATGACTCCCTGCCGTCTGAG 2942

2065 CCCAATGCCACAGAGTCAGTGCAGCCCATGGAGGGACAGGAGGACGAGGG 2114
        |||                    |   |  ||  | |   | |
2943 TCCA............CGTCGCACAGGTGGCGGGGGCCTGCCTGCAGGCC 2980

2115 CAACGGGGCCCAGTACAGGGGTATCCTGGAAGCCTCCTTGGAGCTCTTCA 2164
     | ||    |    |||   | |        ||| | ||||||||  ||||
2981 CCCCGATAGCTCCTACAACAGCCTGTACTCCACCTGCCTGGAGCTGTTCA 3030

2165 AATTCACCATCGGCATGGGCGAGCTGGCCTTCCAGGAGCAGCTGCACTTC 2214
     | |||||||||||||||||| ||||  ||   |||  |    |||||
3031 AGTTCACCATCGGCATGGGCGACCTGGAGTTCACTGAGAACTATGACTTC 3080

2215 CGCGGCATGGTGCTGCTGCTGCTGCTGGCCTACGTGCTGCTCACCTACAT 2264
      |   |   |   ||| |  | |||  ||| |  || ||||||||||||
3081 AAGGCTGTCTTCATCATCCTGCTGCTGGCCTATGTAATTCTCACCTACAT 3130

2265 CCTGCTGCTCAACATGCTCATCGCCCTCATGAGCGAGACCGTCAACAGTG 2314
     |||  ||||||||||||||||||||||||||   |||| |||||| |||
3131 CCTCCTGCTCAACATGCTCATCGCCCTCATGGGTGAGACTGTCAACAAGA 3180
```

Fig. 6E

```
2315 TCGCCACTGACAGCTGGAGCATCTGGAAGCTGCAGARAGCCATCTCTGTC 2364
     ||||  || |||  || |||||||||||||||||| |||||||  |  ||
3181 TCGCACAGGAGAGCAAGAACATCTGGAAGCTGCAGAGAGCCATCACCATC 3230

2365 CTGGAGATGGAGAATGGCTATTGGTGGTGCAGGAAGAAG...CAGCGGGC 2411
     ||||| | ||||||  |||        |||||  || ||||    || |
3231 CTGGACACGGAGAAGAGCTTCCTTAAGTGCATGAGGAAGGCCTTCCGCTC 3280

2412 AGGTGTGATGCTGACCGTTGGCACTAAGCCAGATGGCAGCCCGGATGAGC 2461
     |||   | |||||    || ||    |  || |||||||    || | |
3281 AGGCAAGCTGCTGCAGGTGGGGTACACACCTGATGGCAAGGACGACTACC 3330

2462 GCTGGTGCTTCAGGGTGGAGGAGGTGAACTGGGCTTCATGGGAGCAGACG 2511
     | |||||||||||||||||| |||||||||||   | ||| |    |  |
3331 GGTGGTGCTTCAGGGTGGACGAGGTGAACTGGACCACCTGGAACACCAAC 3380

2512 CTGCCTACGCTGTGTGAGGACCCG...TCAGGGGCAGGTGTCCCTCGAAC 2558
     ||   |  |  || ||||||   |     | | |||   || ||  |||
3381 GTGGGCATCATCAACGAAGACCCGGGCAACTGTGAGGCGTCAAGCGCAC 3430

2559 TCTCGAGAACCCTGTCCTG....GCTTCCCCTCCCAAGGAGGATGAGGAT 2604
     ||     | | | |||   ||     ||    ||    ||   ||
3431 CCTGAGCTTCTCCCTGCGGTCAAGCAGAGTTTCAGGCAGACACTGGAAGA 3480

2605 GGTGCCTCTGAGGAAAACTATGTGCCCGTCCAGCTCCTCCAGTCCAACTG 2654
       |   |   |   ||  |       ||  |||  |  | ||| ||  ||
3481 ACTTTGCCCTGGTCCCCCTTTTAAGAGAGGCAAGTGCTCGAGATAGGCAG 3530

2655 ATGGCCCAGATGCAGCAGGAGGCCAGAGGACAGAGCAGAGGATCTTTCCA 2704
        || |||   || | |         |||||    ||| ||| ||     |
3531 TCTGCTCAGCCCGAGGAAGTTTATCTGCGACAGTTTTCAGGGTCTCTGAA 3580

2705 ACCACATCTGCTGGCTCTGGGGTCCCAGTGAATTCTGGTGGCAAATATAT 2754
     |||      |  | |||  ||||      || | |||  |
3581 GCCA.....GAGGACGCTGAGGTCTTCAAGAGTCCTGCCGCTTCCGGGGA 3625

2755 ATTTTCACTAACTCAAAAAAAAAAAAAAAAAAAAAAAAAAAAAAAAAAAA 2804
     |  |   |||   |||   |    ||           | ||
3626 GAAGTGAGGACGTCACGCAGACAGCACTGTCAACACTGGGCCTTAGGAGA 3675

2805 AAAAA.......................................... 2809

3676 CCCCGTTGCCACGGGGGGCTGCTGAGGGAACACCAGTGCTCTGTCAGCAG 3725
                              .
                              .
```

Fig. 6F

CLUSTAL W (1.74) multiple sequence alignment

```
humanVR2    MTSPSSSPVFRLETLDGGQEDGSEADRGKLDFGSGLPPMESQFQGEDRKFAPQIRVNLNY
rat VR2     ------------------------------------------------------------ humanVR2    RKGTGASQPDPNRFDRDRLFNAVSRGVPEDLAGLPEYLSKTSKYLTDSEYTEGSTGKTCL
rat VR2     ------------------------------------------------------------ humanVR2    MKAVLNLKDGVNACILPLLQIDRDSGNPQPLVNAQCTDDYYRGHSALHIAIEKRSLQCVK
rat VR2     ------------------------------------------------------------ humanVR2    LLVENGANVHARACGRFFQKGQGTCFYFGELPLSLAACTKQWDVVSYLLENPHQPASLQA
rat VR2     ---------------------------STHASALSLAACTKQWDVVTYLLENPHQPASLEA
                                       .***********:**********:* humanVR2    TDSQGNTVLHALVMISDNSAENIALVTSMYDGLLQAGARLCPTVQLEDIRNLQDLTPLKL
rat VR2     TDSLGNTVLHALVMIADNSPENSALVIHMYDGLLQMGARLCPTVQLEEISNHQGLTPLKL
            * *******.*. * **** *********:* * *.****** humanVR2    AAKEGKIEIFRHILQREFSG-LSHLSRKFTEWCYGPVRVSLYDLASVDSCEENSVLEIIA
rat VR2     AAKEGKIEIFRHILQREFSGPYQPLSRKFTEWCYGPVRVSLYDLSSVDSWEKNSVLEIIA
            ******************  . ****************:** *:******** humanVR2    FHCKSPHRHRMVVLEPLNKLLQAKWDLLIPKFFLNFLCNLIYMFIFTAVAYHQPTLKKQA
rat VR2     FHCKSPNRHRMVVLEPLNKLLQEKWDRLVSRFFFNFACYLVYMFIPTVVAYHQPSLDQPA
            ****:**********  *  :.::* * :.****.*.******.*.: * humanVR2    APHLKAEVGNSMLLTGHILILLGGIYLLVGQLWYFWRRHVFIWISFIDSYFEILFLFQAL
rat VR2     IPSSKATFGESMLLLGHILILLGGIYLLLGQLWYFWRRRLFIWISFMDSYFEILFLLQAL
            *  :.*:.*:**.********* ***** :**:****:* humanVR2    LTVVSQVLCFLAIEWYLPLLVSALVLGWLNLLYYTRGFQHIGIYSVMIQKVILRDLLRFL
rat VR2     LTVLSQVLRFMETEWYLPLLVLSLVLGWLNLLYYTRGFQHTGIYSVMIQKVILRDLLRFL
            *:** *:  ****** :*************.***************** humanVR2    LIYLVFLFGFAVALVSLSQEAWRPEAPTGPNATESVQPMEGQEDEGNGAQYRGILEASLE
rat VR2     LVYLVFLFGFAVALVSLSREARSPKAPEDNNSTVTEQPTVGQEEEP--APYRSILDASLE
            *:**************.:. :.**  * :: ** *..***:*     .:**** humanVR2    LFKFTIGMGELAFQEQLHFRGMVLLLLLAYVLLTYILLLNMLIALMSETVNSVATDSWSI
rat VR2     LFKFTIGMGELAFQEQLRFRGVVLLLLLAYVLLTYVLLLNMLIALMSETVNHVADNSWSI
            ***************::*:************:********* :.**** humanVR2    WKLQKAISVLEMENGYWWCR-KKQRAGVMLTVGTKPDGSPDERWCFRVEEVNWASWEQTL
rat VR2     WKLQKAISVLEMENGYWWCRRKKHREGRLLKVGTRGDGTPDERWCFRVEEVNKAAWEKTL
            ******************* **:* * :* ***:.** *************.:.**:**

humanVR2    PTLCEDPSGAGVPRTLENPVLASPPKEDEDGASEENYVPVQLLQSN
rat VR2     PTLSEDPSGPGITGNKKNPTSK-PGK---NSASEEDHLPLQVLQSP
            ***.*****.*:. .  :**. . *.   :.****:::*:*:****
```

Fig. 7

GAP of: ratvr2.pep check: 9190 from: 1 to: 554 ratVR2 Flrxb147g11 to: humanvr2.pep check: 5746 from: 1 to: 764 humanVR2 Flh21e11

Symbol comparison table: /usr/local/gog_9.1/gcgcore/data/rundata/blosum62.cmp
CompCheck: 6430

| Gap Weight: | 12 | Average Match: | 2.912 |
|---|---|---|---|
| Length Weight: | 4 | Average Mismatch: | -2.003 |
| Quality: | 2182 | Length: | 766 |
| Ratio: | 3.939 | Gaps: | 4 |
| Percent Similarity: | 81.703 | Percent Identity: | 79.167 |

Match display thresholds for the alignment(s) :
```
        | = IDENTITY
        : = 2
        . = 1
``` ratvr2.pep x humanvr2.pep

```
  1 ......STHASALSLAACTKQWDVVTYLLENPHQPASLEATDSLGNTVLH  44
        ||||||||||||-|||||||||||:||| ||||||
201 GQGTCFYFGELPLSLAACTKQWDVVSYLLENPHQPASLQATDSQGNTVLH 250

45 ALVMIADNSPENSALVIHMYDGLLQMGARLCPTVQLEEISNHQGLTPLKL  94
    |||||-||| || |||  ||||||| |||||||||||:| | | ||||||
251 ALVMISDNSAENIALVTSMYDGLLQAGARLCPTVQLEDIRNLQDLTPLKL 300

95 AAKEGKIEIFRHILQREFSGPYQPLSRKFTEWCYGPVRVSLYDLSSVDSW 144
    ||||||||||||||||||||    |||||||||||||||||||-||||
301 AAKEGKIEIFRHILQREFSG.LSHLSRKFTEWCYGPVRVSLYDLASVDSC 349

145 EKNSVLEIIAFHCKSPNRHRMVVLEPLNKLLQEKWDRLVSRPFFNFACYL 194
    |-|||||||||||||-|||||||||||||| ||| |: :|| || | |
350 EENSVLEIIAFHCKSPHRHRMVVLEPLNKLLQAKWDLLIPKFFLNFLCNL 399

195 VYMFIFTVVAYHQPSLDQPAIPSSKATFGESMLLLGHILILLGGIYLLLG 244
    :||||||  ||||||-| - || ||  |  |||| |||||||||||||-|
400 IYMFIFTAVAYHQPTLKKQAAPHLKAEVGNSMLLTGHILILLGGIYLLVG 449
```

Fig. 8A

```
245 QLWYFWRRRLFIWISFMDSYFEILFLLQALLTVLSQVLRFMETEWYLPLL 294
    ||||||||·||||||·|||||||||| ||||||·|||| |:  |||||||
450 QLWYFWRRHVFIWISFIDSYFEILFLFQALLTVVSQVLCFLAIEWYLPLL 499

295 VLSLVLGWLNLLYYTRGFQHTGIYSVMIQKVILRDLLRFLLVYLVFLFGF 344
    | ·|||||||||||||||||||||||||||||||||||||||:||||||
500 VSALVLGWLNLLYYTRGFQHTGIYSVMIQKVILRDLLRFLLIYLVFLFGF 549

345 AVALVSLSREARSPKAPEDNNSTVTEQPTVGQEEE..PAPYRSILDASLE 392
    |||||||·|| |·||   |·| · ||  |||:|  | || ||:||||
550 AVALVSLSQEAWRPEAPTGPNATESVQPMEGQEDEGNGAQYRGILEASLE 599

393 LFKFTIGMGELAFQEQLRFRGVVLLLLLAYVLLTYVLLLNMLIALMSETV 442
    |||||||||||||||| |||·|||||||||||||:||||||||||||||
600 LFKFTIGMGELAFQEQLHFRGMVLLLLLAYVLLTYILLLNMLIALMSETV 649

443 NHVADNSWSIWKLQKAISVLEMENGYWWCRRKKHREGRLLKVGTRGDGTP 492
    | || ·||||||||||||||||||||| ||| | | :| |||: ||·|
650 NSVATDSWSIWKLQKAISVLEMENGYWWC.RKKQRAGVMLTVGTKPDGSP 698

493 DERWCFRVEEVNWAAWEKTLPTLSEDPSGPGITGNKKNPT....SKPGKN 538
    |||||||||||||·||·||||| ||||| |:   ·||   |  ··
699 DERWCFRVEEVNWASWEQTLPTLCEDPSGAGVPRTLENPVLASPPKEDED 748

539 SASEEDHLPLQVLQSP 554
    ||||·:·|·|·|||
749 GASEENYVPVQLLQSN 764
```

Fig. 8B

GAP of: humanvr1.seq check: 4554 from: 1 to: 3909 humanVR1 Fbh18547pat - Import - complete to: ratvr1.seq check: 7921 from: 1 to: 2847 ratVR1.seq AF029310 in GenBank

Symbol comparison table:
/ddm_local/gcg/gcg_9.1/gcgcore/data/rundata/nwsgapdna.cmp
CompCheck: 8760

```
        Gap Weight:    50      Average Match:    10.000
     Length Weight:     3      Average Mismatch:  0.000

Quality:  22717             Length:    3914
             Ratio:  7.979               Gaps:      10
Percent Similarity: 82.125    Percent Identity:  82.125
```

Match display thresholds for the alignment(s):
| = IDENTITY
: = 5
. = 1 humanvr1 . seq x ratvr1 . seq

```
1001 CCAGGCCGTAGATGCTCCCCGCCGGTCAGTCACTTAGTCGTCAGATCGCC 1050
                                     ||   |    | ||
   1 ........................CAGCTCCAAGGCACTTGCTCC  21

1051 CGTCCTGGTATCACAGTGCTTCTGTTCAGGTTGCACACTGGGCCACAGAG 1100
       |   ||| | | | | |   | ||||||||| | |||||||||||||
  22 ATTTGGGGTGTGCCTGCACCT...AGCTGGTTGCAAATTGGGCCACAGAG  68

1101 GATCCAGCAAGGATGAAGAAATGGAGCAGCACAGACTTGGGGACAGCTGC 1150
     ||||  | ||||||||| || ||   |||| ||     ||   |   |||
  69 GATCTGGAAAGGATGGAACAACGGGCTAGCTTAGACTCAGAGGAGTCTGA 118

1151 GGACCCACTCCAAAAGGACACCTGCCCAGACCCCCTGGATGGAGACCCTA 1200
     |  ||||| |||| || || ||||||  |||||| |  || ||||||||
 119 GTCCCCACCCCAAGAGAACTCCTGCCTGGACCCTCCAGACAGAGACCCTA 168
```

Fig. 9A

```
1201 ACTCCAGGCCACCTCCAGCCAAGCCCCAGCTCCCCACGGCCAAGAGCCGC 1250
     ||| || |||||||||||| |||||||||| ||  ||| ||| ||| ||
 169 ACTGCAAGCCACCTCCAGTCAAGCCCCACATCTTCACTACCAGGAGTCGT 218

1251 ACCCGGCTCTTTGGGAAGGGTGACTCGGAGGAGGCTTTCCCGGTGGATTG 1300
     |||||||| ||||||||||||||||||||||||||| ||  |||| ||
 219 ACCCGGCTTTTTGGGAAGGGTGACTCGGAGGAGGCCTCTCCCCTGGACTG 268

1301 CCCCCACGAGGAAGGTGAGTTGGACTCCTGCCCGACCATCACAGTCAGCC 1350
     |||  | ||||||||   ||| |||||||| ||||||| |||||||
 269 CCCTTATGAGGAAGGCGGGCTGGCTTCCTGCCCTATCATCACTGTCAGCT 318

1351 CTGTTATCACCATCCAGAGGCCAGGAGACGGCCCCACCGGTGCCAGGCTG 1400
     |||||  |  || |||||||| ||||||  |||  || ||||||| |
 319 CTGTTCTAACTATCCAGAGGCCTGGGGATGGACCTGCCAGTGTCAGGCCG 368

1401 CTGTCCCAGGACTCTGTCGCCGCCAGCACCGAGAAGACCCTCAGGCTCTA 1450
     |||||||||| ||| |||| |       |||||| ||| ||||||||
 369 TCATCCCAGGACTCCGTCTCCGCTGG...TGAGAAGCCCCCGAGGCTCTA 415

1451 TGATCGCAGGAGTATCTTTGAAGCCGTTGCTCAGAATAACTGCCAGGATC 1500
     |||||||||||| ||||| || || ||  ||||||| ||||||||||| |
 416 TGATCGCAGGAGCATCTTCGATGCTGTGGCTCAGAGTAACTGCCAGGAGC 465

1501 TGGAGAGCCTGCTGCTCTTCCTGCAGAAGAGCAAGAAGCACCTCACAGAC 1550
     ||||||||||||| |||||||||||| |||||||||||  || || |||
 466 TGGAGAGCCTGCTGCCCTTCCTGCAGAGGAGCAAGAAGCGCCTGACTGAC 515

1551 AACGAGTTCAAAGACCCTGAGACAGGGAAGACCTGTCTGCTGAAAGCCAT 1600
     | |||||||||||||||  |||||||| |||||||||||||| ||||||
 516 AGCGAGTTCAAAGACCCAGAGACAGGAAAGACCTGTCTGCTAAAAGCCAT 565

1601 GCTCAACCTGCACGACGGACAGAACACCACCATCCCCCTGCTCCTGGAGA 1650
     |||||| ||||||| ||||  |||  |||||| || ||||||||||| |
 566 GCTCAATCTGCACAATGGGCAGAATGACACCATCGCTCTGCTCCTGGACG 615

1651 TCGCGCGGCAAACGGACAGCCTGAAGGAGCTTGTCAACGCCAGCTACACG 1700
     | ||  || |  || ||||||||||| || ||||||||||||||||| 
 616 TTGCCCGGAAGACAGACAGCCTGAAGCAGTTTGTCAATGCCAGCTACACA 665

1701 GACAGCTACTACAAGGGCCAGACAGCACTGCACATCGCCATCGAGAGACG 1750
     |||||||||||||||||||||||||||||||||| |||||| ||  | |
 666 GACAGCTACTACAAGGGCCAGACAGCACTGCACATTGCCATTGAACGGCG 715
```

Fig. 9B

```
1751 CAACATGGCCCTGGTGACCCTCCTGGTGGAGAACGGAGCAGACGTCCAGG 1800
     ||||||  | ||||||||||||| ||||||||||| ||||||||  |||||||
 716 GAACATGACGCTGGTGACCCTCTTGGTGGAGAATGGAGCAGATGTCCAGG 765

1801 CTGCGGCCCATGGGGACTTCTTTAAGAAAACCAAAGGGCGGCCTGGATTC 1850
     |||||||  | ||||||||||||| |||||||||||||| ||||||| |||
 766 CTGCGGCTAACGGGGACTTCTTCAAGAAAACCAAAGGGAGGCCTGGCTTC 815

1851 TACTTCGGTGAACTGCCCCTGTCCCTGGCCGCGTGCACCAACCAGCTGGG 1900
     ||||| ||||| ||||||||||||||||| |||||||||||||||||||||
 816 TACTTTGGTGAGCTGCCCCTGTCCCTGGCTGCGTGCACCAACCAGCTGGC 865

1901 CATCGTGAAGTTCCTGCTGCAGAACTCCTGGCAGACGGCCGACATCAGCG 1950
     ||| |||||||||||||||||||||||||||||| | || ||||||||||
 866 CATTGTGAAGTTCCTGCTGCAGAACTCCTGGCAGCCTGCAGACATCAGCG 915

1951 CCAGGGACTCGGTGGGCAACACGGTGCTGCACGCCCTGGTGGAGGTGGCC 2000
     || |||||| ||||||||||||||||||| || |||||||||||||||||
 916 CCCGGGACTCAGTGGGCAACACGGTGCTTCATGCCCTGGTGGAGGTGGCA 965

2001 GACAACACGGCCGACAACACGAAGTTTGTGACGAGCATGTACAATGAGAT 2050
     || ||||||   ||||||| |||| |||||||| |||||||||| |||||
 966 GATAACACAGTTGACAACACCAAGTTCGTGACAAGCATGTACAACGAGAT 1015

2051 TCTGATGCTGGGGGCCAAACTGCACCCGACGCTGAAGCTGGAGGAGCTCA 2100
     |||| ||||||||||||||||  |||| |||||||||||||||  || ||
1016 CTTGATCCTGGGGGCCAAACTCCACCCCACGCTGAAGCTGGAAGAGATCA 1065

2101 CCAACAAGAAGGGAATGACGCCGCTGGCTCTGGCAGCTGGGACCGGGAAG 2150
     |||||| ||||||  | ||||| |||||||||||| ||  | | |||||
1066 CCAACAGGAAGGGGCTCACGCCACTGGCTCTGGCTGCTAGCAGTGGGAAG 1115

2151 ATCGGGGTCTTGGCCTATATTCTCCAGCGGGAGATCCAGGAGCCCGAGTG 2200
     ||||||||||||||||| |||||||||| |||||||| || ||||||||
1116 ATCGGGGTCTTGGCCTACATTCTCCAGAGGGAGATCCATGAACCCGAGTG 1165

2201 CAGGCACCTGTCCAGGAAGTTCACCGAGTGGGCCTACGGGCCCGTGCACT 2250
     | | |||| ||||||||||||||||||  |||||||||  |||||||||
1166 CCGACACCTATCCAGGAAGTTCACCGAATGGGCCTATGGGCCAGTGCACT 1215

2251 CCTCGCTGTACGACCTGTCCTGCATCGACACCTGCGAGAAGAACTCGGTG 2300
     ||||  | ||||||||||||||||| |||||||||| ||||||||||||
1216 CCTCCCTTTATGACCTGTCCTGCATTGACACCTGTGAAAAGAACTCGGTT 1265
```

Fig. 9C

```
2301 CTGGAGGTGATCGCCTACAGCAGCAGCGAGACCCCTAATCGCCACGACAT 2350
     |||||||||||||| ||||||||||| |||||||||| || || |||||
1266 CTGGAGGTGATCGCTTACAGCAGCAGTGAGACCCCTAACCGTCATGACAT 1315

2351 GCTCTTGGTGGAGCCGCTGAACCGACTCCTGCAGGACAAGTGGGACAGAT 2400
     ||| | |||| || |||||||||||||||| ||||||||||||||||||
1316 GCTTCTCGTGGAACCCTTGAACCGACTCCTACAGGACAAGTGGGACAGAT 1365

2401 TCGTCAAGCGCATCTTCTACTTCAACTTCCTGGTCTACTGCCTGTACATG 2450
     | ||||||||||||||||||||||||||| | |||||||||| ||| |||
1366 TTGTCAAGCGCATCTTCTACTTCAACTTCTTCGTCTACTGCTTGTATATG 1415

2451 ATCATCTTCACCATGGCTGCCTACTACAGGCCCGTGGATGGCTTGCCTCC 2500
     |||||||||||  |||||||||||||| ||||||||||  ||||||| ||
1416 ATCATCTTCACCGCGGCTGCCTACTATCGGCCTGTGGAAGGCTTGCCCCC 1465

2501 CTTTAAGATGGAAAAAA...TTGGAGACTATTTCCGAGTTACTGGAGAGA 2547
     || |||| || |||| |    |||| |||||||||||| || |||||||
1466 CTATAAGCTGAAAAACACCGTTGGGGACTATTTCCGAGTCACCGGAGAGA 1515

2548 TCCTGTCTGTGTTAGGAGGAGTCTACTTCTTTTTCCGAGGGATTCAGTAT 2597
     || |||||||| |||||||||||||||||||||| ||||||||||| |||
1516 TCTTGTCTGTGTCAGGAGGAGTCTACTTCTTCTTCCGAGGGATTCAATAT 1565

2598 TTCCTGCAGAGGCGGCCGTCGATGAAGACCCTGTTTGTGGACAGCTACAG 2647
     |||||||||||| || || | |||| |||||||||||||||||||||||
1566 TTCCTGCAGAGGCGACCATCCCTCAAGAGTTTGTTTGTGGACAGCTACAG 1615

2648 TGAGATGCTTTTCTTTCTGCAGTCACTGTTCATGCTGGCCACCGTGGTGC 2697
     |||||| |||||||||| || | |||||||||||||||  | |||||| |
1616 TGAGATACTTTTCTTTGTACAGTCGCTGTTCATGCTGGTGTCTGTGGTAC 1665

2698 TGTACTTCAGCCACCTCAAGGAGTATGTGGCTTCCATGGTATTCTCCCTG 2747
     |||||||||||| | |||||||||||||||||||||||||| ||||||||
1666 TGTACTTCAGCCAACGCAAGGAGTATGTGGCTTCCATGGTGTTCTCCCTG 1715

2748 GCCTTGGGCTGGACCAACATGCTCTACTACACCCGCGGTTTCCAGCAGAT 2797
     ||| ||||||||||||||||||||||||| |||| || ||||||||||||
1716 GCCATGGGCTGGACCAACATGCTCTACTATACCCGAGGATTCCAGCAGAT 1765

2798 GGGCATCTATGCCGTCATGATAGAGAAGATGATCCTGAGAGACCTGTGCC 2847
     |||||||||||| ||||||||| ||||||||||||||||||||||||||
1766 GGGCATCTATGCTGTCATGATTGAGAAGATGATCCTCAGAGACCTGTGCC 1815
```

Fig. 9D

```
2848 GTTTCATGTTTGTCTACATCGTCTTCTTGTTCGGGTTTTCCACAGCGGTG 2897
     | || ||||| ||||| |||| |||||||| || |||||||||| |||
1816 GGTTTATGTTCGTCTACCTCGTGTTCTTGTTTGGATTTTCCACAGCTGTG 1865

2898 GTGACGCTGATTGAAGACGGGAAGAATGACTCCCTGCCGTCTGAGTCCAC 2947
     |||| |||||||| || ||||||||| |||| |||||   |||||||||
1866 GTGACACTGATTGAGGATGGGAAGAATAACTCTCTGCCTATGGAGTCCAC 1915

2948 GTCGCACAGGTGGCGGGGGCCTGCCTGCAGGCCCCCCGATAGCTCCTACA 2997
      | |||| ||| |||||| |||||||| |  ||| || ||| ||||
1916 ACCACACAAGTGCCGGGGGTCTGCCTGCAAG...CCAGGTAACTCTTACA 1962

2998 ACAGCCTGTACTCCACCTGCCTGGAGCTGTTCAAGTTCACCATCGGCATG 3047
     ||||||||| ||||| || |||||||||||||||||||||||||||||||
1963 ACAGCCTGTATTCCACATGTCTGGAGCTGTTCAAGTTCACCATCGGCATG 2012

3048 GGCGACCTGGAGTTCACTGAGAACTATGACTTCAAGGCTGTCTTCATCAT 3097
     ||||||||||||||||||||||||| ||||||||||||||||||||||||
2013 GGCGACCTGGAGTTCACTGAGAACTACGACTTCAAGGCTGTCTTCATCAT 2062

3098 CCTGCTGCTGGCCTATGTAATTCTCACCTACATCCTCCTGCTCAACATGC 3147
     |||| | |||||||||||| |||||||||||||||| |||||||||||||
2063 CCTGTTACTGGCCTATGTGATTCTCACCTACATCCTTCTGCTCAACATGC 2112

3148 TCATCGCCCTCATGGGTGAGACTGTCAACAAGATCGCACAGGAGAGCAAG 3197
     |||| || ||||||||||||||| |||||||||| |||| ||||||||||
2113 TCATTGCTCTCATGGGTGAGACCGTCAACAAGATTGCACAAGAGAGCAAG 2162

3198 AACATCTGGAAGCTGCAGAGAGCCATCACCATCCTGGACACGGAGAAGAG 3247
     |||||||||||||||||||||||||||||||||||||| || ||||||||
2163 AACATCTGGAAGCTGCAGAGAGCCATCACCATCCTGGATACAGAGAAGAG 2212

3248 CTTCCTTAAGTGCATGAGGAAGGCCTTCCGCTCAGGCAAGCTGCTGCAGG 3297
     |||||| ||||||||||||||||||||||||| |||||||||||||||||
2213 CTTCCTGAAGTGCATGAGGAAGGCCTTCCGCTCTGGCAAGCTGCTGCAGG 2262

3298 TGGGGTACACACCTGATGGCAAGGACGACTACCGGTGGTGCTTCAGGGTG 3347
     |||||| ||| ||||| ||||||||| ||||||||||||| ||||||||
2263 TGGGGTTCACTCCTGACGGCAAGGATGACTACCGGTGGTGTTTCAGGGTG 2312

3348 GACGAGGTGAACTGGACCACCTGGAACACCAACGTGGGCATCATCAACGA 3397
     ||||||||  ||||||||  ||||||||||||| ||||| ||||||||||
2313 GACGAGGTAAACTGGACTACCTGGAACACCAATGTGGGTATCATCAACGA 2362
```

Fig. 9E

```
3398 AGACCCGGGCAACTGTGAGGGCGTCAAGCGCACCCTGAGCTTCTCCCTGC 3447
     |||||  |||||||||||||||||||||||||||||||||||||||||||
2363 GGACCCAGGCAACTGTGAGGGCGTCAAGCGCACCCTGAGCTTCTCCCTGA 2412

3448 GGTCAAGCAGAGTTTCAGGCAGACACTGGAAGAACTTTGCCCTGGTCCCC 3497
     ||||| || ||||||||||  ||| |||||||||||||||||||| |||
2413 GGTCAGGCCGAGTTTCAGGGAGAAACTGGAAGAACTTTGCCCTGGTTCCC 2462

3498 CTTTTAAGAGAGGCAAGTGCTCGAGATAGGCAGTCTGCTCAGCCCGAGGA 3547
     ||| | || || ||||| ||||||||||| ||  | |||| || || ||
2463 CTTCTGAGGGATGCAAGCACTCGAGATAGACATGCCACCCAGCAGGAAGA 2512

3548 AGTTTATCTGCGACAGTTTTCAGGGTCTCTGAAGCCAGAGGACGCTGAGG 3597
     |||| | |||  || | | || || |||||||||||||||| |||||||
2513 AGTTCAACTGAAGCATTATACGGGATCCCTTAAGCCAGAGGATGCTGAGG 2562

3598 TCTTCAAGAGTCCTGCCGCTTCCGGGGAGAAGTGA.GGACGTCACGCAGA 3646
     | ||||||  ||    |   | |||||||| | ||||    |   ||||
2563 TTTTCAAGGATTCCATGGTCCCAGGGGAGAAATAATGGACACTATGCAGG 2612

3647 CAGCACTGTCAACACTGGGCCTTAGGAGACCCCGTTGCCACGGGGGGCTG 3696
     | || ||               |||         |||    || || ||
2613 GATCAATG.....................CGGGGTCTTTGGGTGGTCTG 2640

3697 CTGAGGGAACACCAGTGCTCTGTCAGCAGCCTGGCCTGGTCTGTGCCTGC 3746
     || |||||||  |||||| ||  |  || ||  |  | |||||||||||
2641 CTTAGGGAAC.CAGCAGGGTTGACGTTATCTGGGTCCACTCTGTGCCTGC 2689

3747 CCA.GCATGTTCCCAAATCTGTGCTGGACAAGCTGTGGGAAGCGTTCTTG 3795
     | | |||  ||||  ||  |  ||| ||||||||||||||| |     |
2690 CTAGGCACATTCCTAGGACTTCGGCGGGCCTGCTGTGGGAA.CTGGGAGG 2738

3796 GAAGCATGGGGAGTGATGTACATCCAACCGTCACTGTCCCCAAGTGAATC 3845
      |  |   ||||||  ||||||||| ||  ||  ||    || | |  |
2739 TGTGTGGGAATTGAGATGTGTATCCAACCATGA...TCTCCAAACATTTG 2785

3846 TCCTAACAGACTTTCAGGTTTTTACTCACTTTACTAAAAAAAAAAAAAAA 3895
     || |  |  ||||| || || ||| |  ||  | | ||         |||
2786 GCTTTCAACTCTTTATGGACTTTATTAAACAGAGTGAATGGCAAATCTCT 2835

3896 AGGGCGGCCGCTTA 3909
       |    ||| |
2836 ACTTGGACACAT.. 2847
```

Fig. 9F

GAP of: humanvr1.pep check: 6877 from: 1 to: 839 humanVR1_Fbh18547pat - fchrb87a6, 3909 bases, 4554 checksum.

to: ratvr1.pep check: 5764 from: 1 to: 838 ratVR1 | AF029310 Rattus norvegicus vanilloid receptor subtype 1 mRNA, complete cds.

Symbol comparison table:
/ddm_local/gcg/gcg_9.1/gcgcore/data/rundata/blosum62.cmp
CompCheck: 6430

```
         Gap Weight:     12        Average Match:     2.912
      Length Weight:      4        Average Mismatch: -2.003

Quality:   3734               Length:      840
              Ratio:  4.456                 Gaps:        3
  Percent Similarity: 89.247     Percent Identity:   86.022
```

Match display thresholds for the alignment(s):
　　　| = IDENTITY
　　　: = 2
　　　. = 1
humanvr1.pep x ratvr1.pep

```
  1 MKKWSSTDLGTAADPLQKDTCPDPLDGDPNSRPPPAKPQLPTAKSRTRLF 50
    |.. .| |   . | |...|.||.|.|||.:||| ||  : | :||||||
  1 MEQRASLDSEESESPPQENSCLDPPDRDPNCKPPPVKPHIFTTRSRTRLF 50

51 GKGDSEEAFPVDCPHEEGELDSCPTITVSPVITIQRPGDGPTGARLLSQD 100
    ||||||| |.|||:||| | ||| |||| |:||||||||| |   |||
 51 GKGDSEEASPLDCPYEEGGLASCPIITVSSVLTIQRPGDGPASVRPSSQD 100

101 SVAASTEKTLRLYDRRSIFEAVAQNNCQDLESLLLFLQKSKKHLTDNEFK 150
    ||.| ||  ||||||||||:||||.|||:||||| |||:||| |||.|||
101 SVSAG.EKPPRLYDRRSIFDAVAQSNCQELESLLPFLQRSKKRLTDSEFK 149

151 DPETGKTCLLKAMLNLHDGQNTTIPLLLEIARQTDSLKELVNASYTDSYY 200
    ||||||||||||||||.||| || |||::||.|||||: ||||||||||
150 DPETGKTCLLKAMLNLHNGQNDTIALLLDVARKTDSLKQFVNASYTDSYY 199

201 KGQTALHIAIERRNMALVTLLVENGADVQAAAHGDFFKKTGRPGFYFGE 250
    |||||||||||||| |||||||||||||||||.|||||||||||||||
200 KGQTALHIAIERRNMTLVTLLVENGADVQAAANGDFFKKTGRPGFYFGE 249
```

Fig. 10A

```
251 LPLSLAACTNQLGIVKFLLQNSWQTADISARDSVGNTVLHALVEVADNTA 300
    |||||||||||| ||||||||||| |||||||||||||||||||||||
250 LPLSLAACTNQLAIVKFLLQNSWQPADISARDSVGNTVLHALVEVADNTV 299

301 DNTKFVTSMYNEILMLGAKLHPTLKLEELTNKKGMTPLALAAGTGKIGVL 350
    |||||||||||||·|||||||||||||:||:||:|||||||·||||||
300 DNTKFVTSMYNEILILGAKLHPTLKLEEITNRKGLTPLALAASSGKIGVL 349

351 AYILQREIQEPECRHLSRKFTEWAYGPVHSSLYDLSCIDTCEKNSVLEVI 400
    ||||||| |||||||||||||||||||||||||||||||||||||||||
350 AYILQREIHEPECRHLSRKFTEWAYGPVHSSLYDLSCIDTCEKNSVLEVI 399

401 AYSSSETPNRHDMLLVEPLNRLLQDKWDRFVKRIFYFNFLVYCLYMIIFT 450
    |||||||||||||||||||||||||||||||||||||| |||||||||
400 AYSSSETPNRHDMLLVEPLNRLLQDKWDRFVKRIFYFNFFVYCLYMIIFT 449

451 MAAYYRPVDGLPPFKMEK.IGDYFRVTGEILSVLGGVYFFFRGIQYFLQR 499
    |||||:||||:|||:·  :||||||||||||||  ||||||||||||||
450 AAAYYRPVEGLPPYKLKNTVGDYFRVTGEILSVSGGVYFFFRGIQYFLQR 499

500 RPSMKTLFVDSYSEMLFFLQSLFMLATVVLYFSHLKEYVASMVFSLALGW 549
    |||:|·|||||||||·|||·||||||·||||||   ||||||||||||:||
500 RPSLKSLFVDSYSEILFFVQSLFMLVSVVLYFSQRKEYVASMVFSLAMGW 549

550 TNMLYYTRGFQQMGIYAVMIEKMILRDLCRFMFVYIVFLFGFSTAVVTLI 599
    |||||||||||||||||||||||||||||||||||:|||||||||||||
550 TNMLYYTRGFQQMGIYAVMIEKMILRDLCRFMFVYLVFLFGFSTAVVTLI 599

600 EDGKNDSLPSESTSHRWRGPACRPPDSSYNSLYSTCLELFKFTIGMGDLE 649
    |||||·||| ||| |: || ||: |  ·|||||||||||||||||||||
600 EDGKNNSLPMESTPHKCRGSACK.PGNSYNSLYSTCLELFKFTIGMGDLE 648

650 FTENYDFKAVFIILLLAYVILTYILLLNMLIALMGETVNKIAQESKNIWK 699
    |||||||||||||||||||||||||||||||||||||||||||||||||
649 FTENYDFKAVFIILLLAYVILTYILLLNMLIALMGETVNKIAQESKNIWK 698

700 LQRAITILDTEKSFLKCMRKAFRSGKLLQVGYTPDGKDDYRWCFRVDEVN 749
    |||||||||||||||||||||||||||||||:|||||||||||||||||
699 LQRAITILDTEKSFLKCMRKAFRSGKLLQVGFTPDGKDDYRWCFRVDEVN 748

750 WTTWNTNVGIINEDPGNCEGVKRTLSFSLRSSRVSGRHWKNFALVPLLRE 799
    ||||||||||||||||||||||||||||||| |||||·|||||||||||:
749 WTTWNTNVGIINEDPGNCEGVKRTLSFSLRSGRVSGRNWKNFALVPLLRD 798

800 ASARDRQSAQPEEVYLRQFSGSLKPEDAEVFKSPAASGEK 839
    || |||·|  | ||| |:·:·|||||||||||   |||
799 ASTRDRHATQQEEVQLKHYTGSLKPEDAEVFKDSMVPGEK 838
```

Fig. 10B

CLUSTAL W (1.74) multiple sequence alignment

```
humanVR2.alt    ------------------------------------------------------------
human VR2       MTSPSSSPVFRLETLDGGQEDGSEADRGKLDFGSGLPPMESQFQGEDRKFAPQIRVNLNY humanVR2.alt    ------------------------------------------------------------
human VR2       RKGTGASQPDPNRFDRDRLFNAVSRGVPEDLAGLPEYLSKTSKYLTDSEYTEGSTGKTCL humanVR2.alt    ------------------------------------------------------------
human VR2       MKAVLNLKDGVNACILPLLQIDRDSGNPQPLVNAQCTDDYYRGHSALHIAIEKRSLQCVK humanVR2.alt    --------------GRFFQKGQGTCFYFGELPLSLAACTKQWDVVSYLLENPHQPASLQA
human VR2       LLVENGANVHARACGRFFQKGQGTCFYFGELPLSLAACTKQWDVVSYLLENPHQPASLQA
                              ********************************************** humanVR2.alt    TDSQGNTVLHALVMISDNSAENIALVTSMYDGLLQAGARLCPTVQLEDIRNLQDLTPLKL
human VR2       TDSQGNTVLHALVMISDNSAENIALVTSMYDGLLQAGARLCPTVQLEDIRNLQDLTPLKL
                ************************************************************ humanVR2.alt    AAKEGKIEIFRHILQREFSGLSHLSRKFTEWCYGPVRVSLYDLASVDSCEENSVLEIIAF
human VR2       AAKEGKIEIFRHILQREFSGLSHLSRKFTEWCYGPVRVSLYDLASVDSCEENSVLEIIAF
                ************************************************************ humanVR2.alt    HCKSPHRHRMVVLEPLNKLLQAKWDLLIPKFFDNFLCNLIYMFIFTAVAYHQPTLKKQAA
human VR2       HCKSPHRHRMVVLEPLNKLLQAKWDLLIPKFFLNFLCNLIYMFIFTAVAYHQPTLKKQAA
                ****************************** ************************* humanVR2.alt    PHLKAEVGNSMLLTGHILILLGGIYLLVGQLWYFWRRHVFIWISFIDSYFEILFLFQALL
human VR2       PHLKAEVGNSMLLTGHYLILLGGIYLLVGQLWYFWRRHVFIWISFIDSYFEILFLFQALL
                ************** ***************************************** humanVR2.alt    TVVSQVLCFLAIEWYLPLLVSALVLGWLNLLYYTRGFQHTGIYSVMIQ------------
human VR2       TVVSQVLCFLAIEWYLPLLVSALVLGWLNLLYYTRGFQHTGIYSVMIQKVILRDLLRFLL
                *********************************************** humanVR2.alt    ------------------------------------------------------------
human VR2       IYLVFLFGFAVALVSLSQEAWRPEAPTGPNATESVQPMEGQEDEGNGAQYRGILEASLEL humanVR2.alt    ------------------------------------------------------------
human VR2       FKFTIGMGELAFQEQLHFRGMVLLLLLAYVLLTYILLLNMLIALMSETVMSVATDSWSIW humanVR2.alt    --KKAISVLEMENGYWWCRKKQRAGVMLTVGTKPDGSPDERWCFRVEEVNWASWEQTLPT
human VR2       KLQKAISVLEMENGYWWCRKKQRAGVMLTVGTKPDGSPDERWCFRVEEVNWASWEQTLPT
                  ********************************************************** humanVR2.alt    LCEDPSGAGVPRTLENPVLASPPKEDEDGASEENYVPVQLLQSN
human VR2       LCEDPSGAGVPRTLENPVLASPPKEDEDGASEENYVPVQLLQSN
                *******************************************
```

Fig. 11

Protein Family / Domain Matches, HMMer version 2

```
Searching for complete domains
hmmpfam - search a single seq against HMM database
HMMER 2.1.1 (Dec 1998)
Copyright (C) 1992-1998 Washington University School of Medicine
HMMER is freely distributed under the GNU General Public License (GPL).
-----------------------------------------------------------------
HMM file:          /prod/ddm/seqanal/PFAM/pfam4.2/Pfam
Sequence file:     /usr/ns-home/docs/seqanal/orfanal/oa-script 18670 seq
-----------------------------------------------------------------
Query: hVR-1

Scores for sequence family classification (score includes all domains):
Model    Description                                  Score    E-value    N
-------  -----------                                  -----    -------    ---
ank      Ank repeat                                   51.5     1.9e-11    3

Parsed for domains:
Model    Domain   seq-f   seq-t   hmm-f   hmm-t        score    E-value
-------  ------   -----   -----   -----   -----        -----    -------
ank      1/3      201     233 ..  1       33 []        34.4     2.6e-06
ank      2/3      248     283 ..  1       33 []        13.2     2
ank      3/3      333     361 ..  1       33 []        3.4      26

Alignments of top-scoring domains:
ank: domain 1 of 3, from 201 to 233: score 34.4, E = 2.6e-06
               *->nGnTPLHlAarygnvevvklLLehGAdvnartk<-*
                  +G+T+LH+A + n+ +v lL+e+GAdv a+ hVR-1    201   KGQTALHIAIERRNMALVTLLVENGADVQAAAH   233 ank: domain 2 of 3, from 248 to 283: score 13.2, E = 2
               *->nGnTPLHlAarygnvevvklLLe...hGAdvnartk<-*
                  G  PL lAa ++++ +vk+LL+++ + Ad+ ar+
   hVR-1    248   FGELPLSLAACTNQLGIVKFLLQnswQTADISARDS   283 ank: domain 3 of 3, from 333 to 361: score 3.4, E = 26
               *->nGnTPLHlAarygnvevvklLLehGAdvnartk<-*
                  +G TPL lAa +g++ v ++ L+        ++
   hVR-1    333   KGMTPLALAAGTGKIGVLAYILQ----REIQEP   361
```

Fig. 13

Protein Family / Domain Matches, HMMer version 2

```
Searching for complete domains
hmmpfam - search a single seq against HMM database
HMMER 2.1.1 (Dec 1998)
Copyright (C) 1992-1998 Washington University School of Medicine
HMMER is freely distributed under the GNU General Public License (GPL).
--------------------------------------------------------------------
HMM file:              /prod/ddm/seqanal/PFAM/pfam4.2/Pfam
Sequence file:         /tmp/orfanal.5/g.aa
--------------------------------------------------------------------
Query: Flh21e11

Scores for sequence family classification (score includes all domains):
Model    Description                                Score      E-value    N
-------- -----------                                -----      --------   ---
ank      PF00023 Ank repeat                         53.7       4e-12      3

Parsed for domains:
Model   Domain   seq-f  seq-t   hmm-f   hmm-t       score    E-value
------  -------  -----  -----   -----   -----       -----    --------
ank     1/3      162    194 ..  1       33    []    38.3     1.7e-07
ank     2/3      208    243 ..  1       33    []    6.4      4.3
ank     3/3      293    328 ..  1       33    []    8.8      2.1

Alignments of top-scoring domains:
ank: domain 1 of 3,  from 162 to 194: score 38.3, E = 1.7e-07
                   *->nGnTPLHlAarygnvevvklLLehGAdvnartk<-*
                      +G+++LH+A ++ ++++vklL+e+GA+v+ar
       Flh21e11  162  RGHSALHIAIEKRSLQCVKLLVENGANVHARAC       194 ank: domain 2 of 3, from 208 to 243: score 6.4, E = 4.3
                   *->nGnTPLHlAarygnvavvklLLe...hGAdvnartk<-*
                      G  PL lAa +  +++vv +LLe++++ A+   a++
       Flh21e11  208     FGELPLSLAACTKQWDVVSYGLEnphQPASLQATDS    243 ank:  domain 3 of 3, from 293 to 328: score 8.8, E = 2.1
                   *->nGnTPLHLAarygnvevvklLLe...hGAdvnart<<-*
                      +  +TPL lAa++g++e+ +  L+++  G +   +r
       Flh21e11  293     QDLTPLKLAAKEQKLEIFRHILQrafSGLSHLSRK       328
```

Fig. 15

>hvR2.altFL (full-length predicted)
MTSPSSSPVFRLETLDGGQEDGSEADRGKLDFGSGLPPPMESQFQGEDRKFAPQIRVNLNY
RKGTGASQPDPNRFDRDRLFNAVSRGVPEDLAGLPEYLSKTSKYLTDSEYTEGSTGKTCL
MKAVLNLKDGVNACILPLLQIDRDSGNPQPLVNAQCTDDYYRGHSALHIAIEKRSLQCVK
LLVENGANVHARACGRFFQKGQGTCFYFGELPLSLAACTKQWDVVSYLLENPHQPASLQATSQGNTVLHALVM
ISDNSAENIALVTSMYDGLLQAGARLCPTVQLEDIRNLQDLTPLKLAAKEGKIEIFRHIL
QREFSGLSHLSRKFTEWCYGPVRVSLYDLASVDSCEENSVLEIIAFHCKSPHRHRMVVLE
PLNKLLQAKWDLLIPKFFLNFLCNLIYMFIFTAVAYHQPTLKKQAAPHLKAEVGNSMLLT
GHILILLGGIYLLVGQLWYFWRRHVFIWISFIDSYFEILFLFQALLTVVSQVLCFLAIEW
YLPLLVSALVLGWLNLLYYTRGFQHTGIYSVMIQKKAISVLEMENGYWCRKKQRAGVML
TVGTKPDGSPDERWCFRVEEVNWASWEQTLPTLCEDPSGAGVPRTLENPVLASPPKEDED
GASEENYVPVQLLQSN

Fig. 16

CLUSTAL W (1.74) multiple sequence alignment

```
humanVR2    MTSPSSSPVFRLETLDGGQEDGSEADRGKLDFGSGLPPMESQFQGEDRKFAPQIRVNLNY
hVR2.altFL  MTSPSSSPVFRLETLDGGQEDGSEADRGKLDFGSGLPPMESQFQGEDRKFAPQIRVNLNY
            ************************************************************ humanVR2    RKGTGASQPDPNRFDRDRLFNAVSRGVPEDLAGLPEYLSKTSKYLTDSEYTEGSTGKTCL
hVR2.altFL  RKGTGASQPDPNRFDRDRLFNAVSRGVPEDLAGLPEYLSKTSKYLTDSEYTEGSTGKTCL
            ************************************************************ humanVR2    MKAVLNLKDGVNACILPLLQIDRDSGNPQPLVNAQCTDDYYRGHSALHIAIEKRSLQCVK
hVR2.altFL  MKAVLNLKDGVNACILPLLQIDRDSGNPQPLVNAQCTDDYYRGHSALHIAIEKRSLQCVK
            ************************************************************ humanVR2    LLVENGANVHARACGRFFQKGQGTCFYFGELPLSLAACTKQWDVVSYLLENPHQPASLQA
hVR2.altFL  LLVENGANVHARACGRFFQKGQGTCFYFGELPLSLAACTKQWDVVSYLLENPHQPASLQA
            ************************************************************ humanVR2    TDSQGNTVLHALVMISDNSAENIALVTSMYDGLLQAGARLCPTVQLEDIRNLQDLTPLKL
hVR2.altFL  TDSQGNTVLHALVMISDNSAENIALVTSMYDGLLQAGARLCPTVQLEDIRNLQDLTPLKL
            ************************************************************ humanVR2    AAKEGKIEIFRHILQREFSGLSHLSRKFTEWCYGPVRVSLYDLASVDSCEENSVLEIIAF
hVR2.altFL  AAKEGKIEIFRHILQREFSGLSHLSRKFTEWCYGPVRVSLYDLASVDSCEENSVLEIIAF
            ************************************************************ humanVR2    HCKSPHRHRMVVLEPLNKLLQAKWDLLIPKFFLNFLCNLIYMFIFTAVAYHQPTLKKQAA
hVR2.altFL  HCKSPHRHRMVVLEPLNKLLQAKWDLLIPKFFLNFLCNLIYMFIFTAVAYHQPTLKKQAA
            ************************************************************ humanVR2    PHLKAEVGNSMLLTGHILILLGGIYLLVGQLWYFWRRHVFIWISFIDSYFEILFLFQALL
hVR2.altFL  PHLKAEVGNSMLLTGHILILLGGIYLLVGQLWYFWRRHVFIWISFIDSYFEILFLFQALL
            ************************************************************ humanVR2    TVVSQVLCFLAIEWYLPLLVSALVLGWLNLLYYTRGFQHTGIYSVMIQKVILRDLLRFLL
hVR2.altFL  TVVSQVLCFLAIEWYLPLLVSALVLGWLNLLYYTRGFQHTGIYSVMIQK-----------
            ************************************************ humanVR2    IYLVFLFGFAVALVSLSQEAWRPEAPTGPNATESVQPMEGQEDEGNGAQYRGILEASLEL
hVR2.altFL  ------------------------------------------------------------ humanVR2    FKFTIGMGELAFQEQLHFRGMVLLLLLAYVLLTYILLLNMLIALMSETVNSVATDSWSIW
hVR2.altFL  ------------------------------------------------------------ humanVR2    KLQKAISVLEMENGYWWCRKKQRAGVMLTVGTKPDGSPDERWCFRVEEVNWASWEQTLPT
hVR2.altFL  ---KAISVLEMENGYWWCRKKQRAGVMLTVGTKPDGSPDERWCFRVEEVNWASWEQTLPT
               ********************************************************* humanVR2    LCEDPSGAGVPRTLENPVLASPPKEDEDGASEENYVPVQLLQSN
hVR2.altFL  LCEDPSGAGVPRTLENPVLASPPKEDEDGASEENYVPVQLLQSN
            *******************************************
```

Fig. 17

MEMBERS OF THE CAPSAICIN/VANILLOID RECEPTOR FAMILY OF PROTEINS AND USES THEREOF

This application is a division of Ser. No. 11/967,558 filed Dec. 31, 2007, which is a continuation of Ser. No. 11/013,090 filed Dec. 15, 2004, now U.S. Pat. No. 7,323,314, which is a division of Ser. No. 09/587,111 filed Jun. 2, 2000, now U.S. Pat. No. 7,063,951, which is a division of Ser. No. 09/439,165 filed Nov. 12, 1999, now abandoned, which is a continuation-in-part of Ser. No. 09/421,134 filed Oct. 19, 1999, now abandoned, which is a continuation-in-part of Ser. No. 09/258,633 filed Feb. 26, 1999, now abandoned, which claims priority to Ser. No. 60/108,322 filed Nov. 13, 1998 and Ser. No. 60/114,078 filed Dec. 28, 1998. Each of these applications is incorporated by reference herein in its entirety.

This application incorporates by reference a 144 kb text file created on Oct. 22, 2010 and named "12895052sequencelisting.txt," which is the sequence listing for this application.

BACKGROUND OF THE INVENTION

Pain is initiated when the peripheral terminals of a sub-group of sensory neurons are activated by noxious chemical, mechanical or thermal stimuli. These neurons, called nociceptors, transmit information regarding tissue damage to pain-processing centres in the spinal chord and brain (Fields, H. L. *Pain*, McGraw-Hill, New York, 1987). Nociceptors are characterized in part, by their sensitivity to capsaicin, a vanilloid-containing compound, and a natural product of capsicum peppers that is the active ingredient of many "hot" and spicy foods. In mammals, exposure of nociceptor terminals to capsaicin leads initially to excitation of the neuron and the consequent perception of pain and local release of inflammatory mediators. With prolonged exposure, nociceptor terminals become insensitive to capsaicin, as well as to other noxious stimuli (Szolcsanyi, J. in *Capsaicin in the Study of Pain* (ed. Wood, J.) 1-26 (Academic, London, 1993). This latter phenomenon of nociceptor desensitization underlies the seemingly paradoxical use of capsaicin as an analgesic agent in the treatment of painful disorders ranging from viral and diabetic neuropathies to rheumatoid arthritis (Campbell, E. in Capsaicin and the Study of Pain (ed. Wood, J.) 255-272 (Academic, London, 1993); Szallasi, A. et al. (1996) *Pain* 68, 195-208). Some of this decreased sensitivity to noxious stimuli may result from reversible changes in the nociceptor, but the long-term loss of responsiveness can be explained by death of the nociceptor or destruction of its peripheral terminals following exposure to capsaicin (Jancso, G. et al. (1977) *Nature* 270, 741-743).

The cellular specificity of capsaicin action and its ability to evoke the sensation of burning pain have led to speculation that the target of capsaicin action plays an important physiological role in the detection of painful stimuli. Indeed, capsaicin may elicit the perception of pain by mimicking the actions of a physiological stimulus or an endogenous ligand produced during tissue injury (James, I. F., Kinkina, N. N. & Wood, J. N. in *Capsaicin in the Study of Pain* (ed. Wood, J. N.) 83-104 (Academic, London, 1993).

Caterina M. J. et al. have recently determined the molecular basis underlying this phenomenon by characterizing a functional cDNA that encodes a vanilloid receptor (VR-1) in rat sensory ganglia (Caterina M. J. et al., (1997) *Nature* 389:816-824). VR-1 is a vanilloid-gated, nonselective cation channel that resembles members of the transient receptor potential (TRP) channel family, first identified as components of the *Drosophila* phototransduction pathway (Montell et al. (1989) *Neuron* 2:1313-1323).

SUMMARY OF THE INVENTION

The present invention is based, at least in part, on the discovery of novel members of the Capsaicin/Vanilloid family of receptors. Described herein is the isolation of the human orthologue of rat VR-1 (rVR-1), referred to herein as hVR-1, as well as another previously unknown member of the VR family of receptors, referred herein as VR-2, and specifically as human VR-2 (hVR-2, including an alternate form which contains a deletion) and rat VR-2 (rVR-2) nucleic acid and protein molecules. The hVR-1, hVR-2, and rVR-2 molecules of the present invention are useful as targets for developing modulating agents to regulate a variety of cellular processes, e.g., cellular processes involved in pain. Accordingly, in one aspect, this invention provides isolated nucleic acid molecules encoding hVR-1, hVR-2, and rVR-2 proteins and fragments thereof, as well as nucleic acid fragments suitable as primers or hybridization probes for the detection of hVR-1, hVR-2, and rVR-2-encoding nucleic acids.

In one embodiment, an hVR-1, hVR-2, or rVR-2 nucleic acid molecule of the invention is at least 60%, 65%, 70%, 75%, 80%, 83%, 85%, 86%, 87%, 88%, 89%, 90%, 91%, 92%, 93%, 94%, 95%, 96%, 97%, 98%, 99% or more identical to the nucleotide sequence (e.g., to the entire length of the nucleotide sequence) shown in SEQ ID NO:1, 3, 4, 6, 7, 9, 10, or 12, or a complement thereof.

In another embodiment, the isolated nucleic acid molecule includes the nucleotide sequence shown SEQ ID NO:1, 3, 4, 6, 7, 9, 10, or 12, or a complement thereof. In another embodiment, the nucleic acid molecule includes at least 10, 15, 20, or more contiguous nucleotides of SEQ ID NO:1, 3, 4, 6, 7, 9, 10, or 12.

In another embodiment, an hVR-1, hVR-2, and rVR-2 nucleic acid molecule includes a nucleotide sequence encoding a protein having an amino acid sequence sufficiently homologous to the amino acid sequence of SEQ ID NO:2, 5, 8, or 11. In one embodiment, an hVR-1, hVR-2, and rVR-2 nucleic acid molecule includes a nucleotide sequence encoding a protein having an amino acid sequence at least 60%, 65%, 70%, 75%, 80%, 85%, 87%, 90%, 95%, 98% or more identical to the entire length of the amino acid sequence of SEQ ID NO:2, 5, 8, or 11.

Another embodiment of the invention features nucleic acid molecules, preferably hVR-1, hVR-2, and rVR-2 nucleic acid molecules, which specifically detect hVR-1, hVR-2, and rVR-2 nucleic acid molecules relative to nucleic acid molecules encoding non-hVR-1, non-hVR-2, and non-hVR-2 proteins. For example, in one embodiment, such a nucleic acid molecule is at least 100-150, 1150-200, 200-250, 250-300, 300-350, 350-400, 400-450, 450-500, 500-550, 550-600, 600-700, 700-800, 800-900, 900-1000, 1088, or more nucleotides in length and hybridizes under stringent conditions to a nucleic acid molecule comprising the nucleotide sequence shown in SEQ ID NO:1, 3, 4, 6, 7, 9, 10, or 12. In preferred embodiments, the nucleic acid molecules are at least 15 (e.g., contiguous) nucleotides in length and hybridize under stringent conditions to nucleotides 1-17, 3696-3863, or 3901-3909 of SEQ ID NO:1. In other preferred embodiments, the nucleic acid molecules comprise nucleotides 1-17, 3696-3863, or 3901-3909 of SEQ ID NO:1. In yet other preferred embodiments, the nucleic acid molecules consist of nucleotides 1-17, 3696-3863, or 3901-3909 of SEQ ID NO:1. In preferred embodiments, the nucleic acid molecules are at least 15 (e.g., contiguous) nucleotides in length and hybridize under stringent conditions to nucleotides 1944-2003 of SEQ ID NO:4. In other preferred embodiments, the nucleic acid molecules comprise nucleotides 1944-2003 of SEQ ID NO:4. In yet other preferred embodiments, the nucleic acid molecules consist of nucleotides 1944-2003 of SEQ ID NO:4.

In other embodiments, the nucleic acid molecule encodes a naturally occurring allelic variant of a polypeptide comprising the amino acid sequence of SEQ ID NO:2, 5, 8, or 11, wherein the nucleic acid molecule hybridizes to a nucleic acid molecule consisting of SEQ ID NO:1, 3, 4, 6, 7, 9, 10, or 12 under stringent conditions and is encoded by the same locus as hVR-1, hVR-2 or rVR-2.

Another embodiment of the invention provides a nucleic acid molecule that encodes a naturally occurring orthologue of a polypeptide comprising the amino acid sequence of SEQ ID NO:2, 5, 8, or 11, wherein the nucleic acid molecule hybridizes to a nucleic acid molecule consisting of SEQ ID NO:1, 3, 4, 6, 7, 9, 10, or 12 under stringent conditions.

Another embodiment of the invention provides an isolated nucleic acid molecule which is antisense to an hVR-1, hVR-2, and rVR-2 nucleic acid molecule, e.g., the coding strand of an hVR-1, hVR-2, and rVR-2 nucleic acid molecule.

Since the hVR2 (the alternate form) and rVR2 sequences represent fragments of the entire coding regions of these genes, another embodiment of the invention provides the complete gene sequences. A skilled artisan can readily isolate such molecule using the sequences disclosed herein.

Another aspect of the invention provides a vector comprising an hVR-1, an hVR-2, or a rVR-2 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an hVR-1, hVR-2, and rVR-2 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant hVR-1, hVR-2, and rVR-2 proteins and polypeptides. In one embodiment, the isolated protein, preferably an hVR-1, hVR-2, or rVR-2 protein, includes at least one transmembrane domain. In another embodiment, the isolated protein, preferably an hVR-1, hVR-2, or rVR-2 protein, includes at least one transmembrane domain and at least one proline rich domain. In yet another embodiment, the isolated protein, preferably an hVR-1, hVR-2, or rVR-2 protein, includes at least one transmembrane domain, at least one proline rich domain, and at least one ankyrin repeat domain. In yet another embodiment, the protein, preferably an hVR-1, hVR-2, or rVR-2 protein, includes at least one transmembrane domain, at least one proline rich domain, and at least one ankyrin repeat domain and has an amino acid sequence at least about 60%, 65%, 70%, 75%, 80%, 85%, 87%, 90%, 95%, 98% or more homologous to the amino acid sequence of SEQ ID NO:2, 5, 8, or 11. In another embodiment, the protein, preferably an hVR-1, hVR-2, or rVR-2 protein, includes at least one transmembrane domain, at least one proline rich domain, and at least one ankyrin repeat domain and plays a role in the development and regulation of pain. In yet another embodiment, the protein, preferably an hVR-1, hVR-2, and rVR-2 protein, includes at least one transmembrane domain, at least one proline rich domain, and at least one ankyrin repeat domain and is encoded by a nucleic acid molecule having a nucleotide sequence which hybridizes under stringent hybridization conditions to a nucleic acid molecule comprising the nucleotide sequence of SEQ ID NO:1, 3, 4, 6, 7, 9, 10, or 12.

In another embodiment, the invention features fragments of the protein having the amino acid sequence of SEQ ID NO:2, 5, 8, or 11, wherein the fragment comprises at least 15, 30, 40, 50, 60, 70, 80, 90, or 100 amino acids (e.g., contiguous amino acids).

In another embodiment, the invention features an isolated protein, preferably an hVR-1, hVR-2, and rVR-2 protein, which is encoded by a nucleic acid molecule consisting of a nucleotide sequence at least about 60%, 65%, 70%, 75%, 80%, 83%, 85%, 86%, 87%, 88%, 89%, 90%, 91%, 92%, 93%, 94%, 95%, 96%, 97%, 98%, 99% or more homologous to a nucleotide sequence of SEQ ID NO:1, 3, 4, 6, 7, 9, 10, or 12, or a complement thereof. This invention further features an isolated protein, preferably an hVR-1, hVR-2, or rVR-2 protein, which is encoded by a nucleic acid molecule consisting of a nucleotide sequence which hybridizes under stringent hybridization conditions to a nucleic acid molecule consisting of the nucleotide sequence of SEQ ID NO:1, 3, 4, 6, 7, 9, 10, or 12, or a complement thereof.

The proteins of the present invention or portions thereof, e.g., biologically active portions thereof, can be operatively linked to a non-hVR-1, non-hVR-2, or non-rVR-2 polypeptide (e.g., heterologous amino acid sequences) to form fusion proteins. The invention further features antibodies, such as monoclonal or polyclonal antibodies, that specifically bind proteins of the invention, preferably hVR-1, hVR-2, and rVR-2 proteins. In addition, the hVR-1, hVR-2, and rVR-2 proteins or biologically active portions thereof can be incorporated into pharmaceutical compositions, which optionally include pharmaceutically acceptable carriers.

In another aspect, the present invention provides a method for detecting the presence of an hVR-1, hVR-2, and rVR-2 nucleic acid molecule, protein or polypeptide in a biological sample by contacting the biological sample with an agent capable of detecting an hVR-1, hVR-2, and rVR-2 nucleic acid molecule, protein or polypeptide such that the presence of an hVR-1, hVR-2, and rVR-2 nucleic acid molecule, protein or polypeptide is detected in the biological sample.

In another aspect, the present invention provides a method for detecting the presence of hVR-1, hVR-2, and rVR-2 activity in a biological sample by contacting the biological sample with an agent capable of detecting an indicator of hVR-1, hVR-2, and rVR-2 activity such that the presence of hVR-1, hVR-2, and rVR-2 activity is detected in the biological sample.

In another aspect, the invention provides a method for modulating hVR-1, hVR-2, and rVR-2 activity comprising contacting a cell capable of expressing hVR-1, hVR-2, and rVR-2 with an agent that modulates hVR-1, hVR-2, and rVR-2 activity such that hVR-1, hVR-2, and rVR-2 activity in the cell is modulated. In one embodiment, the agent inhibits hVR-1, hVR-2, and rVR-2 activity. In another embodiment, the agent stimulates hVR-1, hVR-2, and rVR-2 activity. In one embodiment, the agent is an antibody that specifically binds to an hVR-1, hVR-2, and rVR-2 protein. In another embodiment, the agent modulates expression of hVR-1, hVR-2, and rVR-2 by modulating transcription of an hVR-1, hVR-2, and rVR-2 gene or translation of an hVR-1, hVR-2, and rVR-2 mRNA. In yet another embodiment, the agent is a nucleic acid molecule having a nucleotide sequence that is antisense to the coding strand of an hVR-1, hVR-2, and rVR-2 mRNA or an hVR-1, hVR-2, and rVR-2 gene.

In one embodiment, the methods of the present invention are used to treat a subject having a disorder characterized by aberrant hVR-1, hVR-2, and rVR-2 protein or nucleic acid expression or activity by administering an agent which is an hVR-1, hVR-2, and rVR-2 modulator to the subject. In one embodiment, the hVR-1, hVR-2, and rVR-2 modulator is an hVR-1, hVR-2, and rVR-2 protein. In another embodiment the hVR-1, hVR-2, and rVR-2 modulator is an hVR-1, hVR-2, and rVR-2 nucleic acid molecule. In yet another embodiment, the hVR-1, hVR-2, and rVR-2 modulator is a peptide, peptidomimetic, or other small molecule. In a further embodiment, the disorder characterized by aberrant hVR-1, hVR-2, and rVR-2 protein or nucleic acid expression is a pain disorder, e.g., hyperalgesia.

The present invention also provides a diagnostic assay for identifying the presence or absence of a genetic alteration characterized by at least one of (i) aberrant modification or mutation of a gene encoding an hVR-1, hVR-2, and rVR-2 protein; (ii) mis-regulation of the gene; and (iii) aberrant post-translational modification of an hVR-1, hVR-2, and rVR-2 protein, wherein a wild-type form of the gene encodes a protein with an hVR-1, hVR-2, and rVR-2 activity (as described herein).

In another aspect the invention provides a method for identifying a compound that binds to or modulates the activity of an hVR-1, hVR-2, and rVR-2 protein, by providing an indicator composition comprising an hVR-1, hVR-2, and rVR-2 protein having hVR-1, hVR-2, and rVR-2 activity, contacting the indicator composition with a test compound, and determining the effect of the test compound on hVR-1, hVR-2, and rVR-2 activity in the indicator composition to identify a compound that modulates the activity of an hVR-1, hVR-2, and rVR-2 protein.

Other features and advantages of the invention will be apparent from the following detailed description and claims.

BRIEF DESCRIPTION OF THE DRAWINGS

FIGS. 1A-1D depict the full length cDNA sequence and predicted amino acid sequence of human VR-1 (hVR-1). The nucleotide sequence corresponds to nucleic acids 1 to 3909 of SEQ ID NO:1. The amino acid sequence corresponds to amino acids 1 to 839 of SEQ ID NO:2. The coding region without the 5' and 3' untranslated regions of the human VR-1 (hVR-1) gene is shown in SEQ ID NO:3.

FIGS. 2A-2C depict the full length cDNA sequence and predicted amino acid sequence of human VR-2 (hVR-2). The nucleotide sequence corresponds to nucleic acids 1 to 2809 of SEQ ID NO:4. The amino acid sequence corresponds to amino acids 1 to 764 of SEQ ID NO:5. The coding region without the 5' and 3' untranslated regions of the human VR-2 (hVR-2) gene is shown in SEQ ID NO:6.

FIGS. 3A-3B depict the partial cDNA sequence and partial predicted amino acid sequence of an alternate form of human VR-2 (hVR-2). The nucleotide sequence corresponds to nucleic acids 1 to 1489 of SEQ ID NO:7. The amino acid sequence corresponds to amino acids 1 to 436 of SEQ ID NO:8. The coding region without the 5' and 3' untranslated regions of the alternate form of human VR-2 (hVR-2) gene is shown in SEQ ID NO:9.

FIGS. 4A-4B depict the partial cDNA sequence and partial predicted amino acid sequence of rat VR-2 (rVR-2). The nucleotide sequence corresponds to nucleic acids 1 to 1794 of SEQ ID NO:10. The amino acid sequence corresponds to amino acids 1 to 554 of SEQ ID NO:11. The coding region without the 5' and 3' untranslated regions of the rat VR-2 (rVR-2) gene is shown in SEQ ID NO:12.

FIGS. 5A-5B depict an alignment of the hVR-1 protein (SEQ ID NO:2) with the human VR-2 protein (SEQ ID NO:5) using the GAP program in the GCG software package (Blosum 62 matrix) and a gap weight of 12 and a length weight of 4.

FIGS. 6A-6F depict an alignment of the hVR-1 nucleotide sequence (SEQ ID NO:1) with the human VR-2 nucleotide sequence (SEQ ID NO:4) using the GAP program in the GCG software package (nwsgapdna matrix) and a gap weight of 50 and a length weight of 3.

FIG. 7 depicts an alignment of the hVR-2 protein (SEQ ID NO:5) with the rat VR-2 protein (SEQ ID NO:11) using the CLUSTAL W (1.74) multiple sequence alignment program.

FIGS. 8A-8B depict an alignment of the hVR-2 protein (SEQ ID NO:5) with the rat VR-2 protein (SEQ ID NO:11) using the GAP program in the GCG software package (Blosum 62 matrix) and a gap weight of 12 and a length weight of 4.

FIGS. 9A-9F depict an alignment of the hVR-1 nucleotide sequence (SEQ ID NO:1) with the rat VR-1 nucleotide sequence (Accession Number: AF029310, SEQ ID NO:21) using the GAP program in the GCG software package (nwsgapdna matrix) and a gap weight of 50 and a length weight of 3.

FIGS. 10A-10B depict an alignment of the hVR-1 protein (SEQ ID NO:2) with the rat VR-1 protein (Accession Number: AF029310, SEQ ID NO:22) using the GAP program in the GCG software package (Blosum 62 matrix) and a gap weight of 12 and a length weight of 4.

FIG. 11 depicts an alignment of the hVR-2 protein (SEQ ID NO:5) with the human VR-2 protein (alternate form) (SEQ ID NO:8) using the CLUSTAL W (1.74) multiple sequence alignment program.

FIG. 13 depicts an alignment between the amino acid sequence of the hVR-1 protein (SEQ ID NO:2) and Ank repeat domains (SEQ ID NO:23) identified while performing a search using the amino acid sequence of the hVR-1 protein against the HMM database.

FIG. 15 depicts an alignment between the amino acid sequence of the hVR-2 protein (SEQ ID NO:5) and Ank repeat domains (SEQ ID NO:23) identified while performing a search using the amino acid sequence of the hVR-2 protein against the HMM database.

FIG. 16 depicts the predicted full length amino acid sequence of the human VR-2 protein (alternate form) (SEQ ID NO:20).

FIG. 17 depicts an alignment of the hVR-2 protein (SEQ ID NO:5) with the predicted full length human VR-2 protein (alternate form) (SEQ ID NO:20) using the CLUSTAL W (1.74) multiple sequence alignment program.

DETAILED DESCRIPTION OF THE INVENTION

Figure 12:
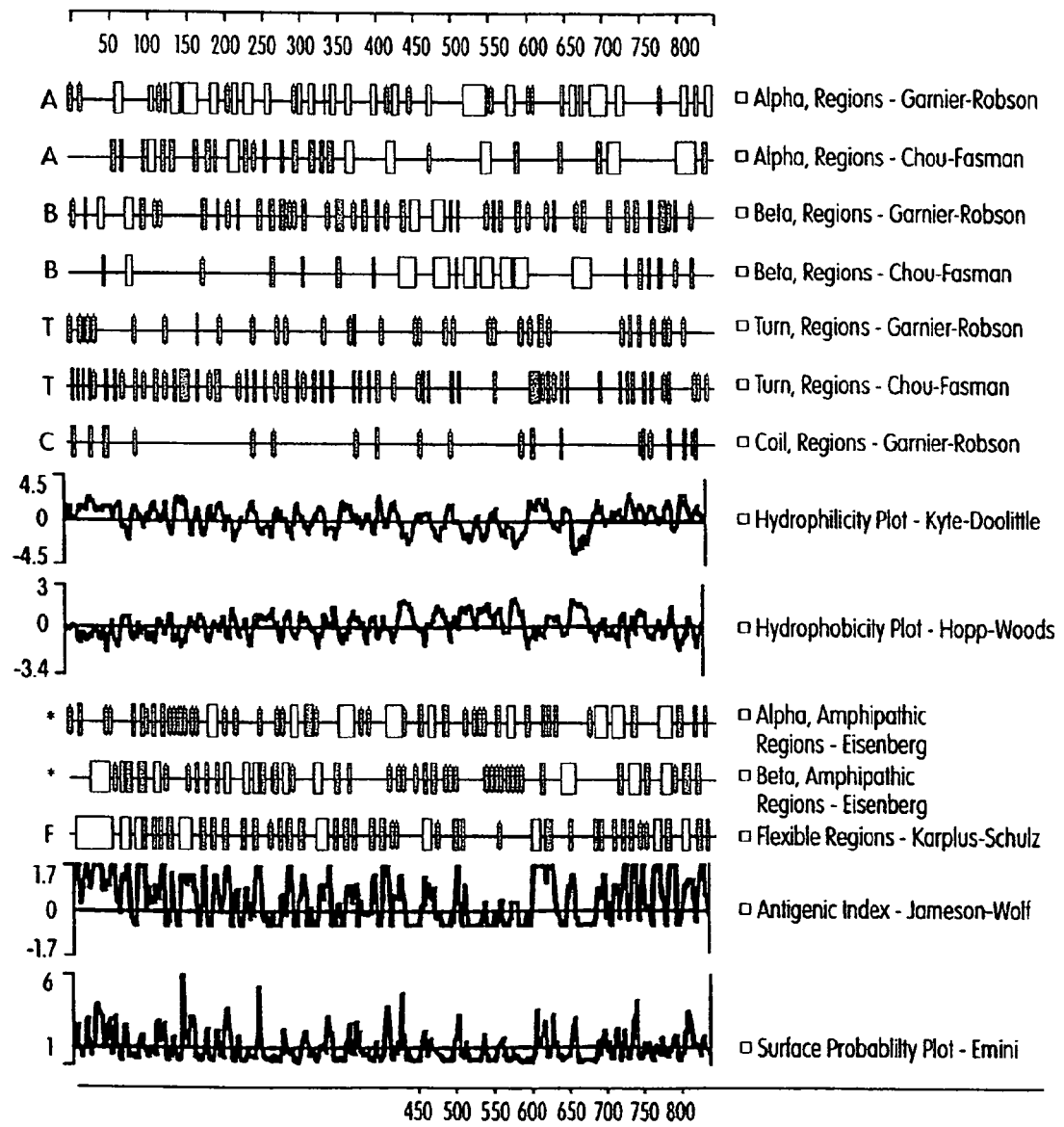
FIG. 12 depicts a structural, hydrophobicity, and antigenicity analysis of the hVR-1 protein.

The present invention is based, at least in part, on the discovery of nucleic acid and amino acid molecules which are novel members of the Capsaicin/Vanilloid family of receptors. Described herein is the isolation of the human orthologue of rat VR-1 (rVR-1), referred to herein as hVR-1, as well as another previously unknown member of the VR family of receptors, referred herein as VR-2, and specifically as human VR-2 (hVR-2) and rat VR-2 (rVR-2) nucleic acid and protein molecules. The hVR-1, hVR-2, and rVR-2 molecules were identified based on their sequence similarity to the known rat vanilloid receptor (VR-1). VR-1 is a vanilloid gated, non-selective cation channel which resembles members of the transient receptor potential (TRP) ion channel family (described in Montell et al. (1989) *Neuron* 2:1313-1323) that mediate the influx of extracellular calcium in response to depletion of intracellular calcium stores. The rat VR-1 cDNA contains an open reading frame of 2514 nucleotides that encodes a protein of 838 amino acids. Hydrophilicity analysis has indicated that rat VR-1 contains six transmembrane domains (predicted to be mostly α-helices) with an additional short hydrophobic stretch between transmembrane regions 5 and 6. The amino terminal hydrophilic segment contains a relatively proline rich region followed by three ankyrin repeat domains. The rat VR-1 is expressed in small diameter neurons within sensory ganglia. The present hVR-1 sequence is the human orthologue of rVR-1. As described in further detail infra, the human VR-1 is expressed in nodose, trigeminal sensory neurons, as well as in some, but not all, small dorsal root ganglion (DRG) neurons and in a few medium sized DRG neurons.

The hVR-1, hVR-2, and rVR-2 molecules of the present invention play a role in pain signaling mechanisms. As used herein, the term "pain signaling mechanisms" includes the cellular mechanisms involved in the development and regulation of pain, e.g., pain elicited by noxious chemical, mechanical, or thermal stimuli, in a subject, e.g., a mammal such as a human. In mammals, the initial detection of noxious chemical, mechanical, or thermal stimuli, a process referred to as "nociception", occurs predominantly at the peripheral terminals of specialized, small diameter primary afferent neurons, called polymodal nociceptors. These afferent neurons transmit the information to the central nervous system, evoking a perception of pain or discomfort and initiating appropriate protective reflexes. Capsaicin/Vanilloid receptors, e.g., the hVR-1, hVR-2, and rVR-2 molecules of the present invention, present on these afferent neurons, are involved in detecting these noxious chemical, mechanical, or thermal stimuli and transducing this information into membrane depolarization events. Thus, the hVR-1, hVR-2, and rVR-2 molecules by participating in pain signaling mechanisms, can modulate pain elicitation and provide novel diagnostic targets and therapeutic agents to control pain.

The hVR-1, hVR-2, and rVR-2 molecules provide novel diagnostic targets and therapeutic agents to control pain in a variety of disorders, diseases, or conditions which are characterized by a deregulated, e.g., upregulated or downregulated, pain response. For example, the hVR-1, hVR-2, and rVR-2 molecules provide novel diagnostic targets and therapeutic agents to control the exaggerated pain response elicited during various forms of tissue injury, e.g., inflammation, infection, and ischemia, usually referred to as hyperalgesia (described in, for example, Fields, H. L. (1987) *Pain*, New York: McGraw-Hill). Moreover, the hVR-1, hVR-2, and rVR-2 molecules provide novel diagnostic targets and therapeutic agents to control pain associated with muscoloskeletal disorders, e.g., joint pain; tooth pain; headaches; pain associated with surgery, or neuropathic pain.

As the hVR-1 gene maps to a region of human chromosome 17 between WI-5436 (7.7cR) and WI-6584 (18.9cR) (Example 6), which has been associated with myasthenia gravis, Smith-Magenis syndrome, CORDS, Cone-rod dysrtophy, and breast cancer, the hVR-1 molecule may provide novel diagnostic targets and therapeutic agents to treat, diagnose, or prognose these disorders or other disorders linked to this chromosomal region. Similarly, as the hVR-2 gene maps to a region of human chromosome 17 between AFMA043ZB5 (23.3 cR) and D175721 (29.3cR) (Example 6) which has been associated with myasthenia gravis, Smith-Magenis syndrome, CORDS, Cone-rod dysrtophy, choroidal dystrophy, central areolar, and retinal cone dystrophy, the hVR-2 molecule may provide novel diagnostic targets and therapeutic agents to treat, diagnose, or prognose these disorders or other disorders linked to this chromosomal region.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of hVR-1, hVR-2, and rVR-2 proteins comprise at least one, and preferably six "transmembrane domains." As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have a helical structure. In a embodiment, at least 50%, 60%, 70%, 80%, 90%, 95% or more of the amino acid residues of a transmembrane domain are hydrophobic, e.g., leucines, isoleucines, tyrosines, or tryptophans. Transmembrane domains are described in, for example, Zagotta W. N. et al, (1996) *Annual Rev. Neurosci.* 19: 235-63, the contents of which are incorporated herein by reference. Amino acid residues 434-455, 480-495, (509-531; based on homology to the rat VR-1) or 514-531, (543-569; based on homology to the rat VR-1) or 538-555, (577-596; based on homology to the rat VR-1) or 580-599, and (656-683; based on homology to the rat VR-1) or 658-682 of hVR-1 (SEQ ID NO:2) and amino acid residues 391-410, 431-448, 459-476, 486-508, 538-556, and 621-645 of hVR-2 (SEQ ID NO:5) comprise transmembrane domains.

In another embodiment, an hVR-1, hVR-2, and rVR-2 of the present invention is identified based on the presence of a "proline rich domain" in the protein or corresponding nucleic acid molecule. As used herein, the term "proline rich domain" includes an amino acid sequence of about 4-6 amino acid residues in length having the general sequence X-Pro-X-X-Pro-X (where X can be any amino acid). Proline rich domains are usually located in a helical structure and bind through hydrophobic interactions to SH3 domains. SH3 domains recognize proline rich domains in both forward and reverse orientations. Proline rich domains are described in, for example, Sattler M. et al. (1998) *Leukemia* 12:637-644, the contents of which are incorporated herein by reference.

In another embodiment, an hVR-1, hVR-2, and rVR-2 of the present invention is identified based on the presence of an "ankyrin repeat domain" in the protein or corresponding nucleic acid molecule. As used herein, the term "ankyrin repeat domain" includes a protein domain having an amino acid sequence of about 30-50 amino acid residues and having a bit score for the alignment of the sequence to the ankyrin repeat domain (HMM) of at least 6. Preferably, an ankyrin repeat domain includes at least about 30-45, more preferably about 30-40 amino acid residues, or about 30-35 amino acids and has a bit score for the alignment of the sequence to the ankyrin repeat domain (HMM) of at least 3-10, more preferably 10-30, more preferably 30-50, even more preferably 50-75, 75-100, 100-200 or greater. The ankyrin repeat domain HMM has been assigned the PFAM Accession PF00023 (genome.wustl.edu/Pfam/.html). Ankyrin repeats are involved in protein-protein interactions and are described in, for example, Ketchum K. A et al. (1996) *FEBS Letters* 378:19-26, the contents of which are incorporated herein by reference.

To identify the presence of an ankyrin repeat domain in an hVR-1, hVR-2, and rVR-2 protein and make the determination that a protein of interest has a particular profile, the amino acid sequence of the protein is searched against a database of HMMs (e.g., the Pfam database, release 2.1) using the default parameters (www.sanger.ac.uk/Software/Pfam/HMM_search). A description of the Pfam database can be found in Sonhammer et al. (1997) *Proteins* 28(3)405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of three ankyrin repeat domains in the amino acid sequence of SEQ ID NO:2 (at about residues 201-233, 248-283, and 333-361) and SEQ ID NO:5 (at about residues 162-194, 208-243, and 293-328). The results of the searches are set forth in FIGS. 13 and 15.

Isolated proteins of the present invention, preferably hVR-1, hVR-2, and rVR-2 proteins, have an amino acid sequence sufficiently identical to the amino acid sequence of SEQ ID NO:2, 5, 8, or 11 or are encoded by a nucleotide sequence sufficiently identical to SEQ ID NO:1, 3, 4, 6, 7, 9, 10, or 12. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% identity, preferably 60% identity, more preferably 70%-80%, and even more preferably 90-95% identity across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% identity and share a common functional activity are defined herein as sufficiently identical.

As used interchangeably herein, an "hVR-1, hVR-2, and rVR-2 activity", "biological activity of hVR-1, hVR-2, and rVR-2" or "functional activity of hVR-1, hVR-2, and rVR-2", refers to an activity exerted by an hVR-1, hVR-2, and rVR-2 protein, polypeptide or nucleic acid molecule on an hVR-1, hVR-2, and rVR-2 responsive cell or on an hVR-1, hVR-2, and rVR-2 protein substrate, as determined in vivo, or in vitro, according to standard techniques. In one embodiment, an hVR-1, hVR-2, and rVR-2 activity is a direct activity, such as an association with an hVR-1, hVR-2, and rVR-2-target molecule. As used herein, a "target molecule" or "binding partner" is a molecule with which an hVR-1, hVR-2, and rVR-2 protein binds or interacts in nature, such that hVR-1, hVR-2, and rVR-2-mediated function is achieved. An hVR-1, hVR-2, and rVR-2 target molecule can be a non-hVR-1, non-hVR-2, and non-rVR-2 molecule or an hVR-1, hVR-2, and rVR-2 protein or polypeptide of the present invention. In an exemplary embodiment, an hVR-1, hVR-2, and rVR-2 target molecule is an hVR-1, hVR-2, and rVR-2 ligand, e.g., capsaicin. Alternatively, an hVR-1, hVR-2, and rVR-2 activity is an indirect activity, such as a cellular signaling activity mediated by interaction of the hVR-1, hVR-2, and rVR-2 protein with an hVR-1, hVR-2, and rVR-2 ligand.

Accordingly, another embodiment of the invention features isolated hVR-1, hVR-2, and rVR-2 proteins and polypeptides having an hVR-1, hVR-2, and rVR-2 activity. Other proteins of the invention are hVR-1, hVR-2, and rVR-2 proteins having at least one, and preferably six, transmembrane domains and, preferably, an hVR-1, hVR-2, and rVR-2 activity. Yet other proteins of the invention are hVR-1, hVR-2, and rVR-2 proteins having at least one transmembrane domain, at least one proline rich domain and, preferably, an hVR-1, hVR-2, and rVR-2 activity. Other proteins of the invention are hVR-1, hVR-2, and rVR-2 proteins having at least one transmembrane domain, at least one proline rich domain, at least one ankyrin repeat domain and, preferably, an hVR-1, hVR-2, and rVR-2 activity. Additional proteins of the invention have at least one transmembrane domain, at least one proline rich domain, at least one ankyrin repeat domain, and are, preferably, encoded by a nucleic acid molecule having a nucleotide sequence which hybridizes under stringent hybridization conditions to a nucleic acid molecule comprising the nucleotide sequence of SEQ ID NO:1, 3, 4, 6, 7, 9, 10, or 12.

The nucleotide sequence of the full length hVR-1 cDNA and the predicted amino acid sequence of the hVR-1 polypeptide are shown in FIGS. 1A-1D and in SEQ ID NOS:1 and 2, respectively.

The nucleotide sequence of the full length hVR-2 cDNA and the predicted amino acid sequence of the hVR-2 polypeptide are shown in FIGS. 2A-2B and in SEQ ID NOS:4 and 5, respectively.

The nucleotide sequence of the partial hVR-2 (alternate form) cDNA and the predicted amino acid sequence of the hVR-2 (alternate form) polypeptide are shown in FIGS. 3A-3B and in SEQ ID NOS:7 and 8, respectively.

The nucleotide sequence of the partial rVR-2 cDNA and the predicted amino acid sequence of the rVR-2 polypeptide are shown in FIGS. 4A-4B and in SEQ ID NOS:10 and 11, respectively.

Various aspects of the invention are described in further detail in the following subsections:

I. Isolated Nucleic Acid Molecules

One aspect of the invention pertains to isolated nucleic acid molecules that encode hVR-1, hVR-2, and rVR-2 proteins or biologically active portions thereof, as well as nucleic acid fragments sufficient for use as hybridization probes to identify hVR-1, hVR-2, and rVR-2-encoding nucleic acid molecules (e.g., hVR-1, hVR-2, and rVR-2 mRNA) and fragments for use as PCR primers for the amplification or mutation of hVR-1, hVR-2, and rVR-2 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated hVR-1, hVR-2, and rVR-2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, 6, 7, 9, 10, or 12. Using all or portion of the nucleic acid sequence of SEQ ID NO:1, 3, 4, 6, 7, 9, 10, or 12, as a hybridization probe, hVR-1, hVR-2, and rVR-2 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, 3, 4, 6, 7, 9, 10, or 12, can be isolated by the polymerase chain reaction (PCR) using synthetic oligonucleotide primers designed based upon the sequence of SEQ ID NO:1, 3, 4, 6, 7, 9, 10, or 12.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to hVR-1, hVR-2, and rVR-2 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1. The sequence of SEQ ID NO:1 corresponds to the full length hVR-1 encoding cDNA.

In another embodiment, an isolated nucleic acid molecule of the invention comprises the nucleotide sequence shown in SEQ ID NO:4. The sequence of SEQ ID NO:4 corresponds to the full length hVR-2 encoding cDNA.

In another embodiment, an isolated nucleic acid molecule of the invention comprises the nucleotide sequence shown in SEQ ID NO:7. The sequence of SEQ ID NO:7 corresponds to a fragment of the hVR-2 (alternate form) encoding cDNA.

In another embodiment, an isolated nucleic acid molecule of the invention comprises the nucleotide sequence shown in SEQ ID NO:10. The sequence of SEQ ID NO:10 corresponds to a fragment of the rVR-2 cDNA.

In another embodiment, an isolated nucleic acid molecule of the invention comprises a nucleic acid molecule which is a complement of the nucleotide sequence shown in SEQ ID NO:1, 3, 4, 6, 7, 9, 10, or 12, or a portion of any of these nucleotide sequences. A nucleic acid molecule which is complementary to the nucleotide sequence shown in SEQ ID NO:1, 3, 4, 6, 7, 9, 10, or 12, is one which is sufficiently complementary to the nucleotide sequence shown in SEQ ID NO:1, 3, 4, 6, 7, 9, 10, or 12, such that it can hybridize to the nucleotide sequence shown in SEQ ID NO:1, 3, 4, 6, 7, 9, 10, or 12 thereby forming a stable duplex.

In still another embodiment, an isolated nucleic acid molecule of the present invention comprises a nucleotide sequence which is at least about 60%, 65%, 70%, 75%, 80%, 83%, 85%, 86%, 87%, 88%, 89%, 90%, 91%, 92%, 93%, 94%, 95%, 96%, 97%, 98%, 99% or more homologous to the entire length of the nucleotide sequence shown in SEQ ID NO:1, 3, 4, 6, 7, 9, 10, or 12, or a portion of any of these nucleotide sequences.

Moreover, the nucleic acid molecule of the invention can comprise only a portion of the nucleic acid sequence of SEQ ID NO:1, 3, 4, 6, 7, 9, 10, or 12, for example, a fragment which can be used as a probe or primer or a fragment encoding a portion of an hVR-1, hVR-2, and rVR-2 protein, e.g., a biologically active portion of an hVR-1, hVR-2, and rVR-2 protein. The nucleotide sequence determined from the cloning of the hVR-1, hVR-2, and rVR-2 gene allows for the generation of probes and primers designed for use in identifying and/or cloning other hVR-1, hVR-2, and rVR-2 family members, as well as hVR-1, hVR-2, and rVR-2 homologues from other species. The probe/primer typically comprises a substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, 75, or 100 consecutive nucleotides of a sense sequence of SEQ ID NO:1, 3, 4, 6, 7, 9, 10, or 12, of an anti-sense sequence of SEQ ID NO:1, 3, 4, 6, 7, 9, 10, or 12, or of a naturally occurring allelic variant or mutant of SEQ ID NO:1, 3, 4, 6, 7, 9, 10, or 12. In an exemplary embodiment, a nucleic acid molecule of the present invention comprises a nucleotide sequence which is greater than 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1088, or more nucleotides in length and hybridizes under stringent hybridization conditions to a nucleic acid molecule of SEQ ID NO:1, 3, 4, 6, 7, 9, 10, or 12.

Probes based on the hVR-1, hVR-2, and rVR-2 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an hVR-1, hVR-2, and rVR-2 protein, such as by measuring a level of an hVR-1, hVR-2, and rVR-2-encoding nucleic acid in a sample of cells from a subject e.g., detecting hVR-1, hVR-2, and rVR-2 mRNA levels or determining whether a genomic hVR-1, hVR-2, and rVR-2 gene has been mutated or deleted.

A nucleic acid fragment encoding a "biologically active portion of an hVR-1, hVR-2, and rVR-2 protein" can be prepared by isolating a portion of the nucleotide sequence of SEQ ID NO:1, 3, 4, 6, 7, 9, 10, or 12, which encodes a polypeptide having an hVR-1, hVR-2, and rVR-2 biological activity (the biological activities of the hVR-1, hVR-2, and rVR-2 proteins are described herein), expressing the encoded portion of the hVR-1, hVR-2, and rVR-2 protein (e.g., by recombinant expression in vitro) and assessing the activity of the encoded portion of the hVR-1, hVR-2, and rVR-2 protein.

The invention further encompasses nucleic acid molecules that differ from the nucleotide sequence shown in SEQ ID NO:1, 3, 4, 6, 7, 9, 10, or 12, due to degeneracy of the genetic code and thus encode the same hVR-1, hVR-2, and rVR-2 proteins as those encoded by the nucleotide sequence shown in SEQ ID NO:1, 3, 4, 6, 7, 9, 10, or 12. In another embodiment, an isolated nucleic acid molecule of the invention has a nucleotide sequence encoding a protein having an amino acid sequence shown in SEQ ID NO:2, 5, 8, or 11.

In addition to the hVR-1, hVR-2, and rVR-2 nucleotide sequences shown in SEQ ID NO:1, 3, 4, 6, 7, 9, 10, or 12, it will be appreciated by those skilled in the art that DNA sequence polymorphisms that lead to changes in the amino acid sequences of the hVR-1, hVR-2, and rVR-2 proteins may exist within a population (e.g., the human population). Such genetic polymorphism in the hVR-1, hVR-2, and rVR-2 genes may exist among individuals within a population due to natural allelic variation. As used herein, the terms "gene" and "recombinant gene" refer to nucleic acid molecules which include an open reading frame encoding an hVR-1, hVR-2, and rVR-2 protein, preferably a mammalian hVR-1, hVR-2, and rVR-2 protein, and can further include non-coding regulatory sequences, and introns.

Allelic variants of hVR-1, hVR-2, and rVR-2 include both functional and non-functional hVR-1, hVR-2, and rVR-2 proteins. Functional allelic variants are naturally occurring amino acid sequence variants of the hVR-1, hVR-2, and rVR-2 protein that maintain the ability to bind an hVR-1, hVR-2, and rVR-2 ligand and/or modulate a pain signaling mechanism. Functional allelic variants will typically contain only conservative substitution of one or more amino acids of SEQ ID NO:2, 5, 8, or 11, or substitution, deletion or insertion of non-critical residues in non-critical regions of the protein.

Non-functional allelic variants are naturally occurring amino acid sequence variants of the hVR-1, hVR-2, and rVR-2 protein that do not have the ability to either bind an hVR-1, hVR-2, and rVR-2 ligand and/or modulate a pain signaling mechanism. Non-functional allelic variants will typically contain a non-conservative substitution, a deletion, or insertion or premature truncation of the amino acid sequence of SEQ ID NO:2, 5, 8, or 11, or a substitution, insertion or deletion in critical residues or critical regions.

The present invention further provides non-human orthologues of the hVR-2 and rVR-2 protein. Orthologues of the hVR-2 and rVR-2 protein are proteins that are isolated from non-human and non-rat organisms and possess the same hVR-2 and rVR-2 ligand binding and/or modulation of pain signaling mechanism capabilities of the hVR-2 and rVR-2 proteins. Orthologues of the hVR-2 and rVR-2 proteins can readily be identified as comprising an amino acid sequence that is substantially homologous to SEQ ID NO: 4, 6, 8 or 10.

Moreover, nucleic acid molecules encoding other hVR-1, hVR-2, and rVR-2 family members and, thus, which have a nucleotide sequence which differs from the hVR-1, hVR-2, and rVR-2 sequences of SEQ ID NO:1, 3, 4, 6, 7, 9, 10, or 12, are intended to be within the scope of the invention. For example, another hVR-1, hVR-2, and rVR-2 cDNA can be identified based on the nucleotide sequence of hVR-1, hVR-2, and rVR-2. Moreover, nucleic acid molecules encoding VR-2 proteins from different species, and which, thus, have a nucleotide sequence which differs from the hVR-2 and rVR-2 sequences of SEQ ID NO:4, 6, 8, or 10 are intended to be within the scope of the invention. For example, a mouse hVR-2 cDNA can be identified based on the nucleotide sequence of the human VR-2 (hVR-2) or the rat VR-2 (rVR-2).

Nucleic acid molecules corresponding to natural allelic variants and homologues of the hVR-1, hVR-2, and rVR-2 cDNAs of the invention can be isolated based on their homology to the hVR-1, hVR-2, and rVR-2 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the hVR-1, hVR-2, and rVR-2 cDNAs of the invention can further be isolated by mapping to the same chromosome or locus as the hVR-1, hVR-2, and rVR-2 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 4, 6, 7, 9, 10, or 12. In other embodiment, the nucleic acid is at least 30, 50, 100, 150, 200, 250, 300, 350, 400, 450, 500, 550, 600, 650, 700, 750, 800, 850, 900, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1, 3, 4, 6, 7, 9, 10, or 12 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the hVR-1, hVR-2, and rVR-2 sequences that may exist in the population, the skilled artisan will further appreciate that changes can be introduced by mutation into the nucleotide sequences of SEQ ID NO:1, 3, 4, 6, 7, 9, 10, or 12, thereby leading to changes in the amino acid sequence of the encoded hVR-1, hVR-2, and rVR-2 proteins, without altering the functional ability of the hVR-1, hVR-2, and rVR-2 proteins. For example, nucleotide substitutions leading to amino acid substitutions at "non-essential" amino acid residues can be made in the sequence of SEQ ID NO:1, 3, 4, 6, 7, 9, 10, or 12. A "non-essential" amino acid residue is a residue that can be altered from the wild-type sequence of hVR-1, hVR-2, and rVR-2 (e.g., the sequence of SEQ ID NO:2, 5, 8, or 11) without altering the biological activity, whereas an "essential" amino acid residue is required for biological activity. For example, amino acid residues that are conserved among the hVR-1, hVR-2, and rVR-2 proteins of the present invention, are predicted to be particularly unamenable to alteration. Furthermore, additional amino acid residues that are conserved between the hVR-1, hVR-2, and rVR-2 proteins of the present invention and other members of the Capsaicin/Vanilloid receptor family are not likely to be amenable to alteration.

Accordingly, another aspect of the invention pertains to nucleic acid molecules encoding hVR-1, hVR-2, and rVR-2 proteins that contain changes in amino acid residues that are not essential for activity. Such hVR-1, hVR-2, and rVR-2 proteins differ in amino acid sequence from SEQ ID NO:2, 5, 8, or 11, yet retain biological activity. In one embodiment, the isolated nucleic acid molecule comprises a nucleotide sequence encoding a protein, wherein the protein comprises an amino acid sequence at least about 60%, 65%, 70%, 75%, 80%, 85%, 87%, 90%, 95%, 98% or more homologous to SEQ ID NO:2, 5, 8, or 11.

An isolated nucleic acid molecule encoding an hVR-1, hVR-2, and rVR-2 protein homologous to the protein of SEQ ID NO:2, 5, 8, or 11 can be created by introducing one or more nucleotide substitutions, additions or deletions into the nucleotide sequence of SEQ ID NO:1, 3, 4, 6, 7, 9, 10, or 12, such that one or more amino acid substitutions, additions or deletions are introduced into the encoded protein. Mutations can be introduced into SEQ ID NO:1, 3, 4, 6, 7, 9, 10, or 12, by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an hVR-1, hVR-2, and rVR-2 protein is preferably replaced with another amino acid residue from the same side chain family. Alternatively, in another embodiment, mutations can be introduced randomly along all or part of an hVR-1, hVR-2, and rVR-2 coding sequence, such as by saturation mutagenesis, and the resultant mutants can be screened for hVR-1, hVR-2, and rVR-2 biological activity to identify mutants that retain activity. Following mutagenesis of SEQ ID NO:1, 3, 4, 6, 7, 9, 10, or 12.

In a embodiment, a mutant hVR-1, hVR-2, and rVR-2 protein can be assayed for the ability to (1) interact with a non-hVR-1, non-hVR-2, or non-rVR-2 protein molecule, e.g., a vanilloid compound such as capsaicin; (2) modulate intracellular calcium concentration; (3) activate an hVR-1, hVR-2, and rVR-2-dependent signal transduction pathway; or (4) modulate a pain signaling mechanism.

In addition to the nucleic acid molecules encoding hVR-1, hVR-2, and rVR-2 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire hVR-1, hVR-2, and rVR-2 coding strand, or to only a portion thereof. In one embodiment, an antisense nucleic acid molecule is antisense to a "coding region" of the coding strand of a nucleotide sequence encoding hVR-1, hVR-2, and rVR-2. The term "coding region" refers to the region of the nucleotide sequence comprising codons which are translated into amino acid residues (e.g., the coding region of hVR-1, hVR-2, and rVR-2). In another embodiment, the antisense nucleic acid molecule is antisense to a "noncoding region" of the coding strand of a nucleotide sequence encoding hVR-1, hVR-2, and rVR-2. The term "noncoding region" refers to 5' and 3' sequences which flank the coding region that are not translated into amino acids (i.e., also referred to as 5' and 3' untranslated regions).

Given the coding strand sequences encoding hVR-1, hVR-2, and rVR-2 disclosed herein, antisense nucleic acids of the invention can be designed according to the rules of Watson and Crick base pairing. The antisense nucleic acid molecule can be complementary to the entire coding region of hVR-1, hVR-2, and rVR-2 mRNA, but more preferably is an oligonucleotide which is antisense to only a portion of the coding or noncoding region of hVR-1, hVR-2, and rVR-2 mRNA. For example, the antisense oligonucleotide can be complementary to the region surrounding the translation start site of hVR-1, hVR-2, and rVR-2 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an hVR-1, hVR-2, and rVR-2 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an -anomeric nucleic acid molecule. An α-anomeric nucleic acid molecule forms specific double-stranded hybrids with complementary RNA in which, contrary to the usual-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave hVR-1, hVR-2, and rVR-2 mRNA transcripts to thereby inhibit translation of hVR-1, hVR-2, and rVR-2 mRNA. A ribozyme having specificity for an hVR-1, hVR-2, and rVR-2-encoding nucleic acid can be designed based upon the nucleotide sequence of an hVR-1, hVR-2, and rVR-2 cDNA disclosed herein (i.e., SEQ ID NO:1, 3, 4, 6, 7, 9, 10, or 12). For example, a derivative of a *Tetrahymena* L-19 IVS RNA can be constructed in which the nucleotide sequence of the active site is complementary to the nucleotide sequence to be cleaved in an hVR-1, hVR-2, and rVR-2-encoding mRNA. See, e.g., Cech et al. U.S. Pat. No. 4,987,071; and Cech et al. U.S. Pat. No. 5,116,742. Alternatively, hVR-1, hVR-2, and rVR-2 mRNA can be used to select a catalytic RNA having a specific ribonuclease activity from a pool of RNA molecules. See, for example, Bartel, D. and Szostak, J. W. (1993) *Science* 261:1411-1418.

Alternatively, hVR-1, hVR-2, and rVR-2 gene expression can be inhibited by targeting nucleotide sequences complementary to the regulatory region of the hVR-1, hVR-2, and rVR-2 (e.g., the hVR-1, hVR-2, and rVR-2 promoter and/or enhancers) to form triple helical structures that prevent transcription of the hVR-1, hVR-2, and rVR-2 gene in target cells. See generally, Helene, C. (1991) *Anticancer Drug Des.* 6(6): 569-84; Helene, C. et al. (1992) *Ann. N.Y. Acad. Sci.* 660:27-36; and Maher, L. J. (1992) *Bioassays* 14(12):807-15.

In yet another embodiment, the hVR-1, hVR-2, and rVR-2 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of hVR-1, hVR-2, and rVR-2 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of hVR-1, hVR-2, and rVR-2 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of hVR-1, hVR-2, and rVR-2 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of hVR-1, hVR-2, and rVR-2 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

II. Isolated hVR-1, hVR-2, and rVR-2 Proteins and Anti-hVR-1, Anti-hVR-2, and Anti-rVR-2 Antibodies One aspect of the invention pertains to isolated hVR-1, hVR-2, and rVR-2 proteins, and biologically active portions thereof, as well as polypeptide fragments suitable for use as immunogens to raise anti-hVR-2, anti-hVR-2, and anti-rVR-2 antibodies. In one embodiment, native hVR-1, hVR-2, and rVR-2 proteins can be isolated from cells or tissue sources by an appropriate purification scheme using standard protein purification techniques. In another embodiment, hVR-1, hVR-2, and rVR-2 proteins are produced by recombinant DNA techniques. Alternative to recombinant expression, an hVR-1, hVR-2, and rVR-2 protein or polypeptide can be synthesized chemically using standard peptide synthesis techniques.

An "isolated" or "purified" protein or biologically active portion thereof is substantially free of cellular material or other contaminating proteins from the cell or tissue source from which the hVR-1, hVR-2, and rVR-2 protein is derived, or substantially free from chemical precursors or other chemicals when chemically synthesized. The language "substantially free of cellular material" includes preparations of hVR-1, hVR-2, and rVR-2 protein in which the protein is separated from cellular components of the cells from which it is isolated or recombinantly produced. In one embodiment, the language "substantially free of cellular material" includes preparations of hVR-1, hVR-2, and rVR-2 protein having less than about 30% (by dry weight) of non-hVR-1, hVR-2, and rVR-2 protein (also referred to herein as a "contaminating protein"), more preferably less than about 20% of non-hVR-1, hVR-2, and rVR-2 protein, still more preferably less than about 10% of non-hVR-1, hVR-2, and rVR-2 protein, and most preferably less than about 5% non-hVR-1, non-hVR-2, and non-rVR-2 protein. When the hVR-1, hVR-2, and rVR-2 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of hVR-1, hVR-2, and rVR-2 protein in which the protein is separated from chemical precursors or other chemicals which are involved in the synthesis of the protein. In one embodiment, the language "substantially free of chemical precursors or other chemicals" includes preparations of hVR-1, hVR-2, and rVR-2 protein having less than about 30% (by dry weight) of chemical precursors or non-hVR-1, hVR-2, and rVR-2 chemicals, more preferably less than about 20% chemical precursors or non-hVR-1, hVR-2, and rVR-2 chemicals, still more preferably less than about 10% chemical precursors or non-hVR-1, hVR-2, and rVR-2 chemicals, and most preferably less than about 5% chemical precursors or non-hVR-1, hVR-2, and rVR-2 chemicals.

As used herein, a "biologically active portion" of an hVR-1, hVR-2, and rVR-2 protein includes a fragment of an hVR-1, hVR-2, and rVR-2 protein which participates in an interaction between an hVR-1, hVR-2, and rVR-2 molecule and a non-hVR-1, non-hVR-2, and non-rVR-2 molecule, respectively. Biologically active portions of an hVR-1, hVR-2, and rVR-2 protein include peptides comprising amino acid sequences sufficiently homologous to or derived from the amino acid sequence of the hVR-1, hVR-2, and rVR-2 protein, e.g., the amino acid sequence shown in SEQ ID NO:2, 5, 8, or 11, which include less amino acids than the full length hVR-1, hVR-2, and rVR-2 proteins, and exhibit at least one activity of an hVR-1, hVR-2, and rVR-2 protein. Typically, biologically active portions comprise a domain or motif with at least one activity of the hVR-1, hVR-2, and rVR-2 protein, e.g., binding of an hVR-1, hVR-2, and rVR-2 ligand such as a vanilloid compound, e.g., Capsaicin. A biologically active portion of an hVR-1, hVR-2, and rVR-2 protein can be a polypeptide which is, for example, 10, 20, 30, 40, 50, 60, 70, 80, 90, 100, 200 or more amino acids in length. Biologically active portions of an hVR-1, hVR-2, and rVR-2 protein can be used as targets for developing agents which modulate an hVR-1, hVR-2, and rVR-2 mediated activity, e.g., a pain signaling mechanism.

In one embodiment, a biologically active portion of an hVR-1, hVR-2, and rVR-2 protein comprises at least one transmembrane domain, and/or at least one proline rich domain, and/or at least one ankyrin repeat domain. It is to be understood that a biologically active portion of an hVR-1, hVR-2, and rVR-2 protein of the present invention may contain at least one of the above-identified structural domains. A more biologically active portion of an hVR-1, hVR-2, and rVR-2 protein may contain at least two of the above-identified structural domains. Moreover, other biologically active portions, in which other regions of the protein are deleted, can be prepared by recombinant techniques and evaluated for one or more of the functional activities of a native hVR-1, hVR-2, and rVR-2 protein.

In a embodiment, the hVR-1, hVR-2, and rVR-2 protein has an amino acid sequence shown in SEQ ID NO:2, 5, 8, or 11. In other embodiments, the hVR-1, hVR-2, and rVR-2 protein is substantially homologous to SEQ ID NO:2, 5, 8, or 11, and retains the functional activity of the protein of SEQ ID NO:2, 5, 8, or 11, yet differs in amino acid sequence due to natural allelic variation or mutagenesis, as described in detail in subsection I above. Accordingly, in another embodiment, the hVR-1, hVR-2, and rVR-2 protein is a protein which comprises an amino acid sequence at least about 60%, 65%, 70%, 75%, 80%, 85%, 87%, 90%, 95%, 98% or more homologous to SEQ ID NO:2, 5, 8, or 11.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the hVR-1, hVR-2, and rVR-2 amino acid sequence of SEQ ID NO:2, 5, 8, or 11, having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a embodiment, the percent identity between two amino acid sequences is determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to hVR-1, hVR-2, and rVR-2 nucleic acid molecules of the invention. BLAST protein searches can be performed with the XBLAST program, score=50, wordlength=3 to obtain amino acid sequences homologous to hVR-1, hVR-2, and rVR-2 protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., XBLAST and NBLAST) can be used. See www.ncbi.nlm.nih.gov.

The invention also provides hVR-1, hVR-2, and rVR-2 chimeric or fusion proteins. As used herein, an hVR-1, hVR-2, and rVR-2 "chimeric protein" or "fusion protein" comprises an hVR-1, hVR-2, and rVR-2 polypeptide operatively linked to a non-hVR-1, hVR-2, and rVR-2 polypeptide. An "hVR-1, hVR-2, and rVR-2 polypeptide" refers to a polypeptide having an amino acid sequence corresponding to hVR-1, hVR-2, and rVR-2, whereas a "non-hVR-1, non-hVR-2, and non-rVR-2 polypeptide" refers to a polypeptide having an amino acid sequence corresponding to a protein which is not substantially homologous to the hVR-1, hVR-2, and rVR-2 protein, e.g., a protein which is different from the hVR-1, hVR-2, and rVR-2 protein and which is derived from the same or a different organism. Within an hVR-1, hVR-2, and rVR-2 fusion protein the hVR-1, hVR-2, and rVR-2 polypeptide can correspond to all or a portion of an hVR-1, hVR-2, and rVR-2 protein. In a embodiment, an hVR-1, hVR-2, and rVR-2 fusion protein comprises at least one biologically active portion of an hVR-1, hVR-2, and rVR-2 protein. In another embodiment, an hVR-1, hVR-2, and rVR-2 fusion protein comprises at least two biologically active portions of an hVR-1, hVR-2, and rVR-2 protein. Within the fusion protein, the term "operatively linked" is intended to indicate that the hVR-1, hVR-2, and rVR-2 polypeptide and the non-hVR-1, non-hVR-2, and non-rVR-2 polypeptide are fused in-frame to each other. The non-hVR-1, hVR-2, and rVR-2 polypeptide can be fused to the N-terminus or C-terminus of the hVR-1, hVR-2, and rVR-2 polypeptide.

For example, in one embodiment, the fusion protein is a GST-hVR-1, GST-hVR-2, and GST-rVR-2 fusion protein in which the hVR-1, hVR-2, and rVR-2 sequences are fused to the C-terminus of the GST sequences. Such fusion proteins can facilitate the purification of recombinant hVR-1, hVR-2, and rVR-2.

In another embodiment, the fusion protein is an hVR-1, hVR-2, and rVR-2 protein containing a heterologous signal sequence at its N-terminus. In certain host cells (e.g., mammalian host cells), expression and/or secretion of hVR-1, hVR-2, and rVR-2 can be increased through use of a heterologous signal sequence.

The hVR-1, hVR-2, and rVR-2 fusion proteins of the invention can be incorporated into pharmaceutical compositions and administered to a subject in vivo. The hVR-1, hVR-2, and rVR-2 fusion proteins can be used to affect the bioavailability of an hVR-1, hVR-2, and rVR-2 substrate. Use of hVR-1, hVR-2, and rVR-2 fusion proteins may be useful therapeutically for the treatment of disorders caused by, for example, (i) aberrant modification or mutation of a gene encoding an hVR-1, hVR-2, and rVR-2 protein; (ii) misregulation of the hVR-1, hVR-2, and rVR-2 gene; and (iii) aberrant post-translational modification of an hVR-1, hVR-2, and rVR-2 protein.

Moreover, the hVR-1, hVR-2, and rVR-2-fusion proteins of the invention can be used as immunogens to produce anti-hVR-1, anti-hVR-2, and anti-rVR-2 antibodies in a subject, to purify hVR-1, hVR-2, and rVR-2 ligands and in screening assays to identify molecules which inhibit the interaction of hVR-1, hVR-2, and rVR-2 with an hVR-1, hVR-2, and rVR-2 substrate.

Preferably, an hVR-1, hVR-2, and rVR-2 chimeric or fusion protein of the invention is produced by standard recombinant DNA techniques. For example, DNA fragments coding for the different polypeptide sequences are ligated together in-frame in accordance with conventional techniques, for example by employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An hVR-1, hVR-2, and rVR-2-encoding nucleic acid can be cloned into such an expression vector such that the fusion moiety is linked in-frame to the hVR-1, hVR-2, and rVR-2 protein.

The present invention also pertains to variants of the hVR-1, hVR-2, and rVR-2 proteins which function as either hVR-1, hVR-2, and rVR-2 agonists (mimetics) or as hVR-1, hVR-2, and rVR-2 antagonists. Variants of the hVR-1, hVR-2, and rVR-2 proteins can be generated by mutagenesis, e.g., discrete point mutation or truncation of an hVR-1, hVR-2, and rVR-2 protein. An agonist of the hVR-1, hVR-2, and rVR-2 proteins can retain substantially the same, or a subset, of the biological activities of the naturally occurring form of an hVR-1, hVR-2, and rVR-2 protein. An antagonist of an hVR-1, hVR-2, and rVR-2 protein can inhibit one or more of the activities of the naturally occurring form of the hVR-1, hVR-2, and rVR-2 protein by, for example, competitively modulating an hVR-1, hVR-2, and rVR-2-mediated activity of an hVR-1, hVR-2, and rVR-2 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the hVR-1, hVR-2, and rVR-2 protein.

In one embodiment, variants of an hVR-1, hVR-2, and rVR-2 protein which function as either hVR-1, hVR-2, and rVR-2 agonists (mimetics) or as hVR-1, hVR-2, and rVR-2 antagonists can be identified by screening combinatorial libraries of mutants, e.g., truncation mutants, of an hVR-1, hVR-2, and rVR-2 protein for hVR-1, hVR-2, and rVR-2 protein agonist or antagonist activity. In one embodiment, a variegated library of hVR-1, hVR-2, and rVR-2 variants is generated by combinatorial mutagenesis at the nucleic acid level and is encoded by a variegated gene library. A variegated library of hVR-1, hVR-2, and rVR-2 variants can be produced by, for example, enzymatically ligating a mixture of synthetic oligonucleotides into gene sequences such that a degenerate set of potential hVR-1, hVR-2, and rVR-2 sequences is expressible as individual polypeptides, or alternatively, as a set of larger fusion proteins (e.g., for phage display) containing the set of hVR-1, hVR-2, and rVR-2 sequences therein. There are a variety of methods which can be used to produce libraries of potential hVR-1, hVR-2, and rVR-2 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential hVR-1, hVR-2, and rVR-2 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an hVR-1, hVR-2, and rVR-2 protein coding sequence can be used to generate a variegated population of hVR-1, hVR-2, and rVR-2 fragments for screening and subsequent selection of variants of an hVR-1, hVR-2, and rVR-2 protein. In one embodiment, a library of coding sequence fragments can be generated by treating a double stranded PCR fragment of an hVR-1, hVR-2, and rVR-2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the hVR-1, hVR-2, and rVR-2 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of hVR-1, hVR-2, and rVR-2 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify hVR-1, hVR-2, and rVR-2 variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated hVR-1, hVR-2, and rVR-2 library. For example, a library of expression vectors can be transfected into a cell line, e.g., a neuronal cell line, which ordinarily responds to a particular ligand in an hVR-1, hVR-2, and rVR-2-dependent manner. The transfected cells are then contacted with the ligand and the effect of expression of the mutant on signaling by the ligand can be detected, e.g., by measuring intracellular calcium concentration, neuronal membrane depolarization, or the activity of an hVR-1, hVR-2, and rVR-2-regulated transcription factor. Plasmid DNA can then be recovered from the cells which score for inhibition, or alternatively, potentiation of signaling by the ligand, and the individual clones further characterized.

An isolated hVR-1, hVR-2, and rVR-2 protein, or a portion or fragment thereof, can be used as an immunogen to generate antibodies that bind hVR-1, hVR-2, and rVR-2 using standard techniques for polyclonal and monoclonal antibody preparation. A full-length hVR-1, hVR-2, and rVR-2 protein can be used or, alternatively, the invention provides antigenic peptide fragments of hVR-1, hVR-2, and rVR-2 for use as immunogens. The antigenic peptide of hVR-1, hVR-2, and rVR-2 comprises at least 8 amino acid residues of the amino acid sequence shown in SEQ ID NO:2, 5, 8, or 11 and encompasses an epitope of hVR-1, hVR-2, and rVR-2 such that an antibody raised against the peptide forms a specific immune complex with hVR-1, hVR-2, and rVR-2. Preferably, the antigenic peptide comprises at least 10 amino acid residues, more preferably at least 15 amino acid residues, even more preferably at least 20 amino acid residues, and most preferably at least 30 amino acid residues.

Figure 14:
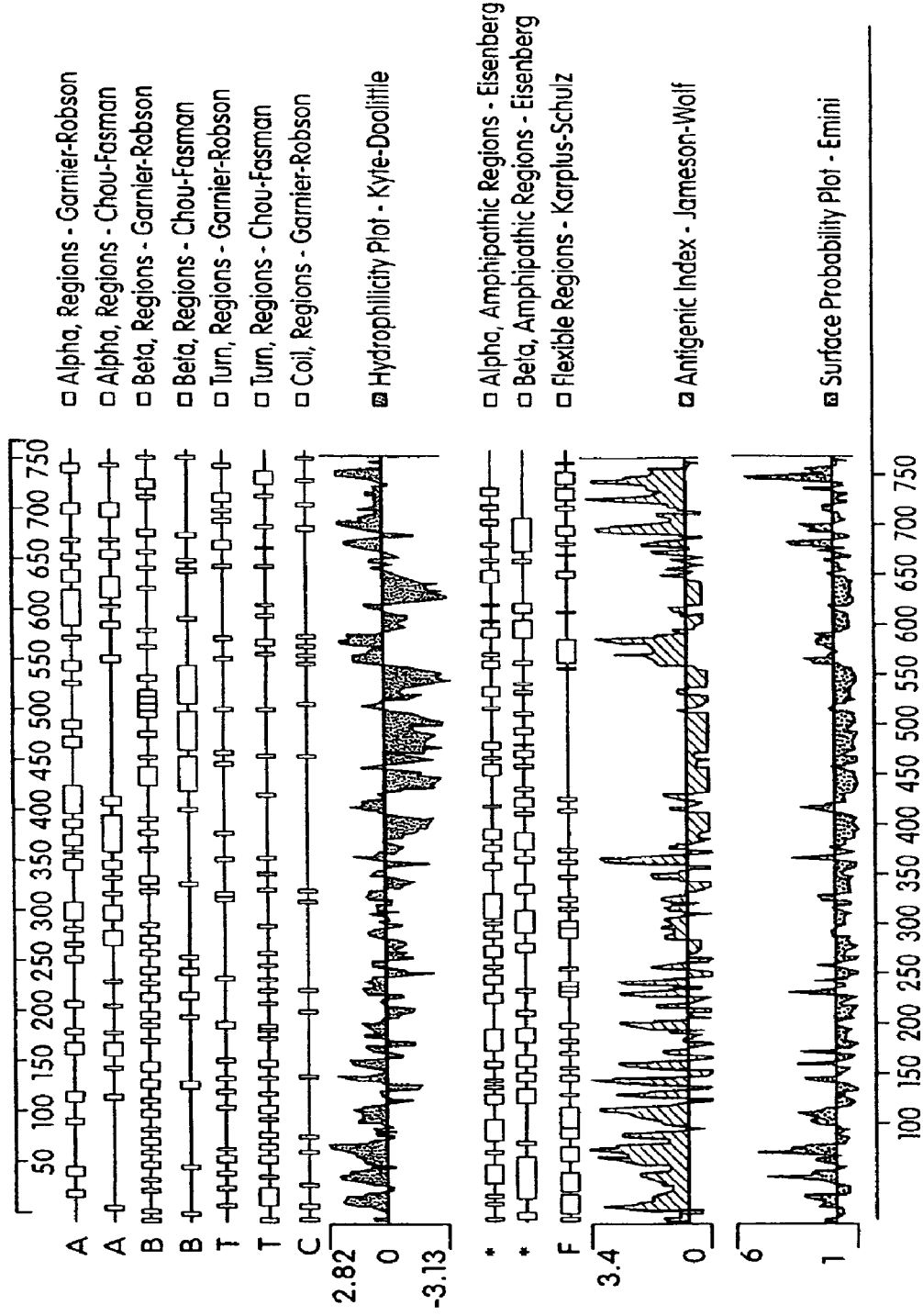
FIG. 14 depicts a structural, hydrophobicity, and antigenicity analysis of the hVR-2 protein.

Epitopes encompassed by the antigenic peptide are regions of hVR-1, hVR-2, and rVR-2 that are located on the surface of the protein, e.g., hydrophilic regions, as well as regions with high antigenicity (see, for example, FIGS. 12 and 14).

An hVR-1, hVR-2, and rVR-2 immunogen typically is used to prepare antibodies by immunizing a suitable subject, (e.g., rabbit, goat, mouse or other mammal) with the immunogen. An appropriate immunogenic preparation can contain, for example, recombinantly expressed hVR-1, hVR-2, and rVR-2 protein or a chemically synthesized hVR-1, hVR-2, and rVR-2 polypeptide. The preparation can further include an adjuvant, such as Freund's complete or incomplete adjuvant, or similar immunostimulatory agent. Immunization of a suitable subject with an immunogenic hVR-1, hVR-2, and rVR-2 preparation induces a polyclonal anti-hVR-1, anti-hVR-2, and anti-rVR-2 antibody response.

Accordingly, another aspect of the invention pertains to anti-hVR-1, anti-hVR-2, and anti-rVR-2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as hVR-1, hVR-2, and rVR-2. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind hVR-1, hVR-2, and rVR-2. The term "monoclonal antibody" or "monoclonal antibody composition", as used herein, refers to a population of antibody molecules that contain only one species of an antigen binding site capable of immunoreacting with a particular epitope of hVR- 1, hVR-2, and rVR-2. A monoclonal antibody composition thus typically displays a single binding affinity for a particular hVR-1, hVR-2, and rVR-2 protein with which it immunoreacts.

Polyclonal anti-hVR-1, anti-hVR-2, and anti-rVR-2 antibodies can be prepared as described above by immunizing a suitable subject with an hVR-1, hVR-2, and rVR-2 immunogen. The anti-hVR-1, anti-hVR-2, and anti-rVR-2 antibody titer in the immunized subject can be monitored over time by standard techniques, such as with an enzyme linked immunosorbent assay (ELISA) using immobilized hVR-1, hVR-2, and rVR-2. If desired, the antibody molecules directed against hVR-1, hVR-2, and rVR-2 can be isolated from the mammal (e.g., from the blood) and further purified by well known techniques, such as protein A chromatography to obtain the IgG fraction. At an appropriate time after immunization, e.g., when the anti-hVR-1, anti-hVR-2, and anti-rVR-2 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387402; M. L. Gefter et al. (1977) *Somatic Cell Genet.* 3:23136). Briefly, an immortal cell line (typically a myeloma) is fused to lymphocytes (typically splenocytes) from a mammal immunized with an hVR-1, hVR-2, and rVR-2 immunogen as described above, and the culture supernatants of the resulting hybridoma cells are screened to identify a hybridoma producing a monoclonal antibody that binds hVR-1, hVR-2, and rVR-2.

Any of the many well known protocols used for fusing lymphocytes and immortalized cell lines can be applied for the purpose of generating an anti-hVR-1, anti-hVR-2, and anti-rVR-2 monoclonal antibodies (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind hVR-1, hVR-2, and rVR-2, e.g., using a standard ELISA assay.

Alternative to preparing monoclonal antibody-secreting hybridomas, a monoclonal anti-hVR-1, anti-hVR-2, and anti-rVR-2 antibody can be identified and isolated by screening a recombinant combinatorial immunoglobulin library (e.g., an antibody phage display library) with hVR-1, hVR-2, and rVR-2 to thereby isolate immunoglobulin library members that bind hVR-1, hVR-2, and rVR-2. Kits for generating and screening phage display libraries are commercially available (e.g., the *Pharmacia Recombinant Phage Antibody System,* Catalog No. 27-9400-01; and the Stratagene *SurfZAP™ Phage Display Kit,* Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-hVR-1, anti-hVR-2, and anti-rVR-2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988)*J. Natl. Cancer Inst.* 80:1553-1559); Morrison, S. L. (1985) *Science* 229:1202-1207; Oi et al., (1986) *BioTechniques* 4:214; Winter U.S. Pat. No. 5,225, 539; Jones et al. (1986) *Nature* 321:552-525; Verhoeyan et al. (1988) *Science* 239:1534; and Beidler et al. (1988) *J. Immunol.* 141:4053-4060.

An anti-hVR-1, anti-hVR-2, and anti-rVR-2 antibody (e.g., monoclonal antibody) can be used to isolate hVR-1, hVR-2, and rVR-2 by standard techniques, such as affinity chromatography or immunoprecipitation. An anti-hVR-1, anti-hVR-2, and anti-rVR-2 antibody can facilitate the purification of natural hVR-1, hVR-2, and rVR-2 from cells and of recombinantly produced hVR-1, hVR-2, and rVR-2 expressed in host cells. Moreover, an anti-hVR-1, anti-hVR-2, and anti-rVR-2 antibody can be used to detect hVR-1, hVR-2, and rVR-2 protein (e.g., in a cellular lysate or cell supernatant) in order to evaluate the abundance and pattern of expression of the hVR-1, hVR-2, and rVR-2 protein. Anti-hVR-1, anti-hVR-2, and anti-rVR-2 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding an hVR-1, hVR-2, and rVR-2 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., hVR-1, hVR-2, and rVR-2 proteins, mutant forms of hVR-1, hVR-2, and rVR-2 proteins, fusion proteins, and the like).

The recombinant expression vectors of the invention can be designed for expression of hVR-1, hVR-2, and rVR-2 proteins in prokaryotic or eukaryotic cells. For example, hVR-1, hVR-2, and rVR-2 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in hVR-1, hVR-2, and rVR-2 activity assays, (e.g., direct assays or competitive assays described in detail below), or to, for example, generate antibodies specific for hVR-1, hVR-2, and rVR-2 proteins. In a embodiment, an hVR-1, hVR-2, and rVR-2 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the hVR-1, hVR-2, and rVR-2 expression vector is a yeast expression vector. Examples of vectors for expression in yeast *S. cerivisae* include pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, hVR-1, hVR-2, and rVR-2 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The expression characteristics of an endogenous hVR-1, hVR-2, and rVR-2 gene within a cell line or microorganism may be modified by inserting a heterologous DNA regulatory element into the genome of a stable cell line or cloned microorganism such that the inserted regulatory element is operatively linked with the endogenous hVR-1, hVR-2, and rVR-2 gene. For example, an endogenous hVR-1, hVR-2, and rVR-2 gene which is normally "trancriptionally silent", i.e., a hVR-1, hVR-2, and rVR-2 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous hVR-1, hVR-2, and rVR-2 gene, may be activated by insertion of a promiscuous regulatory element that works across cell types.

A heterologous regulatory element may be inserted into a stable cell line or cloned microorganism, such that it is operatively linked with an endogenous hVR-1, hVR-2, and rVR-2 gene, using techniques, such as targeted homologous recombination, which are well known to those of skill in the art, and described e.g., in Chappel, U.S. Pat. No. 5,272,071; PCT publication No. WO 91/06667, published May 16, 1991.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to hVR-1, hVR-2, and rVR-2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an hVR-1, hVR-2, and rVR-2 nucleic acid molecule of the invention is introduced, e.g., an hVR-1, hVR-2, and rVR-2 nucleic acid molecule within a recombinant expression vector or an hVR-1, hVR-2, and rVR-2 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an hVR-1, hVR-2, and rVR-2 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. selectable markers include those which confer resistance to drugs, such as G418, hygromycin and methotrexate. Nucleic acid encoding a selectable marker can be introduced into a host cell on the same vector as that encoding an hVR-1, hVR-2, and rVR-2 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an hVR-1, hVR-2, and rVR-2 protein. Accordingly, the invention further provides methods for producing an hVR-1, hVR-2, and rVR-2 protein using the host cells of the invention. In one embodiment, the method comprises culturing the host cell of invention (into which a recombinant expression vector encoding an hVR-1, hVR-2, and rVR-2 protein has been introduced) in a suitable medium such that an hVR-1, hVR-2, and rVR-2 protein is produced. In another embodiment, the method further comprises isolating an hVR-1, hVR-2, and rVR-2 protein from the medium or the host cell.

The host cells of the invention can also be used to produce non-human transgenic animals. For example, in one embodiment, a host cell of the invention is a fertilized oocyte or an embryonic stem cell into which hVR-1, hVR-2, and rVR-2-coding sequences have been introduced. Such host cells can then be used to create non-human transgenic animals in which exogenous hVR-1, hVR-2, and rVR-2 sequences have been introduced into their genome or homologous recombinant animals in which endogenous hVR-1, hVR-2, and rVR-2 sequences have been altered. Such animals are useful for studying the function and/or activity of an hVR-1, hVR-2, and rVR-2 and for identifying and/or evaluating modulators of hVR-1, hVR-2, and rVR-2 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous hVR-1, hVR-2, and rVR-2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an hVR-1, hVR-2, and rVR-2-encoding nucleic acid into the male pronuclei of a fertilized oocyte, e.g., by microinjection, retroviral infection, and allowing the oocyte to develop in a pseudopregnant female foster animal. The hVR-1, hVR-2, and rVR-2 cDNA sequence of SEQ ID NO:1, 3, 5, 7 or 9 can be introduced as a transgene into the genome of a non-human animal. Alternatively, a nonhuman homologue of a hVR-2 gene, such as a mouse or rat hVR-2, e.g., the rVR-2 gene, can be used as a transgene. Alternatively, an hVR-1, hVR-2, and rVR-2 gene homologue, such as another member of the Capsaicin/Vanilloid family, can be isolated based on hybridization to the hVR-1, hVR-2, and rVR-2 cDNA sequences of SEQ ID NO:1, 3, 4, 6, 7, 9, 10, or 12, (described further in subsection I above) and used as a transgene. Intronic sequences and polyadenylation signals can also be included in the transgene to increase the efficiency of expression of the transgene. A tissue-specific regulatory sequence(s) can be operably linked to an hVR-1, hVR-2, and rVR-2 transgene to direct expression of an hVR-1, hVR-2, and rVR-2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an hVR-1, hVR-2, and rVR-2 transgene in its genome and/or expression of hVR-1, hVR-2, and rVR-2 mRNA in tissues or cells of the animals. A transgenic founder animal can then be used to breed additional animals carrying the transgene. Moreover, transgenic animals carrying a transgene encoding an hVR-1, hVR-2, and rVR-2 protein can further be bred to other transgenic animals carrying other transgenes.

To create a homologous recombinant animal, a vector is prepared which contains at least a portion of an hVR-1, hVR-2, and rVR-2 gene into which a deletion, addition or substitution has been introduced to thereby alter, e.g., functionally disrupt, the hVR-1, hVR-2, and rVR-2 gene. The VR-1 or VR-2 gene can be a human gene (e.g., the cDNA of SEQ ID NO:1, 3, 5, 4, 6, 7, or 9), but more preferably, is a non-human homologue of a hVR-1 and hVR-2 gene (e.g., the cDNA of SEQ ID NO:10 or 12, or a cDNA isolated by stringent hybridization with the nucleotide sequence of SEQ ID NO: 1, 3, 5, 4, 6, 7, or 9). For example, a mouse VR-2 gene can be used to construct a homologous recombination nucleic acid molecule, e.g., a vector, suitable for altering an endogenous VR-2 gene in the mouse genome. In a embodiment, the homologous recombination nucleic acid molecule is designed such that, upon homologous recombination, the endogenous hVR-1, hVR-2, and rVR-2 gene is functionally disrupted (i.e., no longer encodes a functional protein; also referred to as a "knock out" vector). Alternatively, the homologous recombination nucleic acid molecule can be designed such that, upon homologous recombination, the endogenous hVR-1, hVR-2, and rVR-2 gene is mutated or otherwise altered but still encodes functional protein (e.g., the upstream regulatory region can be altered to thereby alter the expression of the endogenous hVR-1, hVR-2, and rVR-2 protein). In the homologous recombination nucleic acid molecule, the altered portion of the hVR-1, hVR-2, and rVR-2 gene is flanked at its 5' and 3' ends by additional nucleic acid sequence of the hVR-1, hVR-2, and rVR-2 gene to allow for homologous recombination to occur between the exogenous hVR-1, hVR-2, and rVR-2 gene carried by the homologous recombination nucleic acid molecule and an endogenous hVR-1, hVR-2, and rVR-2 gene in a cell, e.g., an embryonic stem cell. The additional flanking hVR-1, hVR-2, and rVR-2 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced hVR-1, hVR-2, and rVR-2 gene has homologously recombined with the endogenous hVR-1, hVR-2, and rVR-2 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The hVR-1, hVR-2, and rVR-2 nucleic acid molecules, fragments of hVR-1, hVR-2, and rVR-2 proteins, and anti-hVR-1, anti-hVR-2, and anti-rVR-2 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an hVR-1, hVR-2, and rVR-2 protein or an anti-hVR-1, anti-hVR-2, and anti-rVR-2 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein.

When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an hVR-1, hVR-2, and rVR-2 protein of the invention has one or more of the following activities: (1) it interacts with a non-hVR-1, non-hVR-2, and non-rVR-2 protein molecule, e.g., a vanilloid compound such as capsaicin; (2) it modulates intracellular calcium concentration; (3) it activates an hVR-1, hVR-2, and rVR-2-dependent signal transduction pathway; and (4) it modulates a pain signaling mechanism, and, thus, can be used to, for example, (1) modulate the interaction with a non-hVR-1, non-hVR-2, and non-rVR-2 protein molecule; (2) modulate intracellular calcium concentration; (3) activate an hVR-1, hVR-2, and rVR-2-dependent signal transduction pathway; and (4) modulate a pain signaling mechanism.

The isolated nucleic acid molecules of the invention can be used, for example, to express hVR-1, hVR-2, and rVR-2 protein (e.g., via a recombinant expression vector in a host cell in gene therapy applications), to detect hVR-1, hVR-2, and rVR-2 mRNA (e.g., in a biological sample) or a genetic alteration in an hVR-1, hVR-2, and rVR-2 gene, and to modulate hVR-1, hVR-2, and rVR-2 activity, as described further below. The hVR-1, hVR-2, and rVR-2 proteins can be used to screen for naturally occurring hVR-1, hVR-2, and rVR-2 substrates, to screen for drugs or compounds which modulate hVR-1, hVR-2, and rVR-2 activity, as well as to treat disorders characterized by insufficient or excessive production of hVR-1, hVR-2, and rVR-2 protein or production of hVR-1, hVR-2, and rVR-2 protein forms which have decreased or aberrant activity compared to hVR-1, hVR-2, and rVR-2 wild type protein (e.g., pain disorders). Moreover, the anti-hVR-1, anti-hVR-2, and anti-rVR-2 antibodies of the invention can be used to detect and isolate hVR-1, hVR-2, and rVR-2 proteins, regulate the bioavailability of hVR-1, hVR-2, and rVR-2 proteins, and modulate hVR-1, hVR-2, and rVR-2 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to hVR-1, hVR-2, and rVR-2 proteins, have a stimulatory or inhibitory effect on, for example, hVR-1, hVR-2, and rVR-2 expression or hVR-1, hVR-2, and rVR-2 activity, or have a stimulatory or inhibitory effect on, for example, the expression or activity of hVR-1, hVR-2, and rVR-2 substrate.

In one embodiment, the invention provides assays for screening candidate or test compounds which are substrates of an hVR-1, hVR-2, and rVR-2 protein or polypeptide or biologically active portion thereof. In another embodiment, the invention provides assays for screening candidate or test compounds which bind to or modulate the activity of an hVR-1, hVR-2, and rVR-2 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell, e.g., a neuronal cell, which expresses an hVR-1, hVR-2, and rVR-2 protein or biologically active portion thereof is contacted with a test compound and the ability of the test compound to modulate hVR-1, hVR-2, and rVR-2 activity is determined Determining the ability of the test compound to modulate hVR-1, hVR-2, and rVR-2 activity can be accomplished by monitoring, for example, intracellular calcium concentration or membrane depolarization by, e.g., patch-clamp recordings in whole-cell, inside-out, and outside-out configurations (as described in, for example, Tominaga M. et al. (1998) *Neuron* 21:531-543). Determining the ability of the test compound to modulate hVR-1, hVR-2, and rVR-2 activity can further be accomplished by monitoring the activity of an hVR-1, hVR-2, and rVR-2-regulated transcription factor. The cell, for example, can be of mammalian origin, e.g., a neuronal cell.

The ability of the test compound to modulate hVR-1, hVR-2, and rVR-2 binding to a substrate or to bind to hVR-1, hVR-2, and rVR-2 can also be determined Determining the ability of the test compound to modulate hVR-1, hVR-2, and rVR-2 binding to a substrate can be accomplished, for example, by coupling the hVR-1, hVR-2, and rVR-2 substrate with a radioisotope or enzymatic label such that binding of the hVR-1, hVR-2, and rVR-2 substrate to hVR-1, hVR-2, and rVR-2 can be determined by detecting the labeled hVR-1, hVR-2, and rVR-2 substrate in a complex. Determining the ability of the test compound to bind hVR-1, hVR-2, and rVR-2 can be accomplished, for example, by coupling the compound with a radioisotope or enzymatic label such that binding of the compound to hVR-1, hVR-2, and rVR-2 can be determined by detecting the labeled hVR-1, hVR-2, and rVR-2 compound in a complex. For example, compounds (e.g., hVR-1, hVR-2, and rVR-2 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an hVR-1, hVR-2, and rVR-2 substrate) to interact with hVR-1, hVR-2, and rVR-2 without the labeling of any of the interactants. For example, a microphysiometer can be used to detect the interaction of a compound with hVR-1, hVR-2, and rVR-2 without the labeling of either the compound or the hVR-1, hVR-2, and rVR-2. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and hVR-1, hVR-2, and rVR-2.

In yet another embodiment, an assay of the present invention is a cell-free assay in which an hVR-1, hVR-2, and rVR-2 protein or biologically active portion thereof is contacted with a test compound and the ability of the test compound to bind to the hVR-1, hVR-2, and rVR-2 protein or biologically active portion thereof is determined biologically active portions of the hVR-1, hVR-2, and rVR-2 proteins to be used in assays of the present invention include fragments which participate in interactions with non-hVR-1, non-hVR-2, and non-rVR-2 molecules, e.g., fragments with high surface probability scores. Binding of the test compound to the hVR-1, hVR-2, and rVR-2 protein can be determined either directly or indirectly as described above. In a embodiment, the assay includes contacting the hVR-1, hVR-2, and rVR-2 protein or biologically active portion thereof with a known compound which binds hVR-1, hVR-2, and rVR-2 to form an assay mixture, contacting the assay mixture with a test compound, and determining the ability of the test compound to interact with an hVR-1, hVR-2, and rVR-2 protein, wherein determining the ability of the test compound to interact with an hVR-1, hVR-2, and rVR-2 protein comprises determining the ability of the test compound to preferentially bind to hVR-1, hVR-2, and rVR-2 or biologically active portion thereof as compared to the known compound.

In another embodiment, the assay is a cell-free assay in which an hVR-1, hVR-2, and rVR-2 protein or biologically active portion thereof is contacted with a test compound and the ability of the test compound to modulate (e.g., stimulate or inhibit) the activity of the hVR-1, hVR-2, and rVR-2 protein or biologically active portion thereof is determined Determining the ability of the test compound to modulate the activity of an hVR-1, hVR-2, and rVR-2 protein can be accomplished, for example, by determining the ability of the hVR-1, hVR-2, and rVR-2 protein to bind to an hVR-1, hVR-2, and rVR-2 target molecule, e.g., a vanilloid compound such as capsaicin, by one of the methods described above for determining direct binding. Determining the ability of the hVR-1, hVR-2, and rVR-2 protein to bind to an hVR-1, hVR-2, and rVR-2 target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an hVR-1, hVR-2, and rVR-2 protein can be accomplished by determining the ability of the hVR-1, hVR-2, and rVR-2 protein to further modulate the activity of a downstream effector of an hVR-1, hVR-2, and rVR-2 target molecule. For example, the activity of the effector molecule on an appropriate target can be determined or the binding of the effector to an appropriate target can be determined as previously described.

In yet another embodiment, the cell-free assay involves contacting an hVR-1, hVR-2, and rVR-2 protein or biologically active portion thereof with a known compound which binds the hVR-1, hVR-2, and rVR-2 protein to form an assay mixture, contacting the assay mixture with a test compound, and determining the ability of the test compound to interact with the hVR-1, hVR-2, and rVR-2 protein, wherein determining the ability of the test compound to interact with the hVR-1, hVR-2, and rVR-2 protein comprises determining the ability of the hVR-1, hVR-2, and rVR-2 protein to preferentially bind to or modulate the activity of an hVR-1, hVR-2, and rVR-2 target molecule.

The cell-free assays of the present invention are amenable to use of both soluble and/or membrane-bound forms of isolated proteins (e.g., hVR-1, hVR-2, and rVR-2 proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either hVR-1, hVR-2, and rVR-2 or its target molecule to facilitate separation of complexed from uncomplexed forms of one or both of the proteins, as well as to accommodate automation of the assay. Binding of a test compound to an hVR-1, hVR-2, and rVR-2 protein, or interaction of an hVR-1, hVR-2, and rVR-2 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/hVR-1, hVR-2, and rVR-2 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or hVR-1, hVR-2, and rVR-2 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of hVR-1, hVR-2, and rVR-2 binding or activity determined using standard techniques.

Other techniques for immobilizing proteins on matrices can also be used in the screening assays of the invention. For example, either an hVR-1, hVR-2, and rVR-2 protein or an hVR-1, hVR-2, and rVR-2 target molecule can be immobilized utilizing conjugation of biotin and streptavidin. Biotinylated hVR-1, hVR-2, and rVR-2 protein or target molecules can be prepared from biotin-NHS(N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with hVR-1, hVR-2, and rVR-2 protein or target molecules but which do not interfere with binding of the hVR-1, hVR-2, and rVR-2 protein to its target molecule can be derivatized to the wells of the plate, and unbound target or hVR-1, hVR-2, and rVR-2 protein trapped in the wells by antibody conjugation. Methods for detecting such complexes, in addition to those described above for the GST-immobilized complexes, include immunodetection of complexes using antibodies reactive with the hVR-1, hVR-2, and rVR-2 protein or target molecule, as well as enzyme-linked assays which rely on detecting an enzymatic activity associated with the hVR-1, hVR-2, and rVR-2 protein or target molecule.

In another embodiment, modulators of hVR-1, hVR-2, and rVR-2 expression are identified in a method wherein a cell is contacted with a candidate compound and the expression of hVR-1, hVR-2, and rVR-2 mRNA or protein in the cell is determined The level of expression of hVR-1, hVR-2, and rVR-2 mRNA or protein in the presence of the candidate compound is compared to the level of expression of hVR-1, hVR-2, and rVR-2 mRNA or protein in the absence of the candidate compound. The candidate compound can then be identified as a modulator of hVR-1, hVR-2, and rVR-2 expression based on this comparison. For example, when expression of hVR-1, hVR-2, and rVR-2 mRNA or protein is greater (statistically significantly greater) in the presence of the candidate compound than in its absence, the candidate compound is identified as a stimulator of hVR-1, hVR-2, and rVR-2 mRNA or protein expression. Alternatively, when expression of hVR-1, hVR-2, and rVR-2 mRNA or protein is less (statistically significantly less) in the presence of the candidate compound than in its absence, the candidate compound is identified as an inhibitor of hVR-1, hVR-2, and rVR-2 mRNA or protein expression. The level of hVR-1, hVR-2, and rVR-2 mRNA or protein expression in the cells can be determined by methods described herein for detecting hVR-1, hVR-2, and rVR-2 mRNA or protein.

In yet another aspect of the invention, the hVR-1, hVR-2, and rVR-2 proteins can be used as "bait proteins" in a two-hybrid assay or three-hybrid assay (see, e.g., U.S. Pat. No. 5,283,317; Zervos et al. (1993) Cell 72:223-232; Madura et al., (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with hVR-1, hVR-2, and rVR-2 ("hVR-1-binding proteins", "hVR-2-binding proteins", and "rVR-2-binding proteins" or "hVR-1-bp", "hVR-2-bp", and "rVR-2-bp") and are involved in hVR-1, hVR-2, and rVR-2 activity. Such hVR-1, hVR-2, and rVR-2-binding proteins are also likely to be involved in the propagation of signals by the hVR-1, hVR-2, and rVR-2 proteins or hVR-1, hVR-2, and rVR-2 targets as, for example, downstream elements of an hVR-1, hVR-2, and rVR-2-mediated signaling pathway, e.g., a pain signaling pathway. Alternatively, such hVR-1, hVR-2, and rVR-2-binding proteins are likely to be hVR-1, hVR-2, and rVR-2 inhibitors.

The two-hybrid system is based on the modular nature of most transcription factors, which consist of separable DNA-binding and activation domains. Briefly, the assay utilizes two different DNA constructs. In one construct, the gene that codes for an hVR-1, hVR-2, and rVR-2 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an hVR-1, hVR-2, and rVR-2-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the hVR-1, hVR-2, and rVR-2 protein.

This invention further pertains to novel agents identified by the above-described screening assays. Accordingly, it is within the scope of this invention to further use an agent identified as described herein in an appropriate animal model. For example, an agent identified as described herein (e.g., an hVR-1, hVR-2, and rVR-2 modulating agent, an antisense hVR-1, hVR-2, and rVR-2 nucleic acid molecule, an hVR-1, hVR-2, and rVR-2-specific antibody, or an hVR-1, hVR-2, and rVR-2-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the hVR-1, hVR-2, and rVR-2 nucleotide sequences, described herein, can be used to map the location of the hVR-1, hVR-2, and rVR-2 genes on a chromosome. The mapping of the hVR-1, hVR-2, and rVR-2 sequences to chromosomes is an important first step in correlating these sequences with genes associated with disease.

Briefly, hVR-1, hVR-2, and rVR-2 genes can be mapped to chromosomes by preparing PCR primers (preferably 15-25 by in length) from the hVR-1, hVR-2, and rVR-2 nucleotide sequences. Computer analysis of the hVR-1, hVR-2, and rVR-2 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the hVR-1, hVR-2, and rVR-2 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the hVR-1, hVR-2, and rVR-2 nucleotide sequences to design oligonucleotide primers, sublocalization can be achieved with panels of fragments from specific chromosomes. Other mapping strategies which can similarly be used to map an hVR-1, hVR-2, and rVR-2 sequence to its chromosome include in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the hVR-1, hVR-2, and rVR-2 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The hVR-1, hVR-2, and rVR-2 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the hVR-1, hVR-2, and rVR-2 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The hVR-1, hVR-2, and rVR-2 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals.

If a panel of reagents from hVR-1, hVR-2, and rVR-2 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial hVR-1, hVR-2, and rVR-2 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Examples of polynucleotide reagents include the hVR-1, hVR-2, and rVR-2 nucleotide sequences or portions thereof, e.g., fragments derived from SEQ ID NO:1, 3, 4, 6, 7, 9, 10, or 11 having a length of at least 20 bases, preferably at least 30 bases.

The hVR-1, hVR-2, and rVR-2 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such hVR-1, hVR-2, and rVR-2 probes can be used to identify tissue by species and/or by organ type.

In a similar fashion, these reagents, e.g., hVR-1, hVR-2, and rVR-2 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining hVR-1, hVR-2, and rVR-2 protein and/or nucleic acid expression as well as hVR-1, hVR-2, and rVR-2 activity, in the context of a biological sample (e.g., blood, serum, cells, tissue) to thereby determine whether an individual is afflicted with a disease or disorder, or is at risk of developing a disorder, associated with aberrant hVR-1, hVR-2, and rVR-2 expression or activity. The invention also provides for prognostic (or predictive) assays for determining whether an individual is at risk of developing a disorder associated with hVR-1, hVR-2, and rVR-2 protein, nucleic acid expression or activity. For example, mutations in an hVR-1, hVR-2, and rVR-2 gene can be assayed in a biological sample. Such assays can be used for prognostic or predictive purpose to thereby phophylactically treat an individual prior to the onset of a disorder characterized by or associated with hVR-1, hVR-2, and rVR-2 protein, nucleic acid expression or activity.

Another aspect of the invention pertains to monitoring the influence of agents (e.g., drugs, compounds) on the expression or activity of hVR-1, hVR-2, and rVR-2 in clinical trials.

These and other agents are described in further detail in the following sections.

1. Diagnostic Assays

An exemplary method for detecting the presence or absence of hVR-1, hVR-2, and rVR-2 protein or nucleic acid in a biological sample involves obtaining a biological sample from a test subject and contacting the biological sample with a compound or an agent capable of detecting hVR-1, hVR-2, and rVR-2 protein or nucleic acid (e.g., mRNA, genomic DNA) that encodes hVR-1, hVR-2, and rVR-2 protein such that the presence of hVR-1, hVR-2, and rVR-2 protein or nucleic acid is detected in the biological sample. A agent for detecting hVR-1, hVR-2, and rVR-2 mRNA or genomic DNA is a labeled nucleic acid probe capable of hybridizing to hVR-1, hVR-2, and rVR-2 mRNA or genomic DNA. The nucleic acid probe can be, for example, a full-length hVR-1, hVR-2, and rVR-2 nucleic acid, such as the nucleic acid of SEQ ID NO:1, 3, 4, 6, 7, 9, 10, or 12, or a portion thereof, such as an oligonucleotide of at least 15, 30, 50, 100, 250 or 500 nucleotides in length and sufficient to specifically hybridize under stringent conditions to hVR-1, hVR-2, and rVR-2 mRNA or genomic DNA. Other suitable probes for use in the diagnostic assays of the invention are described herein.

An agent for detecting hVR-1, hVR-2, and rVR-2 protein is an antibody capable of binding to hVR-1, hVR-2, and rVR-2 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect hVR-1, hVR-2, and rVR-2 mRNA, protein, or genomic DNA in a biological sample in vitro as well as in vivo. For example, in vitro techniques for detection of hVR-1, hVR-2, and rVR-2 mRNA include Northern hybridizations and in situ hybridizations. In vitro techniques for detection of hVR-1, hVR-2, and rVR-2 protein include enzyme linked immunosorbent assays (ELISAs), Western blots, immunoprecipitations and immunofluorescence. In vitro techniques for detection of hVR-1, hVR-2, and rVR-2 genomic DNA include Southern hybridizations. Furthermore, in vivo techniques for detection of hVR-1, hVR-2, and rVR-2 protein include introducing into a subject a labeled anti-hVR-1, hVR-2, and rVR-2 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A biological sample is a serum sample isolated by conventional means from a subject.

In another embodiment, the methods further involve obtaining a control biological sample from a control subject, contacting the control sample with a compound or agent capable of detecting hVR-1, hVR-2, and rVR-2 protein, mRNA, or genomic DNA, such that the presence of hVR-1, hVR-2, and rVR-2 protein, mRNA or genomic DNA is detected in the biological sample, and comparing the presence of hVR-1, hVR-2, and rVR-2 protein, mRNA or genomic DNA in the control sample with the presence of hVR-1, hVR-2, and rVR-2 protein, mRNA or genomic DNA in the test sample.

The invention also encompasses kits for detecting the presence of hVR-1, hVR-2, and rVR-2 in a biological sample. For example, the kit can comprise a labeled compound or agent capable of detecting hVR-1, hVR-2, and rVR-2 protein or mRNA in a biological sample; means for determining the amount of hVR-1, hVR-2, and rVR-2 in the sample; and means for comparing the amount of hVR-1, hVR-2, and rVR-2 in the sample with a standard. The compound or agent can be packaged in a suitable container. The kit can further comprise instructions for using the kit to detect hVR-1, hVR-2, and rVR-2 protein or nucleic acid.

2. Prognostic Assays

The diagnostic methods described herein can furthermore be utilized to identify subjects having or at risk of developing a disease or disorder associated with aberrant hVR-1, hVR-2, and rVR-2 expression or activity. As used herein, the term "aberrant" includes an hVR-1, hVR-2, and rVR-2 expression or activity which deviates from the wild type hVR-1, hVR-2, and rVR-2 expression or activity. Aberrant expression or activity includes increased or decreased expression or activity, as well as expression or activity which does not follow the wild type developmental pattern of expression or the subcellular pattern of expression. For example, aberrant hVR-1, hVR-2, and rVR-2 expression or activity is intended to include the cases in which a mutation in the hVR-1, hVR-2, and rVR-2 gene causes the hVR-1, hVR-2, and rVR-2 gene to be under-expressed or over-expressed and situations in which such mutations result in a non-functional hVR-1, hVR-2, and rVR-2 protein or a protein which does not function in a wild-type fashion, e.g., a protein which does not interact with an hVR-1, hVR-2, and rVR-2 ligand or one which interacts with a non-hVR-1, non-hVR-2, and non-rVR-2 ligand.

The assays described herein, such as the preceding diagnostic assays or the following assays, can be utilized to identify a subject having or at risk of developing a disorder associated with a misregulation in hVR-1, hVR-2, and rVR-2 protein activity or nucleic acid expression, such as a pain disorder. Alternatively, the prognostic assays can be utilized to identify a subject having or at risk for developing a disorder associated with a misregulation in hVR-1, hVR-2, and rVR-2 protein activity or nucleic acid expression, such as a pain disorder. Thus, the present invention provides a method for identifying a disease or disorder associated with aberrant hVR-1, hVR-2, and rVR-2 expression or activity in which a test sample is obtained from a subject and hVR-1, hVR-2, and rVR-2 protein or nucleic acid (e.g., mRNA or genomic DNA) is detected, wherein the presence of hVR-1, hVR-2, and rVR-2 protein or nucleic acid is diagnostic for a subject having or at risk of developing a disease or disorder associated with aberrant hVR-1, hVR-2, and rVR-2 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant hVR-1, hVR-2, and rVR-2 expression or activity. For example, such methods can be used to determine whether a subject can be effectively treated with an agent for a pain disorder. Thus, the present invention provides methods for determining whether a subject can be effectively treated with an agent for a disorder associated with aberrant hVR-1, hVR-2, and rVR-2 expression or activity in which a test sample is obtained and hVR-1, hVR-2, and rVR-2 protein or nucleic acid expression or activity is detected (e.g., wherein the abundance of hVR-1, hVR-2, and rVR-2 protein or nucleic acid expression or activity is diagnostic for a subject that can be administered the agent to treat a disorder associated with aberrant hVR-1, hVR-2, and rVR-2 expression or activity).

The methods of the invention can also be used to detect genetic alterations in an hVR-1, hVR-2, and rVR-2 gene, thereby determining if a subject with the altered gene is at risk for a disorder characterized by misregulation in hVR-1, hVR-2, and rVR-2 protein activity or nucleic acid expression, such as a neurodegenerative disorder. In embodiments, the methods include detecting, in a sample of cells from the subject, the presence or absence of a genetic alteration characterized by at least one of an alteration affecting the integrity of a gene encoding an hVR-1, hVR-2, and rVR-2-protein, or the misexpression of the hVR-1, hVR-2, and rVR-2 gene. For example, such genetic alterations can be detected by ascertaining the existence of at least one of 1) a deletion of one or more nucleotides from an hVR-1, hVR-2, and rVR-2 gene; 2) an addition of one or more nucleotides to an hVR-1, hVR-2, and rVR-2 gene; 3) a substitution of one or more nucleotides of an hVR-1, hVR-2, and rVR-2 gene, 4) a chromosomal rearrangement of an hVR-1, hVR-2, and rVR-2 gene; 5) an alteration in the level of a messenger RNA transcript of an hVR-1, hVR-2, and rVR-2 gene, 6) aberrant modification of an hVR-1, hVR-2, and rVR-2 gene, such as of the methylation pattern of the genomic DNA, 7) the presence of a non-wild type splicing pattern of a messenger RNA transcript of an hVR-1, hVR-2, and rVR-2 gene, 8) a non-wild type level of an hVR-1, hVR-2, and rVR-2-protein, 9) allelic loss of an hVR-1, hVR-2, and rVR-2 gene, and 10) inappropriate post-translational modification of an hVR-1, hVR-2, and rVR-2-protein. As described herein, there are a large number of assays known in the art which can be used for detecting alterations in an hVR-1, hVR-2, and rVR-2 gene. A biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the hVR-1, hVR-2, and rVR-2-gene (see Abravaya et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to an hVR-1, hVR-2, and rVR-2 gene under conditions such that hybridization and amplification of the hVR-1, hVR-2, and rVR-2-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an hVR-1, hVR-2, and rVR-2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in hVR-1, hVR-2, and rVR-2 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in hVR-1, hVR-2, and rVR-2 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the hVR-1, hVR-2, and rVR-2 gene and detect mutations by comparing the sequence of the sample hVR-1, hVR-2, and rVR-2 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the hVR-1, hVR-2, and rVR-2 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type hVR-1, hVR-2, and rVR-2 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al., (1992) *Methods Enzymol.* 217:286-295. In a embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in hVR-1, hVR-2, and rVR-2 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on an hVR-1, hVR-2, and rVR-2 sequence, e.g., a wild-type hVR-1, hVR-2, and rVR-2 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in hVR-1, hVR-2, and rVR-2 genes. For example, single strand conformation polymorphism (SSCP) may be used to detect differences in electrophoretic mobility between mutant and wild type nucleic acids (orita et al. (1989) *Proc Natl. Acad. Sci. USA:* 86:2766, see also Cotton (1993) *Mutat. Res.* 285:125-144; and Hayashi (1992) *Genet. Anal. Tech. Appl.* 9:73-79). Single-stranded DNA fragments of sample and control hVR-1, hVR-2, and rVR-2 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 by of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an hVR-1, hVR-2, and rVR-2 gene.

Furthermore, any cell type or tissue in which hVR-1, hVR-2, and rVR-2 is expressed may be utilized in the prognostic assays described herein.

3. Monitoring of Effects During Clinical Trials

Monitoring the influence of agents (e.g., drugs) on the expression or activity of an hVR-1, hVR-2, and rVR-2 protein can be applied not only in basic drug screening, but also in clinical trials. For example, the effectiveness of an agent determined by a screening assay as described herein to increase hVR-1, hVR-2, and rVR-2 gene expression, protein levels, or upregulate hVR-1, hVR-2, and rVR-2 activity, can be monitored in clinical trials of subjects exhibiting decreased hVR-1, hVR-2, and rVR-2 gene expression, protein levels, or downregulated hVR-1, hVR-2, and rVR-2 activity. Alternatively, the effectiveness of an agent determined by a screening assay to decrease hVR-1, hVR-2, and rVR-2 gene expression, protein levels, or downregulate hVR-1, hVR-2, and rVR-2 activity, can be monitored in clinical trials of subjects exhibiting increased hVR-1, hVR-2, and rVR-2 gene expression, protein levels, or upregulated hVR-1, hVR-2, and rVR-2 activity. In such clinical trials, the expression or activity of an hVR-1, hVR-2, and rVR-2 gene, and preferably, other genes that have been implicated in, for example, an hVR-1, hVR-2, and rVR-2-associated disorder can be used as a "read out" or markers of the phenotype of a particular cell.

For example, and not by way of limitation, genes, including hVR-1, hVR-2, and rVR-2, that are modulated in cells by treatment with an agent (e.g., compound, drug or small molecule) which modulates hVR-1, hVR-2, and rVR-2 activity (e.g., identified in a screening assay as described herein) can be identified. Thus, to study the effect of agents on hVR-1, hVR-2, and rVR-2-associated disorders (e.g., pain disorders), for example, in a clinical trial, cells can be isolated and RNA prepared and analyzed for the levels of expression of hVR-1, hVR-2, and rVR-2 and other genes implicated in the hVR-1, hVR-2, and rVR-2-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of hVR-1, hVR-2, and rVR-2 or other genes. In this way, the gene expression pattern can serve as a marker, indicative of the physiological response of the cells to the agent. Accordingly, this response state may be determined before, and at various points during treatment of the individual with the agent.

In a embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an hVR-1, hVR-2, and rVR-2 protein, mRNA, or genomic DNA in the preadministration sample; (iii) obtaining one or more post-administration samples from the subject; (iv) detecting the level of expression or activity of the hVR-1, hVR-2, and rVR-2 protein, mRNA, or genomic DNA in the post-administration samples; (v) comparing the level of expression or activity of the hVR-1, hVR-2, and rVR-2 protein, mRNA, or genomic DNA in the pre-administration sample with the hVR-1, hVR-2, and rVR-2 protein, mRNA, or genomic DNA in the post administration sample or samples; and (vi) altering the administration of the agent to the subject accordingly. For example, increased administration of the agent may be desirable to increase the expression or activity of hVR-1, hVR-2, and rVR-2 to higher levels than detected, i.e., to increase the effectiveness of the agent. Alternatively, decreased administration of the agent may be desirable to decrease expression or activity of hVR-1, hVR-2, and rVR-2 to lower levels than detected, i.e. to decrease the effectiveness of the agent. According to such an embodiment, hVR-1, hVR-2, and rVR-2 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant hVR-1, hVR-2, and rVR-2 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the hVR-1, hVR-2, and rVR-2 molecules of the present invention or hVR-1, hVR-2, and rVR-2 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant hVR-1, hVR-2, and rVR-2 expression or activity, by administering to the subject an hVR-1, hVR-2, and rVR-2 or an agent which modulates hVR-1, hVR-2, and rVR-2 expression or at least one hVR-1, hVR-2, and rVR-2 activity. Subjects at risk for a disease which is caused or contributed to by aberrant hVR-1, hVR-2, and rVR-2 expression or activity can be identified by, for example, any or a combination of diagnostic or prognostic assays as described herein. Administration of a prophylactic agent can occur prior to the manifestation of symptoms characteristic of the hVR-1, hVR-2, and rVR-2 aberrancy, such that a disease or disorder is prevented or, alternatively, delayed in its progression. Depending on the type of hVR-1, hVR-2, and rVR-2 aberrancy, for example, an hVR-1, hVR-2, and rVR-2, hVR-1, hVR-2, and rVR-2 agonist or hVR-1, hVR-2, and rVR-2 antagonist agent can be used for treating the subject. The appropriate agent can be determined based on screening assays described herein.

2. Therapeutic Methods

Another aspect of the invention pertains to methods of modulating hVR-1, hVR-2, and rVR-2 expression or activity for therapeutic purposes. Accordingly, in an exemplary embodiment, the modulatory method of the invention involves contacting a cell with an hVR-1, hVR-2, and rVR-2 or agent that modulates one or more of the activities of hVR-1, hVR-2, and rVR-2 protein activity associated with the cell. An agent that modulates hVR-1, hVR-2, and rVR-2 protein activity can be an agent as described herein, such as a nucleic acid or a protein, a naturally-occurring target molecule of an hVR-1, hVR-2, and rVR-2 protein (e.g., an hVR-1, hVR-2, and rVR-2 substrate), an hVR-1, hVR-2, and rVR-2 antibody, an hVR-1, hVR-2, and rVR-2 agonist or antagonist, a peptidomimetic of an hVR-1, hVR-2, and rVR-2 agonist or antagonist, or other small molecule. In one embodiment, the agent stimulates one or more hVR-1, hVR-2, and rVR-2 activities. Examples of such stimulatory agents include active hVR-1, hVR-2, and rVR-2 protein and a nucleic acid molecule encoding hVR-1, hVR-2, and rVR-2 that has been introduced into the cell. In another embodiment, the agent inhibits one or more hVR-1, hVR-2, and rVR-2 activities. Examples of such inhibitory agents include antisense hVR-1, hVR-2, and rVR-2 nucleic acid molecules, anti-hVR-1, hVR-2, and rVR-2 antibodies, and hVR-1, hVR-2, and rVR-2 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an hVR-1, hVR-2, and rVR-2 protein or nucleic acid molecule. In one embodiment, the method involves administering an agent (e.g., an agent identified by a screening assay described herein), or combination of agents that modulates (e.g., upregulates or downregulates) hVR-1, hVR-2, and rVR-2 expression or activity. In another embodiment, the method involves administering an hVR-1, hVR-2, and rVR-2 protein or nucleic acid molecule as therapy to compensate for reduced or aberrant hVR-1, hVR-2, and rVR-2 expression or activity.

Stimulation of hVR-1, hVR-2, and rVR-2 activity is desirable in situations in which hVR-1, hVR-2, and rVR-2 is abnormally downregulated and/or in which increased hVR-1, hVR-2, and rVR-2 activity is likely to have a beneficial effect. For example, stimulation of hVR-1, hVR-2, and rVR-2 activity is desirable in situations in which an hVR-1, hVR-2, and rVR-2 is downregulated and/or in which increased hVR-1, hVR-2, and rVR-2 activity is likely to have a beneficial effect. Likewise, inhibition of hVR-1, hVR-2, and rVR-2 activity is desirable in situations in which hVR-1, hVR-2, and rVR-2 is abnormally upregulated and/or in which decreased hVR-1, hVR-2, and rVR-2 activity is likely to have a beneficial effect.

3. Pharmacogenomics

The hVR-1, hVR-2, and rVR-2 molecules of the present invention, as well as agents, or modulators which have a stimulatory or inhibitory effect on hVR-1, hVR-2, and rVR-2 activity (e.g., hVR-1, hVR-2, and rVR-2 gene expression) as identified by a screening assay described herein can be administered to individuals to treat (prophylactically or therapeutically) hVR-1, hVR-2, and rVR-2-associated disorders (e.g., pain disorders) associated with aberrant hVR-1, hVR-2, and rVR-2 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an hVR-1, hVR-2, and rVR-2 molecule or hVR-1, hVR-2, and rVR-2 modulator as well as tailoring the dosage and/or therapeutic regimen of treatment with an hVR-1, hVR-2, and rVR-2 molecule or hVR-1, hVR-2, and rVR-2 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an hVR-1, hVR-2, and rVR-2 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an hVR-1, hVR-2, and rVR-2 molecule or hVR-1, hVR-2, and rVR-2 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an hVR-1, hVR-2, and rVR-2 molecule or hVR-1, hVR-2, and rVR-2 modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Identification and Characterization of hVR-1, hVR-2, and rVR-2 cDNA

In this example, the identification and characterization of the genes encoding hVR-1 (clone Fchrb87a6), hVR-2 (clone flh21e11), hVR-2 alternate form (clone frhob12c4), and rVR-2 (clone flrxb147g11) are described.

Isolation of the hVR-1, hVR-2, and the rVR-2 cDNA

The invention is based, at least in part, on the discovery of two human genes and one rat gene encoding novel members of the Capsaicin/Vanilloid receptor family, referred to herein as hVR-1, hVR-2, and rVR-2, respectively. These clones were identified from a human heart library and a rat dorsal root ganglion (DRG) library, based on sequence homology to the known rat VR-1 (Accession Number AF029310). The sequence of the two human clones and the rat clone was determined and found to contain open reading frames.

The nucleotide sequence of the full length hVR-1 cDNA and the predicted amino acid sequence of the hVR-1 polypeptide are shown in FIGS. 1A-1D and in SEQ ID NOS:1 and 2, respectively.

The nucleotide sequence of the full length hVR-2 cDNA and the predicted amino acid sequence of the hVR-2 polypeptide are shown in FIGS. 2A-2B and in SEQ ID NOS:4 and 5, respectively.

The nucleotide sequence of the partial hVR-2 (alternate form) cDNA and the predicted amino acid sequence of the hVR-2 (alternate form) polypeptide are shown in FIGS. 3A-3B and in SEQ ID NOS:7 and 8, respectively.

The amino acid sequence of the predicted full length human VR-2 protein (alternate form) is shown in FIG. 16 and in SEQ ID NO:20.

The nucleotide sequence of the partial rVR-2 cDNA and the predicted amino acid sequence of the rVR-2 polypeptide are shown in FIGS. 4A-4B and in SEQ ID NOS:10 and 11, respectively.

Analysis of the hVR-1, hVR-2, and rVR-2 Molecules

The hVR-1 protein (SEQ ID NO:2) was aligned with the human VR-2 protein (SEQ ID NO:5) using the GAP program in the GCG software package (Blosum 62 matrix) and a gap weight of 12 and a length weight of 4. The results showed a 46.348% identity and 55.378% similarity between the two sequences (see FIGS. 5A-5B).

The hVR-1 nucleotide sequence (SEQ ID NO:1) was aligned with the human VR-2 nucleotide sequence (SEQ ID NO:4) using the GAP program in the GCG software package (nwsgapdna matrix) and a gap weight of 50 and a length weight of 3. The results showed a 55.316% identity and 55.316% similarity between the two sequences (see FIGS. 6A-6F).

The hVR-2 protein (SEQ ID NO:5) was aligned with the rat VR-2 protein (SEQ ID NO:11) using the CLUSTAL W (1.74) multiple sequence alignment program (FIG. 7), as well as using the GAP program in the GCG software package (Blosum 62 matrix) and a gap weight of 12 and a length weight of 4. The results showed a 79.167% identity and 81.703% similarity between the two sequences (see FIGS. 8A-8B).

The hVR-1 nucleotide sequence (SEQ ID NO:1) was aligned with the rat VR-1 nucleotide sequence (Accession Number: AF029310, SEQ ID NO:21) using the GAP program in the GCG software package (nwsgapdna matrix) and a gap weight of 50 and a length weight of 3. The results showed a 82.125% identity and 82.125% similarity between the two sequences (see FIGS. 9A-9F).

The hVR-1 protein (SEQ ID NO:2) was aligned with the rat VR-1 protein (Accession Number: AF029310, SEQ ID NO:22) using the GAP program in the GCG software package (Blosum 62 matrix) and a gap weight of 12 and a length weight of 4. The results showed a 86.022% identity and 89.247% similarity between the two sequences (see FIGS. 10A-10B).

The hVR-2 protein (SEQ ID NO:5) was aligned with the human VR-2 protein (alternate form) (SEQ ID NO:8) using the CLUSTAL W (1.74) multiple sequence alignment program (FIG. 11).

Finally, the hVR-2 protein (SEQ ID NO:5) was aligned with the predicted full length human VR-2 protein (alternate form) (SEQ ID NO:20) using the CLUSTAL W (1.74) multiple sequence alignment program (FIG. 17).

A search was performed against the HMM database resulting in the identification of three ankyrin repeat domains in the amino acid sequence of hVR-1 (SEQ ID NO:2) at about residues 201-233, 248-283, and 333-361, and in the amino acid sequence of hVR-2 (SEQ ID NO:5) at about residues 162-194, 208-243, and 293-328. The results of the searches are set forth in FIGS. 13 and 15, respectively.

Hydropathy plots have identified 6 transmembrane domains in the hVR-1 and the hVR-2 proteins (see FIGS. 12 and 14, respectively).

A series of searches have revealed that the hVR-1 protein matches the ProDom entry 141801 for the vanilloid receptor subtype and the ProDom entry 145518 for the vanilloid receptor subtype.

Moreover, a search was performed against the Prosite database resulting in the identification of four N-glycosylation sites in the amino acid sequence of SEQ ID NO:5 (at about residues 171-174, 192-195, 604-607, and 749-752), three cGMP-dependent protein kinase phosphorylation sites in the amino acid sequence of SEQ ID NO:5 (at about residues 2-5, 368-371, and 499-502), a series of protein kinase C and Casein kinase II phosphorylation sites in the amino acid sequence of SEQ ID NO:5, two tyrosine kinase phosphorylation sites in the amino acid sequence of SEQ ID NO:5 (at about residues 368-375 and 622-628), and two myristoylation sites in the amino acid sequence of SEQ ID NO:5 (at about residues 169-174 and 765-770).

Tissue Distribution of hVR-1 and hVR-2 mRNA

This Example describes the tissue distribution of hVR-1 and hVR-2 mRNA as determined by in situ hybridization.

For in situ analysis, tissues, such as brain regions and whole brain, obtained from human and monkey were first frozen on dry ice. Ten-micrometer-thick coronal sections of the tissues were postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

The data indicate that the hVR-1 molecule is not expressed in human nor monkey brain. The hVR-1 molecule is expressed in nodose, trigeminal sensory neurons, but is not expressed in sympathetic neurons. Within the nodose sensory neurons and trigeminal sensory neurons, expression was seen in distinct sub-populations. Moreover, hVR1 is expressed in some, but not all, small dorsal root ganglion (DRG) neurons and in a few medium sized DRG neurons. The hVR-1 molecule is partially co-expressed with the neuropeptide CGRP and with substance P which are present in nociceptive neurons.

The data further indicate that the VR-2 molecule is expressed in both human and monkey brain, primarily in cortical neurons. The VR2 molecule is also expressed in other brain regions, for example, the thalamus, striatum, hippocampus, hypothalamus, midbrain, medula and brain stem. In addition, the VR-2 molecule is expressed in parasympathetic neurons of the monkey heart (atrium), nodose sensory neurons, trigeminal (TRG) sensory neurons, dorsal root ganglion sensory neurons, sympathetic neurons, and motor neurons of the spinal cord. The VR2 molecule is widely expressed in TRG and DRG neurons, being present in most small and medium sized neurons and also in a few of the large neurons. VR2, like VR-1, partially co-localizes with CGRP and substance P.

Trigeminal sensory neurons are recognized pain centers while sympathetic neurons have been shown to be involved in neuropathic pain.

Example 2

Expression of Recombinant hVR-1, hVR-2, and rVR-2 Protein In Bacterial Cells

In this example, hVR-1, hVR-2, and rVR-2 is expressed as a recombinant glutathione-S-transferase (GST) fusion polypeptide in *E. coli* and the fusion polypeptide is isolated and characterized. Specifically, hVR-1, hVR-2, and rVR-2 is fused to GST and this fusion polypeptide is expressed in *E. coli*, e.g., strain PEB199. Expression of the GST-hVR-1, GST-hVR-2, and GST-rVR-2 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant hVR-1, hVR-2, and

To express the hVR-1, hVR-2, and rVR-2 gene in COS cells, the pcDNA/Amp vector from Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire hVR-1, hVR-2, and rVR-2 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the hVR-1, hVR-2, and rVR-2 DNA sequence is amplified by PCR using two primers. The 5' primer contains the restriction site of interest followed by approximately twenty nucleotides of the hVR-1, hVR-2, and rVR-2 coding sequence starting from the initiation codon; the 3' end sequence contains complementary sequences to the other restriction site of interest, a translation stop codon, the HA tag or FLAG tag and the last 20 nucleotides of the hVR-1, hVR-2, and rVR-2 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the hVR-1, hVR-2, and rVR-2 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the hVR-1, hVR-2, and rVR-2-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the hVR-1, hVR-2, and rVR-2 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the hVR-1, hVR-2, and rVR-2 coding sequence is cloned directly into the polylinker of the pCDNA/Amp vector using the appropriate restriction sites. The resulting plasmid is transfected into COS cells in the manner described above, and the expression of the hVR-1, hVR-2, and rVR-2 polypeptide is detected by radiolabelling and immunoprecipitation using an hVR-1, hVR-2, and rVR-2 specific monoclonal antibody.

Example 4

Electrophysiological Studies of VR2

Human VR2 was functionally characterized in both HEK293 cells and *Xenopus* oocytes using electrophysiological methods. VR2 (in the pcDNA3.1 vector purchased by Invitrogen) was transiently expressed in HEK293 cells (ATCC) and recordings were performed 48 hours after transfection of cells using the whole-cell patch-clamp method (described in Bertil Hille, Ionin Channels of excitable membranes, 1992; Hammill et al. (1981) *Pluger Arch.* 391:85-100). The results indicate that heat stimulation (>50° C.) induces a rapid inactivating inward current (1-2 nA). Heat-evoked currents of VR2 displayed profound desensitization and could be reversibly blocked by the VR1 inhibitor capsazepin (at a 10 µM concentration). In contrast to rat VR1, Capsaicin (at a 1-10 µM concentration), resiniferatoxin (at a 0.1-3 µM concentration), and low pH (5.0-6.0) do not induce any currents from VR2. Binding studies of [$^3$H]-resiniferatoxin (NEN) to both human VR1 and VR2 in membranes isolated from HEK293 cell homogenates also indicate that resiniferatoxin (at a 0.1-10 nM concentration) has no specific binding to VR2 while it binds to human VR1 with high affinities.

For the oocyte studies, human VR2 was subcloned into an oocyte expression vector containing 5'- and 3'-UTR of *Xenopus* β-globin (Chiara et al. (1999) *Biochemistry* 38(20)6689-6698). In vitro transcription was carried out as described in Chiara et al. (supra) and cRNA (10-100 ng) was then injected into the oocytes. VR2 function was characterized in the oocytes 48 hours after cRNA injection using a standard two-electrode voltage-clamp. Consistent with the data from the HEK293 studies, VR2 can only be activated by heat stimulation (48-50° C.) but not by vanilloid receptor agonists, capsaicin, or resiniferatoxin. The vanilloid receptor antagonist capsazepine (at a 1-10 µM concentration) blocks the heat response of VR2 reversibly.

Example 5

Generation of Anti-hVR-2 Antibodies and hVR-2 Protein Localization by Immunostaining Polyclonal antisera were raised in rabbits against the following three peptides derived from the human VR2 amino acid sequence, using the techniques described in Ed Harlow and David Lane (1988) "Antibodies; A Laboratory Manual" Cold Spring harbor Laboratory Press.

```
Antibody PEPTIDE 1:
AFHCKSPHRHRMVVLE             (SEQ ID NO: 13)

Antibody PEPTIDE 2:
RPEAPTGPNATESVQPMEGQEDEGN    (SEQ ID NO: 14)

Antibody PEPTIDE 3:
SVLEMENGYWWCRKKQRAG          (SEQ ID NO: 15)
```

Antisera were subsequently affinity purified using the peptide immunogen.

The polyclonal antisera were tested for immunostaining of both monkey and rat dorsal root ganglion sensory neurons. Peptides 1 and 3 gave specific staining of subpopulations of sensory neurons that was competed with the corresponding peptide. This pattern of expression was very similar to the one observed using a VR-2 riboprobe.

Example 6

Chromosomal Localization of hVR-1 and hVR-2

To chromosomally map the hVR-1 gene, primers were designed based on the sequence of hVR-1 (clone Fchrb87a6) (amplifying a 177 by product from a human control cell line DNA and multiple faint larger products from a control Hamster cell line DNA by PCR). These primers were used to amplify 93 DNAs in duplicate from the Genebridge 4 Radiation Hybrid Panel (Research Genetics, Inc., Huntsville, Ala.).

The hVR-1 primers used in the PCR mapping studies were: forward-TAGGAGACCCCGTTGCCACG (SEQ ID NO:16) and reverse-GATTCACTTGGGGACAGTGACG (SEQ ID NO:17) and the PCR reactions were performed as follows: 5 µl Template DNA (10 ng/µl), 1.5 µl 10× Perkin Elmer PCR Buffer, 1.2 µl Pharmacia dNTP mix 2.5 mM, 1.15 µl Forward primer 6.6 µM, 1.15 µl Reverse primer 6.6 µM, 5 µl Gibco/BRL Platinum Taq 0.05 U/µl (Hot Start), using an amplification profile of: 95° C. for 10 minutes followed by 35 Cycles of 94° C. for 40 seconds, 55° C. for 40 seconds, 72° C. for 40 seconds, and 72° C. for 5 minutes. The PCR products were run on 2% agarose gels, post-stained with SYBR Gold (1:10,000 dilution in 1×TBE), and scanned on a Molecular Dynamics 595 Fluorimager.

The following is the vector data for the 93 Genebridge4 hybrid DNAs. These are in order 1-93. A "1" is a positive result, a "−" is a negative result, a "?" is an ambiguous result.
hVR1 1 − − 1 ? − 1 − 1 − 1 1 − − − 1 − − 1 − 1 1 − − 1 − 1 − 1 − − 1 1 − 1 − − − − − − − − 1 − 1 1 1 − − − 1 − − − 1 1 − − − − 1 − − − − − 1 − 1 − − 1 1 1 − 1 − 1 − − − 1 1 − 1 − − − − − − − − 1

RH linkage analysis was performed using the Map Manager QTb28 software package.

hVR1 was found to map to the p arm of human chromosome 17, 18.9 cR$_{3000}$ telomeric to the Whitehead Institute framework marker WI-6584, and 7.7 cR$_{3000}$ centromeric of the Whitehead framework marker WI-5436. LOD scores for linkage were 14.5 for WI-6584 and 19.3 for WI-5436. This region corresponds to the cytogenetic location 17p12-13. This region is syntenic to mouse chromosome 11.

To chromosomally map the hVR-2 gene, primers were designed from 5' UTR sequence of human VR2 (clone Flh21e11) (amplifying a 166 by product from a human control cell line DNA and 2 much larger faint bands from a control Hamster cell line DNA by PCR). These primers were used to amplify 93 DNAs in duplicate from the Genebridge 4 Radiation Hybrid Panel (Research Genetics, Inc., Huntsville, Ala.).

The hVR-2 primers used in the PCR mapping studies were: forward-TTAAGCTCCCGTTCTCACCG (SEQ ID NO:18) and reverse-GCTGCGGGAGGAAGTGAAGC (SEQ ID NO:19) and the PCR reactions were performed as follows: 5 µl Template DNA (10 ng/µl), 1.5 µl 10× Perkin Elmer PCR Buffer, 1.2 µl Pharmacia dNTP mix 2.5 mM, 1.15 µl Forward primer 6.6 µM, 1.15 µl Reverse primer 6.6 µM, 5 µl Gibco/BRL Platinum Taq 0.05 U/µl (Hot Start), using an amplification profile of 95° C. for 10 minutes, followed by 35 Cycles of 94° C. for 40 seconds, 55° C. for 40 seconds, 72° C. for 40 seconds, and 72° C. for 5 minutes. The PCR products were run on 2% agarose gels, post-stained with SYBR Gold (1:10,000 dilution in 1×TBE), and scanned on a Molecular Dynamics 595 Fluorimager.

The following is the vector data for the 93 Genebridge4 hybrid DNAs. These are in order 1-93. A "1" is a positive result, a "−" is a negative result, a "?" is an ambiguous result.
hVR2 1 − − 1 1 − ? 1 1 − − − − − − 1 − − 1 − 1 1 − − − − − 1 − 1 1 1 1 − − − 1 − − − − − − 1 1 − 1 1 1 − − 1 1 − − − 1 1 − − − − 1 1 1 − − − 1 − 1 1 − 1 − 1 1 1 1 1 − − − 1 1 − 1 − 1 − ? − − − ?

RH linkage analysis was performed using the Map Manager QTb28 software package.

hVR2 was found to map to the p arm of human chromosome 17, 29.3cR cR$_{3000}$ telomeric to the Whitehead Institute framework marker D17S721, and 23.3 cR$_{3000}$ centromeric of the Whitehead framework marker AFMA043ZB5. LOD scores for linkage were 11.9 for D17S721 and 13.6 for AFMA043ZB5. This region corresponds to the cytogenetic location 17p11-12. This region is syntenic to mouse chromosome 11.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated nucleic acid molecule which encodes a polypeptide selected from the group consisting of
   (1) a polypeptide comprising the amino acid sequence set forth in SEQ ID NO:2;
   (2) a polypeptide consisting of the amino acid sequence set forth in SEQ ID NO:2;
   (3) a polypeptide comprising an amino acid sequence at least about 87% identical to the amino acid sequence of SEQ ID NO:2; and
   (4) a polypeptide comprising at least 200 contiguous amino acid residues of the amino acid sequence of SEQ ID NO:2.

2. The isolated nucleic acid molecule of claim 1 further comprising a nucleotide sequence encoding a heterologous polypeptide.

3. The isolated nucleic acid molecule of claim 1 which is a vector.

4. The isolated nucleic acid molecule of claim 3 which is an expression vector.

5. The isolated nucleic acid molecule of claim 1 which comprises SEQ ID NO:1.

6. The isolated nucleic acid molecule of claim 3 which comprises SEQ ID NO:1.

7. The isolated nucleic acid molecule of claim 4 which comprises SEQ ID NO:1.

8. A host cell transfected with an expression vector which comprises a nucleic acid molecule which encodes a polypeptide selected from the group consisting of (1) a polypeptide comprising the amino acid sequence set forth in SEQ ID NO:2; (2) a polypeptide consisting of the amino acid sequence set forth in SEQ ID NO:2; (3) a polypeptide comprising an amino acid sequence at least about 87% identical to the amino acid sequence of SEQ ID NO:2; and (4) a polypeptide comprising at least 200 contiguous amino acid residues of the amino acid sequence of SEQ ID NO:2.

9. The host cell of claim 8, wherein the expression vector comprises SEQ ID NO:1.

10. A method, comprising culturing a host cell in an appropriate culture medium, wherein the host cell comprises an expression vector and wherein the expression vector comprises a nucleic acid molecule which encodes a polypeptide selected from the group consisting of (1) a polypeptide comprising the amino acid sequence set forth in SEQ ID NO:2; (2) a polypeptide consisting of the amino acid sequence set forth in SEQ ID NO:2; (3) a polypeptide comprising an amino acid sequence at least about 87% identical to the amino acid sequence of SEQ ID NO:2; and (4) a polypeptide comprising at least 200 contiguous amino acid residues of the amino acid sequence of SEQ ID NO:2, thereby expressing the polypeptide encoded by the nucleic acid molecule.

11. The method of claim 10 wherein the nucleic acid molecule comprises SEQ ID NO:1.

* * * * *

SEQUENCE LISTING

<160> NUMBER OF SEQ ID NOS: 20

<210> SEQ ID NO 1
<211> LENGTH: 3909
<212> TYPE: DNA
<213> ORGANISM: Homo sapiens
<220> FEATURE:
<221> NAME/KEY: CDS
<222> LOCATION: (1113)..(3629)

<400> SEQUENCE: 1

```
gtgagcgcaa cgcactgcgg gcagtgagcg caacgcactg cgggcagtga gcgcaacgca      60
ctgcgggcag tgagcgcaac gcactgcggg cagtgagcgc aacgcactgc gggcagtgag     120
cgcaacgcac tgcgggcagt gagcgcaacg cactgcgggc agtgagcgca acgcacttgc     180
gggcagtgag cgcaacgcac tgcgggcagt gagcgcaacg cactgcgggc agtgagcgca     240
acgcactgcg gcagtgagc gcaacgcact gcggcagtg agcgcaacgc actgcgggca     300
gtgagcgcaa cgcactgcgg gcagtgagcg caacgcactg cgggcagtga gcgcaacgca     360
ctgcgggcag tgagcgcaac gcactgcggg cagtgagcgc aacgcactgc gggcagtgag     420
cgcaacgcac ttaatgtgag ttagctcact cattaggcac cccaggcttt acactttatg     480
cttccggctc gtatgttgtg tggaattgtg agcggataac aatttcacac aggaaacagc     540
tatgaccatg attacgccaa gctctaatac gactcactat agggaaagct ggtacgcctg     600
caggtaccgg tccggaattc ccgggtcgac ccacgcgtcc gaaaacacac ctctctgctg     660
tgggaagact gtgcaatggc acagccgcag agcttggttt gggaggttga agtgctctgg     720
ggagaattcg tagatcatcc tcagaaaagc cttgccctgg tgttctacca gaaaaacgtc     780
tcccaatcac ccagaaaagc tgtccacagt agtccccct tatccacggg tgtcactttc     840
catgggttca gttatttgcg gtcaaccacg gtctgccaat attaaatgga aaattcttca     900
aacagttccc aagttttccc ttgtgcattg ttctgagcag tgtgatgaag agtctctgcc     960
gtgccatctg ggatgcaaac cgtccctgtg tcccccacgt ccaggccgta gatgctcccc    1020
gccggtcagt cacttagtcg tcagatcgcc cgtcctggta tcacagtgct tctgttcagg    1080
ttgcacactg ggccacagag gatccagcaa gg atg aag aaa tgg agc agc aca    1133
                                    Met Lys Lys Trp Ser Ser Thr
                                    1               5 gac ttg ggg aca gct gcg gac cca ctc caa aag gac acc tgc cca gac    1181
Asp Leu Gly Thr Ala Ala Asp Pro Leu Gln Lys Asp Thr Cys Pro Asp
            10                  15                  20 ccc ctg gat gga gac cct aac tcc agg cca cct cca gcc aag ccc cag    1229
Pro Leu Asp Gly Asp Pro Asn Ser Arg Pro Pro Pro Ala Lys Pro Gln
        25                  30                  35 ctc ccc acg gcc aag agc cgc acc cgg ctc ttt ggg aag ggt gac tcg    1277
Leu Pro Thr Ala Lys Ser Arg Thr Arg Leu Phe Gly Lys Gly Asp Ser
    40                  45                  50                  55 gag gag gct ttc ccg gtg gat tgc ccc cac gag gaa ggt gag ttg gac    1325
Glu Glu Ala Phe Pro Val Asp Cys Pro His Glu Glu Gly Glu Leu Asp
                60                  65                  70 tcc tgc ccg acc atc aca gtc agc cct gtt atc acc atc cag agg cca    1373
Ser Cys Pro Thr Ile Thr Val Ser Pro Val Ile Thr Ile Gln Arg Pro
            75                  80                  85 gga gac ggc ccc acc ggt gcc agg ctg ctg tcc cag gac tct gtc gcc    1421
Gly Asp Gly Pro Thr Gly Ala Arg Leu Leu Ser Gln Asp Ser Val Ala
        90                  95                 100 gcc agc acc gag aag acc ctc agg ctc tat gat cgc agg agt atc ttt    1469
```

```
Ala Ser Thr Glu Lys Thr Leu Arg Leu Tyr Asp Arg Arg Ser Ile Phe
    105                 110                 115 gaa gcc gtt gct cag aat aac tgc cag gat ctg gag agc ctg ctc ctc      1517
Glu Ala Val Ala Gln Asn Asn Cys Gln Asp Leu Glu Ser Leu Leu Leu
120                 125                 130                 135 ttc ctg cag aag agc aag aag cac ctc aca gac aac gag ttc aaa gac      1565
Phe Leu Gln Lys Ser Lys Lys His Leu Thr Asp Asn Glu Phe Lys Asp
                140                 145                 150 cct gag aca ggg aag acc tgt ctg ctg aaa gcc atg ctc aac ctg cac      1613
Pro Glu Thr Gly Lys Thr Cys Leu Leu Lys Ala Met Leu Asn Leu His
                155                 160                 165 gac gga cag aac acc acc atc ccc ctg ctc ctg gag atc gcg cgg caa      1661
Asp Gly Gln Asn Thr Thr Ile Pro Leu Leu Leu Glu Ile Ala Arg Gln
            170                 175                 180 acg gac agc ctg aag gag ctt gtc aac gcc agc tac acg gac agc tac      1709
Thr Asp Ser Leu Lys Glu Leu Val Asn Ala Ser Tyr Thr Asp Ser Tyr
        185                 190                 195 tac aag ggc cag aca gca ctg cac atc gcc atc gag aga cgc aac atg      1757
Tyr Lys Gly Gln Thr Ala Leu His Ile Ala Ile Glu Arg Arg Asn Met
200                 205                 210                 215 gcc ctg gtg acc ctc ctg gtg gag aac gga gca gac gtc cag gct gcg      1805
Ala Leu Val Thr Leu Leu Val Glu Asn Gly Ala Asp Val Gln Ala Ala
                220                 225                 230 gcc cat ggg gac ttc ttt aag aaa acc aaa ggg cgg cct gga ttc tac      1853
Ala His Gly Asp Phe Phe Lys Lys Thr Lys Gly Arg Pro Gly Phe Tyr
            235                 240                 245 ttc ggt gaa ctg ccc ctg tcc ctg gcc gcg tgc acc aac cag ctg ggc      1901
Phe Gly Glu Leu Pro Leu Ser Leu Ala Ala Cys Thr Asn Gln Leu Gly
        250                 255                 260 atc gtg aag ttc ctg ctg cag aac tcc tgg cag acg gcc gac atc agc      1949
Ile Val Lys Phe Leu Leu Gln Asn Ser Trp Gln Thr Ala Asp Ile Ser
265                 270                 275 gcc agg gac tcg gtg ggc aac acg gtg ctg cac gcc ctg gtg gag gtg      1997
Ala Arg Asp Ser Val Gly Asn Thr Val Leu His Ala Leu Val Glu Val
280                 285                 290                 295 gcc gac aac acg gcc gac aac acg aag ttt gtg acg agc atg tac aat      2045
Ala Asp Asn Thr Ala Asp Asn Thr Lys Phe Val Thr Ser Met Tyr Asn
                300                 305                 310 gag att ctg atg ctg ggg gcc aaa ctg cac ccg acg ctg aag ctg gag      2093
Glu Ile Leu Met Leu Gly Ala Lys Leu His Pro Thr Leu Lys Leu Glu
            315                 320                 325 gag ctc acc aac aag aag gga atg acg ccg ctg gct ctg gca gct ggg      2141
Glu Leu Thr Asn Lys Lys Gly Met Thr Pro Leu Ala Leu Ala Ala Gly
        330                 335                 340 acc ggg aag atc ggg gtc ttg gcc tat att ctc cag cgg gag atc cag      2189
Thr Gly Lys Ile Gly Val Leu Ala Tyr Ile Leu Gln Arg Glu Ile Gln
345                 350                 355 gag ccc gag tgc agg cac ctg tcc agg aag ttc acc gag tgg gcc tac      2237
Glu Pro Glu Cys Arg His Leu Ser Arg Lys Phe Thr Glu Trp Ala Tyr
360                 365                 370                 375 ggg ccc gtg cac tcc tcg ctg tac gac ctg tcc tgc atc gac acc tgc      2285
Gly Pro Val His Ser Ser Leu Tyr Asp Leu Ser Cys Ile Asp Thr Cys
                380                 385                 390 gag aag aac tcg gtg ctg gag gtg atc gcc tac agc agc agc gag acc      2333
Glu Lys Asn Ser Val Leu Glu Val Ile Ala Tyr Ser Ser Ser Glu Thr
            395                 400                 405 cct aat cgc cac gac atg ctc ttg gtg gag ccg ctg aac cga ctc ctg      2381
Pro Asn Arg His Asp Met Leu Leu Val Glu Pro Leu Asn Arg Leu Leu
        410                 415                 420 cag gac aag tgg gac aga ttc gtc aag cgc atc ttc tac ttc aac ttc      2429
```

| | | | | | | | | | | | | | | | |
|---|---|---|---|---|---|---|---|---|---|---|---|---|---|---|---|
| Gln | Asp | Lys | Trp | Asp | Arg | Phe | Val | Lys | Arg | Ile | Phe | Tyr | Phe | Asn | Phe |
| | 425 | | | 430 | | | | 435 | | | | | | | |

```
ctg gtc tac tgc ctg tac atg atc atc ttc acc atg gct gcc tac tac      2477
Leu Val Tyr Cys Leu Tyr Met Ile Ile Phe Thr Met Ala Ala Tyr Tyr
440                 445                 450                 455 agg ccc gtg gat ggc ttg cct ccc ttt aag atg gaa aaa att gga gac      2525
Arg Pro Val Asp Gly Leu Pro Pro Phe Lys Met Glu Lys Ile Gly Asp
                460                 465                 470 tat ttc cga gtt act gga gag atc ctg tct gtg tta gga gga gtc tac      2573
Tyr Phe Arg Val Thr Gly Glu Ile Leu Ser Val Leu Gly Gly Val Tyr
            475                 480                 485 ttc ttt ttc cga ggg att cag tat ttc ctg cag agg cgg ccg tcg atg      2621
Phe Phe Phe Arg Gly Ile Gln Tyr Phe Leu Gln Arg Arg Pro Ser Met
        490                 495                 500 aag acc ctg ttt gtg gac agc tac agt gag atg ctt ttc ttt ctg cag      2669
Lys Thr Leu Phe Val Asp Ser Tyr Ser Glu Met Leu Phe Phe Leu Gln
    505                 510                 515 tca ctg ttc atg ctg gcc acc gtg gtg ctg tac ttc agc cac ctc aag      2717
Ser Leu Phe Met Leu Ala Thr Val Val Leu Tyr Phe Ser His Leu Lys
520                 525                 530                 535 gag tat gtg gct tcc atg gta ttc tcc ctg gcc ttg ggc tgg acc aac      2765
Glu Tyr Val Ala Ser Met Val Phe Ser Leu Ala Leu Gly Trp Thr Asn
                540                 545                 550 atg ctc tac tac acc cgc ggt ttc cag cag atg ggc atc tat gcc gtc      2813
Met Leu Tyr Tyr Thr Arg Gly Phe Gln Gln Met Gly Ile Tyr Ala Val
            555                 560                 565 atg ata gag aag atg atc ctg aga gac ctg tgc cgt ttc atg ttt gtc      2861
Met Ile Glu Lys Met Ile Leu Arg Asp Leu Cys Arg Phe Met Phe Val
        570                 575                 580 tac atc gtc ttc ttg ttc ggg ttt tcc aca gcg gtg gtg acg ctg att      2909
Tyr Ile Val Phe Leu Phe Gly Phe Ser Thr Ala Val Val Thr Leu Ile
    585                 590                 595 gaa gac ggg aag aat gac tcc ctg ccg tct gag tcc acg tcg cac agg      2957
Glu Asp Gly Lys Asn Asp Ser Leu Pro Ser Glu Ser Thr Ser His Arg
600                 605                 610                 615 tgg cgg ggg cct gcc tgc agg ccc ccc gat agc tcc tac aac agc ctg      3005
Trp Arg Gly Pro Ala Cys Arg Pro Pro Asp Ser Ser Tyr Asn Ser Leu
                620                 625                 630 tac tcc acc tgc ctg gag ctg ttc aag ttc acc atc ggc atg ggc gac      3053
Tyr Ser Thr Cys Leu Glu Leu Phe Lys Phe Thr Ile Gly Met Gly Asp
            635                 640                 645 ctg gag ttc act gag aac tat gac ttc aag gct gtc ttc atc atc ctg      3101
Leu Glu Phe Thr Glu Asn Tyr Asp Phe Lys Ala Val Phe Ile Ile Leu
        650                 655                 660 ctg ctg gcc tat gta att ctc acc tac atc ctc ctg ctc aac atg ctc      3149
Leu Leu Ala Tyr Val Ile Leu Thr Tyr Ile Leu Leu Leu Asn Met Leu
    665                 670                 675 atc gcc ctc atg ggt gag act gtc aac aag atc gca cag gag agc aag      3197
Ile Ala Leu Met Gly Glu Thr Val Asn Lys Ile Ala Gln Glu Ser Lys
680                 685                 690                 695 aac atc tgg aag ctg cag aga gcc atc acc atc ctg gac acg gag aag      3245
Asn Ile Trp Lys Leu Gln Arg Ala Ile Thr Ile Leu Asp Thr Glu Lys
                700                 705                 710 agc ttc ctt aag tgc atg agg aag gcc ttc cgc tca ggc aag ctg ctg      3293
Ser Phe Leu Lys Cys Met Arg Lys Ala Phe Arg Ser Gly Lys Leu Leu
            715                 720                 725 cag gtg ggg tac aca cct gat ggc aag gac gac tac cgg tgg tgc ttc      3341
Gln Val Gly Tyr Thr Pro Asp Gly Lys Asp Asp Tyr Arg Trp Cys Phe
        730                 735                 740 agg gtg gac gag gtg aac tgg acc acc tgg aac acc aac gtg ggc atc      3389
```

```
Arg Val Asp Glu Val Asn Trp Thr Thr Trp Asn Thr Asn Val Gly Ile
         745                 750                 755 atc aac gaa gac ccg ggc aac tgt gag ggc gtc aag cgc acc ctg agc      3437
Ile Asn Glu Asp Pro Gly Asn Cys Glu Gly Val Lys Arg Thr Leu Ser
760                 765                 770                 775 ttc tcc ctg cgg tca agc aga gtt tca ggc aga cac tgg aag aac ttt      3485
Phe Ser Leu Arg Ser Ser Arg Val Ser Gly Arg His Trp Lys Asn Phe
                780                 785                 790 gcc ctg gtc ccc ctt tta aga gag gca agt gct cga gat agg cag tct      3533
Ala Leu Val Pro Leu Leu Arg Glu Ala Ser Ala Arg Asp Arg Gln Ser
            795                 800                 805 gct cag ccc gag gaa gtt tat ctg cga cag ttt tca ggg tct ctg aag      3581
Ala Gln Pro Glu Glu Val Tyr Leu Arg Gln Phe Ser Gly Ser Leu Lys
        810                 815                 820 cca gag gac gct gag gtc ttc aag agt cct gcc gct tcc ggg gag aag      3629
Pro Glu Asp Ala Glu Val Phe Lys Ser Pro Ala Ala Ser Gly Glu Lys
    825                 830                 835 tgaggacgtc acgcagacag cactgtcaac actgggcctt aggagacccc gttgccacgg    3689
ggggctgctg agggaacacc agtgctctgt cagcagcctg gcctggtctg tgcctgccca    3749
gcatgttccc aaatctgtgc tggacaagct gtgggaagcg ttcttggaag catggggagt    3809
gatgtacatc caaccgtcac tgtccccaag tgaatctcct aacagacttt caggtttta     3869 ctcactttac taaaaaaaaa aaaaaagggg cggccgctta                          3909

<210> SEQ ID NO 2
<211> LENGTH: 839
<212> TYPE: PRT
<213> ORGANISM: Homo sapiens

<400> SEQUENCE: 2

Met Lys Lys Trp Ser Ser Thr Asp Leu Gly Thr Ala Ala Asp Pro Leu
 1               5                  10                  15

Gln Lys Asp Thr Cys Pro Asp Pro Leu Asp Gly Asp Pro Asn Ser Arg
            20                  25                  30

Pro Pro Pro Ala Lys Pro Gln Leu Pro Thr Ala Lys Ser Arg Thr Arg
        35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205
```

-continued

```
Ala Ile Glu Arg Arg Asn Met Ala Leu Val Thr Leu Leu Val Glu Asn
            210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                    245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
        290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                    325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
            355                 360                 365

Lys Phe Thr Glu Trp Ala Tyr Gly Pro Val His Ser Ser Leu Tyr Asp
370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                    405                 410                 415

Glu Pro Leu Asn Arg Leu Leu Gln Asp Lys Trp Asp Arg Phe Val Lys
                420                 425                 430

Arg Ile Phe Tyr Phe Asn Phe Leu Val Tyr Cys Leu Tyr Met Ile Ile
            435                 440                 445

Phe Thr Met Ala Ala Tyr Tyr Arg Pro Val Asp Gly Leu Pro Pro Phe
450                 455                 460

Lys Met Glu Lys Ile Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                    485                 490                 495

Leu Gln Arg Arg Pro Ser Met Lys Thr Leu Phe Val Asp Ser Tyr Ser
                500                 505                 510

Glu Met Leu Phe Phe Leu Gln Ser Leu Phe Met Leu Ala Thr Val Val
            515                 520                 525

Leu Tyr Phe Ser His Leu Lys Glu Tyr Val Ala Ser Met Val Phe Ser
        530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                    565                 570                 575

Leu Cys Arg Phe Met Phe Val Tyr Ile Val Phe Leu Phe Gly Phe Ser
            580                 585                 590

Thr Ala Val Val Thr Leu Ile Glu Asp Gly Lys Asn Asp Ser Leu Pro
        595                 600                 605

Ser Glu Ser Thr Ser His Arg Trp Arg Gly Pro Ala Cys Arg Pro Pro
610                 615                 620

Asp Ser Ser Tyr Asn Ser Leu Tyr Ser Thr Cys Leu Glu Leu Phe Lys
625                 630                 635                 640
```

-continued

```
Phe Thr Ile Gly Met Gly Asp Leu Glu Phe Thr Glu Asn Tyr Asp Phe
                645                 650                 655
Lys Ala Val Phe Ile Ile Leu Leu Ala Tyr Val Ile Leu Thr Tyr
        660                 665                 670
Ile Leu Leu Leu Asn Met Leu Ile Ala Leu Met Gly Glu Thr Val Asn
            675                 680                 685
Lys Ile Ala Gln Glu Ser Lys Asn Ile Trp Lys Leu Gln Arg Ala Ile
690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Glu Val Tyr Leu Arg
                805                 810                 815
Gln Phe Ser Gly Ser Leu Lys Pro Glu Asp Ala Glu Val Phe Lys Ser
            820                 825                 830
Pro Ala Ala Ser Gly Glu Lys
        835
```

<210> SEQ ID NO 3
<211> LENGTH: 2517
<212> TYPE: DNA
<213> ORGANISM: Homo sapiens
<220> FEATURE:
<221> NAME/KEY: CDS
<222> LOCATION: (1)..(2517)

<400> SEQUENCE: 3

```
atg aag aaa tgg agc agc aca gac ttg ggg aca gct gcg gac cca ctc      48
Met Lys Lys Trp Ser Ser Thr Asp Leu Gly Thr Ala Ala Asp Pro Leu
  1               5                  10                  15 caa aag gac acc tgc cca gac ccc ctg gat gga gac cct aac tcc agg      96
Gln Lys Asp Thr Cys Pro Asp Pro Leu Asp Gly Asp Pro Asn Ser Arg
             20                  25                  30 cca cct cca gcc aag ccc cag ctc ccc acg gcc aag agc cgc acc cgg     144
Pro Pro Pro Ala Lys Pro Gln Leu Pro Thr Ala Lys Ser Arg Thr Arg
         35                  40                  45 ctc ttt ggg aag ggt gac tcg gag gag gct ttc ccg gtg gat tgc ccc     192
Leu Phe Gly Lys Gly Asp Ser Glu Glu Ala Phe Pro Val Asp Cys Pro
     50                  55                  60 cac gag gaa ggt gag ttg gac tcc tgc ccg acc atc aca gtc agc cct     240
His Glu Glu Gly Glu Leu Asp Ser Cys Pro Thr Ile Thr Val Ser Pro
 65                  70                  75                  80 gtt atc acc atc cag agg cca gga gac ggc ccc acc ggt gcc agg ctg     288
Val Ile Thr Ile Gln Arg Pro Gly Asp Gly Pro Thr Gly Ala Arg Leu
                 85                  90                  95 ctg tcc cag gac tct gtc gcc gcc agc acc gag aag acc ctc agg ctc     336
Leu Ser Gln Asp Ser Val Ala Ala Ser Thr Glu Lys Thr Leu Arg Leu
            100                 105                 110 tat gat cgc agg agt atc ttt gaa gcc gtt gct cag aat aac tgc cag     384
Tyr Asp Arg Arg Ser Ile Phe Glu Ala Val Ala Gln Asn Asn Cys Gln
```

```
Tyr Asp Arg Arg Ser Ile Phe Glu Ala Val Ala Gln Asn Asn Cys Gln
        115                 120                 125 gat ctg gag agc ctg ctg ctc ttc ctg cag aag agc aag aag cac ctc       432
Asp Leu Glu Ser Leu Leu Leu Phe Leu Gln Lys Ser Lys Lys His Leu
130                 135                 140 aca gac aac gag ttc aaa gac cct gag aca ggg aag acc tgt ctg ctg       480
Thr Asp Asn Glu Phe Lys Asp Pro Glu Thr Gly Lys Thr Cys Leu Leu
145                 150                 155                 160 aaa gcc atg ctc aac ctg cac gac gga cag aac acc acc atc ccc ctg       528
Lys Ala Met Leu Asn Leu His Asp Gly Gln Asn Thr Thr Ile Pro Leu
                165                 170                 175 ctc ctg gag atc gcg cgg caa acg gac agc ctg aag gag ctt gtc aac       576
Leu Leu Glu Ile Ala Arg Gln Thr Asp Ser Leu Lys Glu Leu Val Asn
                    180                 185                 190 gcc agc tac acg gac agc tac tac aag ggc cag aca gca ctg cac atc       624
Ala Ser Tyr Thr Asp Ser Tyr Tyr Lys Gly Gln Thr Ala Leu His Ile
                195                 200                 205 gcc atc gag aga cgc aac atg gcc ctg gtg acc ctc ctg gtg gag aac       672
Ala Ile Glu Arg Arg Asn Met Ala Leu Val Thr Leu Leu Val Glu Asn
210                 215                 220 gga gca gac gtc cag gct gcg gcc cat ggg gac ttc ttt aag aaa acc       720
Gly Ala Asp Val Gln Ala Ala Ala His Gly Asp Phe Phe Lys Lys Thr
225                 230                 235                 240 aaa ggg cgg cct gga ttc tac ttc ggt gaa ctg ccc ctg tcc ctg gcc       768
Lys Gly Arg Pro Gly Phe Tyr Phe Gly Glu Leu Pro Leu Ser Leu Ala
                245                 250                 255 gcg tgc acc aac cag ctg ggc atc gtg aag ttc ctg ctg cag aac tcc       816
Ala Cys Thr Asn Gln Leu Gly Ile Val Lys Phe Leu Leu Gln Asn Ser
                260                 265                 270 tgg cag acg gcc gac atc agc gcc agg gac tcg gtg ggc aac acg gtg       864
Trp Gln Thr Ala Asp Ile Ser Ala Arg Asp Ser Val Gly Asn Thr Val
                275                 280                 285 ctg cac gcc ctg gtg gag gtg gcc gac aac acg gcc gac aac acg aag       912
Leu His Ala Leu Val Glu Val Ala Asp Asn Thr Ala Asp Asn Thr Lys
                290                 295                 300 ttt gtg acg agc atg tac aat gag att ctg atg ctg ggg gcc aaa ctg       960
Phe Val Thr Ser Met Tyr Asn Glu Ile Leu Met Leu Gly Ala Lys Leu
305                 310                 315                 320 cac ccg acg ctg aag ctg gag gag ctc acc aac aag aag gga atg acg      1008
His Pro Thr Leu Lys Leu Glu Glu Leu Thr Asn Lys Lys Gly Met Thr
                325                 330                 335 ccg ctg gct ctg gca gct ggg acc ggg aag atc ggg gtc ttg gcc tat      1056
Pro Leu Ala Leu Ala Ala Gly Thr Gly Lys Ile Gly Val Leu Ala Tyr
                340                 345                 350 att ctc cag cgg gag atc cag gag ccc gag tgc agg cac ctg tcc agg      1104
Ile Leu Gln Arg Glu Ile Gln Glu Pro Glu Cys Arg His Leu Ser Arg
                355                 360                 365 aag ttc acc gag tgg gcc tac ggg ccc gtg cac tcg tcg ctg tac gac      1152
Lys Phe Thr Glu Trp Ala Tyr Gly Pro Val His Ser Ser Leu Tyr Asp
370                 375                 380 ctg tcc tgc atc gac acc tgc gag aag aac tcg gtg ctg gag gtg atc      1200
Leu Ser Cys Ile Asp Thr Cys Glu Lys Asn Ser Val Leu Glu Val Ile
385                 390                 395                 400 gcc tac agc agc agc gag acc cct aat cgc cac gac atg ctc ttg gtg      1248
Ala Tyr Ser Ser Ser Glu Thr Pro Asn Arg His Asp Met Leu Leu Val
                405                 410                 415 gag ccg ctg aac cga ctc ctg cag gac aag tgg gac aga ttc gtc aag      1296
Glu Pro Leu Asn Arg Leu Leu Gln Asp Lys Trp Asp Arg Phe Val Lys
                420                 425                 430 cgc atc ttc tac ttc aac ttc ctg gtc tac tgc ctg tac atg atc atc      1344
```

```
                Arg Ile Phe Tyr Phe Asn Phe Leu Val Tyr Cys Leu Tyr Met Ile Ile
                    435                 440                 445 ttc acc atg gct gcc tac tac agg ccc gtg gat ggc ttg cct ccc ttt              1392
Phe Thr Met Ala Ala Tyr Tyr Arg Pro Val Asp Gly Leu Pro Pro Phe
450                 455                 460 aag atg gaa aaa att gga gac tat ttc cga gtt act gga gag atc ctg              1440
Lys Met Glu Lys Ile Gly Asp Tyr Phe Arg Val Thr Gly Glu Ile Leu
465                 470                 475                 480 tct gtg tta gga gga gtc tac ttc ttt ttc cga ggg att cag tat ttc              1488
Ser Val Leu Gly Gly Val Tyr Phe Phe Phe Arg Gly Ile Gln Tyr Phe
                    485                 490                 495 ctg cag agg cgg ccg tcg atg aag acc ctg ttt gtg gac agc tac agt              1536
Leu Gln Arg Arg Pro Ser Met Lys Thr Leu Phe Val Asp Ser Tyr Ser
                500                 505                 510 gag atg ctt ttc ttt ctg cag tca ctg ttc atg ctg gcc acc gtg gtg              1584
Glu Met Leu Phe Phe Leu Gln Ser Leu Phe Met Leu Ala Thr Val Val
            515                 520                 525 ctg tac ttc agc cac ctc aag gag tat gtg gct tcc atg gta ttc tcc              1632
Leu Tyr Phe Ser His Leu Lys Glu Tyr Val Ala Ser Met Val Phe Ser
        530                 535                 540 ctg gcc ttg ggc tgg acc aac atg ctc tac tac acc cgc ggt ttc cag              1680
Leu Ala Leu Gly Trp Thr Asn Met Leu Tyr Tyr Thr Arg Gly Phe Gln
545                 550                 555                 560 cag atg ggc atc tat gcc gtc atg ata gag aag atg atc ctg aga gac              1728
Gln Met Gly Ile Tyr Ala Val Met Ile Glu Lys Met Ile Leu Arg Asp
                    565                 570                 575 ctg tgc cgt ttc atg ttt gtc tac atc gtc ttc ttg ttc ggg ttt tcc              1776
Leu Cys Arg Phe Met Phe Val Tyr Ile Val Phe Leu Phe Gly Phe Ser
                580                 585                 590 aca gcg gtg gtg acg ctg att gaa gac ggg aag aat gac tcc ctg ccg              1824
Thr Ala Val Val Thr Leu Ile Glu Asp Gly Lys Asn Asp Ser Leu Pro
            595                 600                 605 tct gag tcc acg tcg cac agg tgg cgg ggg cct gcc tgc agg ccc ccc              1872
Ser Glu Ser Thr Ser His Arg Trp Arg Gly Pro Ala Cys Arg Pro Pro
        610                 615                 620 gat agc tcc tac aac agc ctg tac tcc acc tgc ctg gag ctg ttc aag              1920
Asp Ser Ser Tyr Asn Ser Leu Tyr Ser Thr Cys Leu Glu Leu Phe Lys
625                 630                 635                 640 ttc acc atc ggc atg ggc gac ctg gag ttc act gag aac tat gac ttc              1968
Phe Thr Ile Gly Met Gly Asp Leu Glu Phe Thr Glu Asn Tyr Asp Phe
                    645                 650                 655 aag gct gtc ttc atc atc ctg ctg ctg gcc tat gta att ctc acc tac              2016
Lys Ala Val Phe Ile Ile Leu Leu Leu Ala Tyr Val Ile Leu Thr Tyr
                660                 665                 670 atc ctc ctg ctc aac atg ctc atc gcc ctc atg ggt gag act gtc aac              2064
Ile Leu Leu Leu Asn Met Leu Ile Ala Leu Met Gly Glu Thr Val Asn
            675                 680                 685 aag atc gca cag gag agc aag aac atc tgg aag ctg cag aga gcc atc              2112
Lys Ile Ala Gln Glu Ser Lys Asn Ile Trp Lys Leu Gln Arg Ala Ile
        690                 695                 700 acc atc ctg gac acg gag aag agc ttc ctt aag tgc atg agg aag gcc              2160
Thr Ile Leu Asp Thr Glu Lys Ser Phe Leu Lys Cys Met Arg Lys Ala
705                 710                 715                 720 ttc cgc tca ggc aag ctg ctg cag gtg ggg tac aca cct gat ggc aag              2208
Phe Arg Ser Gly Lys Leu Leu Gln Val Gly Tyr Thr Pro Asp Gly Lys
                    725                 730                 735 gac gac tac cgg tgg tgc ttc agg gtg gac gag gtg aac tgg acc acc              2256
Asp Asp Tyr Arg Trp Cys Phe Arg Val Asp Glu Val Asn Trp Thr Thr
                740                 745                 750 tgg aac acc aac gtg ggc atc atc aac gaa gac ccg ggc aac tgt gag              2304
```

```
                Trp Asn Thr Asn Val Gly Ile Ile Asn Glu Asp Pro Gly Asn Cys Glu
                                755                 760                 765 ggc gtc aag cgc acc ctg agc ttc tcc ctg cgg tca agc aga gtt tca          2352
Gly Val Lys Arg Thr Leu Ser Phe Ser Leu Arg Ser Ser Arg Val Ser
            770                 775                 780 ggc aga cac tgg aag aac ttt gcc ctg gtc ccc ctt tta aga gag gca          2400
Gly Arg His Trp Lys Asn Phe Ala Leu Val Pro Leu Leu Arg Glu Ala
785                 790                 795                 800 agt gct cga gat agg cag tct gct cag ccc gag gaa gtt tat ctg cga          2448
Ser Ala Arg Asp Arg Gln Ser Ala Gln Pro Glu Glu Val Tyr Leu Arg
                805                 810                 815 cag ttt tca ggg tct ctg aag cca gag gac gct gag gtc ttc aag agt          2496
Gln Phe Ser Gly Ser Leu Lys Pro Glu Asp Ala Glu Val Phe Lys Ser
                820                 825                 830 cct gcc gct tcc ggg gag aag                                              2517
Pro Ala Ala Ser Gly Glu Lys
                835

<210> SEQ ID NO 4
<211> LENGTH: 2809
<212> TYPE: DNA
<213> ORGANISM: Homo sapiens
<220> FEATURE:
<221> NAME/KEY: CDS
<222> LOCATION: (361)..(2652)

<400> SEQUENCE: 4
ggctagcctg tcctgacagg ggagagttaa gctcccgttc tccaccgtgc cggctggcca         60
ggtgggctga gggtgaccga gagaccagaa cctgcttgct ggagcttagt gctcagagct        120
ggggagggag gttccgccgc tcctctgctg tcagcgccgg cagcccctcc cggcttcact        180
tcctcccgca gcccctgcta ctgagaagct ccgggatccc agcagccgcc acgccctggc        240
ctcagcctgc ggggctccag tcaggccaac accgacgcgc agctggggag aagacaggac        300
ccttgacatc tccatctgca cagaggtcct ggctggaccg agcagcctcc tcctcctagg        360 atg acc tca ccc tcc agc tct cca gtt ttc agg ttg gag aca tta gat          408
Met Thr Ser Pro Ser Ser Ser Pro Val Phe Arg Leu Glu Thr Leu Asp
 1               5                  10                  15 gga ggc caa gaa gat ggc tct gag gcg gac aga gga aag ctg gat ttt          456
Gly Gly Gln Glu Asp Gly Ser Glu Ala Asp Arg Gly Lys Leu Asp Phe
                20                  25                  30 ggg agc ggg ctg cct ccc atg gag tca cag ttc cag ggc gag gac cgg          504
Gly Ser Gly Leu Pro Pro Met Glu Ser Gln Phe Gln Gly Glu Asp Arg
            35                  40                  45 aaa ttc gcc cct cag ata aga gtc aac ctc aac tac cga aag gga aca          552
Lys Phe Ala Pro Gln Ile Arg Val Asn Leu Asn Tyr Arg Lys Gly Thr
        50                  55                  60 ggt gcc agt cag ccg gat cca aac cga ttt gac cga gat cgg ctc ttc          600
Gly Ala Ser Gln Pro Asp Pro Asn Arg Phe Asp Arg Asp Arg Leu Phe
65                  70                  75                  80 aat gcg gtc tcc cgg ggt gtc ccc gag gat ctg gct gga ctt cca gag          648
Asn Ala Val Ser Arg Gly Val Pro Glu Asp Leu Ala Gly Leu Pro Glu
                85                  90                  95 tac ctg agc aag acc agc aag tac ctc acc gac tcg gaa tac aca gag          696
Tyr Leu Ser Lys Thr Ser Lys Tyr Leu Thr Asp Ser Glu Tyr Thr Glu
                100                 105                 110 ggc tcc aca ggt aag acg tgc ctg atg aag gct gtg ctg aac ctt aag          744
Gly Ser Thr Gly Lys Thr Cys Leu Met Lys Ala Val Leu Asn Leu Lys
            115                 120                 125 gac gga gtc aat gcc tgc att ctg cca ctg ctg cag atc gac agg gac          792
Asp Gly Val Asn Ala Cys Ile Leu Pro Leu Leu Gln Ile Asp Arg Asp
```

-continued

```
             130                 135                 140
tct ggc aat cct cag ccc ctg gta aat gcc cag tgc aca gat gac tat      840
Ser Gly Asn Pro Gln Pro Leu Val Asn Ala Gln Cys Thr Asp Asp Tyr
145                 150                 155                 160 tac cga ggc cac agc gct ctg cac atc gcc att gag aag agg agt ctg      888
Tyr Arg Gly His Ser Ala Leu His Ile Ala Ile Glu Lys Arg Ser Leu
                165                 170                 175 cag tgt gtg aag ctc ctg gtg gag aat ggg gcc aat gtg cat gcc cgg      936
Gln Cys Val Lys Leu Leu Val Glu Asn Gly Ala Asn Val His Ala Arg
            180                 185                 190 gcc tgc ggc cgc ttc ttc cag aag ggc caa ggg act tgc ttt tat ttc      984
Ala Cys Gly Arg Phe Phe Gln Lys Gly Gln Gly Thr Cys Phe Tyr Phe
                195                 200                 205 ggt gag cta ccc ctc tct ttg gcc gct tgc acc aag cag tgg gat gtg     1032
Gly Glu Leu Pro Leu Ser Leu Ala Ala Cys Thr Lys Gln Trp Asp Val
210                 215                 220 gta agc tac ctc ctg gag aac cca cac cag ccc gcc agc ctg cag gcc     1080
Val Ser Tyr Leu Leu Glu Asn Pro His Gln Pro Ala Ser Leu Gln Ala
225                 230                 235                 240 act gac tcc cag ggc aac aca gtc ctg cat gcc cta gtg atg atc tcg     1128
Thr Asp Ser Gln Gly Asn Thr Val Leu His Ala Leu Val Met Ile Ser
                245                 250                 255 gac aac tca gct gag aac att gca ctg gtg acc agc atg tat gat ggg     1176
Asp Asn Ser Ala Glu Asn Ile Ala Leu Val Thr Ser Met Tyr Asp Gly
                260                 265                 270 ctc ctc caa gct ggg gcc cgc ctc tgc cct acc gtg cag ctt gag gac     1224
Leu Leu Gln Ala Gly Ala Arg Leu Cys Pro Thr Val Gln Leu Glu Asp
            275                 280                 285 atc cgc aac ctg cag gat ctc acg cct ctg aag ctg gcc gcc aag gag     1272
Ile Arg Asn Leu Gln Asp Leu Thr Pro Leu Lys Leu Ala Ala Lys Glu
290                 295                 300 ggc aag atc gag att ttc agg cac atc ctg cag cgg gag ttt tca gga     1320
Gly Lys Ile Glu Ile Phe Arg His Ile Leu Gln Arg Glu Phe Ser Gly
305                 310                 315                 320 ctg agc cac ctt tcc cga aag ttc acc gag tgg tgc tat ggg cct gtc     1368
Leu Ser His Leu Ser Arg Lys Phe Thr Glu Trp Cys Tyr Gly Pro Val
                325                 330                 335 cgg gtg tcg ctg tat gac ctg gct tct gtg gac agc tgt gag gag aac     1416
Arg Val Ser Leu Tyr Asp Leu Ala Ser Val Asp Ser Cys Glu Glu Asn
            340                 345                 350 tca gtg ctg gag atc att gcc ttt cat tgc aag agc ccg cac cga cac     1464
Ser Val Leu Glu Ile Ile Ala Phe His Cys Lys Ser Pro His Arg His
                355                 360                 365 cga atg gtc gtt ttg gag ccc ctg aac aaa ctg ctg cag gcg aaa tgg     1512
Arg Met Val Val Leu Glu Pro Leu Asn Lys Leu Leu Gln Ala Lys Trp
370                 375                 380 gat ctg ctc atc ccc aag ttc ttc tta aac ttc ctg tgt aat ctg atc     1560
Asp Leu Leu Ile Pro Lys Phe Phe Leu Asn Phe Leu Cys Asn Leu Ile
385                 390                 395                 400 tac atg ttc atc ttc acc gct gtt gcc tac cat cag cct acc ctg aag     1608
Tyr Met Phe Ile Phe Thr Ala Val Ala Tyr His Gln Pro Thr Leu Lys
                405                 410                 415 aag cag gcc gcc cct cac ctg aaa gcg gag gtt gga aac tcc atg ctg     1656
Lys Gln Ala Ala Pro His Leu Lys Ala Glu Val Gly Asn Ser Met Leu
            420                 425                 430 ctg acg ggc cac atc ctt atc ctg cta ggg ggg atc tac ctc ctc gtg     1704
Leu Thr Gly His Ile Leu Ile Leu Leu Gly Gly Ile Tyr Leu Leu Val
                435                 440                 445 ggc cag ctg tgg tac ttc tgg cgg cgc cac gtg ttc atc tgg atc tcg     1752
Gly Gln Leu Trp Tyr Phe Trp Arg Arg His Val Phe Ile Trp Ile Ser
```

```
                450                    455                    460
ttc ata gac agc tac ttt gaa atc ctc ttc ctg ttc cag gcc ctg ctc    1800
Phe Ile Asp Ser Tyr Phe Glu Ile Leu Phe Leu Phe Gln Ala Leu Leu
465                    470                    475                    480 aca gtg gtg tcc cag gtg ctg tgt ttc ctg gcc atc gag tgg tac ctg    1848
Thr Val Val Ser Gln Val Leu Cys Phe Leu Ala Ile Glu Trp Tyr Leu
                485                    490                    495 ccc ctg ctt gtg tct gcg ctg gtg ctg ggc tgg ctg aac ctg ctt tac    1896
Pro Leu Leu Val Ser Ala Leu Val Leu Gly Trp Leu Asn Leu Leu Tyr
            500                    505                    510 tat aca cgt ggc ttc cag cac aca ggc atc tac agt gtc atg atc cag    1944
Tyr Thr Arg Gly Phe Gln His Thr Gly Ile Tyr Ser Val Met Ile Gln
        515                    520                    525 aag gtc atc ctg cgg gac ctg ctg cgc ttc ctt ctg atc tac tta gtc    1992
Lys Val Ile Leu Arg Asp Leu Leu Arg Phe Leu Leu Ile Tyr Leu Val
530                    535                    540 ttc ctt ttc ggc ttc gct gta gcc ctg gtg agc ctg agc cag gag gct    2040
Phe Leu Phe Gly Phe Ala Val Ala Leu Val Ser Leu Ser Gln Glu Ala
545                    550                    555                    560 tgg cgc ccc gaa gct cct aca ggc ccc aat gcc aca gag tca gtg cag    2088
Trp Arg Pro Glu Ala Pro Thr Gly Pro Asn Ala Thr Glu Ser Val Gln
                565                    570                    575 ccc atg gag gga cag gag gac gag ggc aac ggg gcc cag tac agg ggt    2136
Pro Met Glu Gly Gln Glu Asp Glu Gly Asn Gly Ala Gln Tyr Arg Gly
            580                    585                    590 atc ctg gaa gcc tcc ttg gag ctc ttc aaa ttc acc atc ggc atg ggc    2184
Ile Leu Glu Ala Ser Leu Glu Leu Phe Lys Phe Thr Ile Gly Met Gly
        595                    600                    605 gag ctg gcc ttc cag gag cag ctg cac ttc cgc ggc atg gtg ctg ctg    2232
Glu Leu Ala Phe Gln Glu Gln Leu His Phe Arg Gly Met Val Leu Leu
610                    615                    620 ctg ctg ctg gcc tac gtg ctg ctc acc tac atc ctg ctg ctc aac atg    2280
Leu Leu Leu Ala Tyr Val Leu Leu Thr Tyr Ile Leu Leu Leu Asn Met
625                    630                    635                    640 ctc atc gcc ctc atg agc gag acc gtc aac agt gtc gcc act gac agc    2328
Leu Ile Ala Leu Met Ser Glu Thr Val Asn Ser Val Ala Thr Asp Ser
                645                    650                    655 tgg agc atc tgg aag ctg cag aaa gcc atc tct gtc ctg gag atg gag    2376
Trp Ser Ile Trp Lys Leu Gln Lys Ala Ile Ser Val Leu Glu Met Glu
            660                    665                    670 aat ggc tat tgg tgg tgc agg aag aag cag cgg gca ggt gtg atg ctg    2424
Asn Gly Tyr Trp Trp Cys Arg Lys Lys Gln Arg Ala Gly Val Met Leu
        675                    680                    685 acc gtt ggc act aag cca gat ggc agc ccg gat gag cgc tgg tgc ttc    2472
Thr Val Gly Thr Lys Pro Asp Gly Ser Pro Asp Glu Arg Trp Cys Phe
690                    695                    700 agg gtg gag gag gtg aac tgg gct tca tgg gag cag acg ctg cct acg    2520
Arg Val Glu Glu Val Asn Trp Ala Ser Trp Glu Gln Thr Leu Pro Thr
705                    710                    715                    720 ctg tgt gag gac ccg tca ggg gca ggt gtc cct cga act ctc gag aac    2568
Leu Cys Glu Asp Pro Ser Gly Ala Gly Val Pro Arg Thr Leu Glu Asn
                725                    730                    735 cct gtc ctg gct tcc cct ccc aag gag gat gag gat ggt gcc tct gag    2616
Pro Val Leu Ala Ser Pro Pro Lys Glu Asp Glu Asp Gly Ala Ser Glu
            740                    745                    750 gaa aac tat gtg ccc gtc cag ctc ctc cag tcc aac tgatggccca         2662
Glu Asn Tyr Val Pro Val Gln Leu Leu Gln Ser Asn
        755                    760 gatgcagcag gaggccagag gacagagcag aggatctttc aaccacatc tgctggctct   2722
```

```
gggtcccag tgaattctgg tggcaaatat atattttcac taactcaaaa aaaaaaaaa    2782 aaaaaaaaaa aaaaaaaaaa aaaaaaa                                      2809
```

<210> SEQ ID NO 5
<211> LENGTH: 764
<212> TYPE: PRT
<213> ORGANISM: Homo sapiens

<400> SEQUENCE: 5

```
Met Thr Ser Pro Ser Ser Pro Val Phe Arg Leu Glu Thr Leu Asp
 1               5                  10                  15

Gly Gly Gln Glu Asp Gly Ser Glu Ala Asp Arg Gly Lys Leu Asp Phe
            20                  25                  30

Gly Ser Gly Leu Pro Pro Met Glu Ser Gln Phe Gln Gly Glu Asp Arg
        35                  40                  45

Lys Phe Ala Pro Gln Ile Arg Val Asn Leu Asn Tyr Arg Lys Gly Thr
    50                  55                  60

Gly Ala Ser Gln Pro Asp Pro Asn Arg Phe Asp Arg Asp Arg Leu Phe
65                  70                  75                  80

Asn Ala Val Ser Arg Gly Val Pro Glu Asp Leu Ala Gly Leu Pro Glu
                85                  90                  95

Tyr Leu Ser Lys Thr Ser Lys Tyr Leu Thr Asp Ser Glu Tyr Thr Glu
            100                 105                 110

Gly Ser Thr Gly Lys Thr Cys Leu Met Lys Ala Val Leu Asn Leu Lys
        115                 120                 125

Asp Gly Val Asn Ala Cys Ile Leu Pro Leu Leu Gln Ile Asp Arg Asp
    130                 135                 140

Ser Gly Asn Pro Gln Pro Leu Val Asn Ala Gln Cys Thr Asp Asp Tyr
145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Arg
            180                 185                 190

Ala Cys Gly Arg Phe Phe Gln Lys Gly Gln Gly Thr Cys Phe Tyr Phe
        195                 200                 205

Gly Glu Leu Pro Leu Ser Leu Ala Ala Cys Thr Lys Gln Trp Asp Val
    210                 215                 220

Val Ser Tyr Leu Leu Glu Asn Pro His Gln Pro Ala Ser Leu Gln Ala
225                 230                 235                 240

Thr Asp Ser Gln Gly Asn Thr Val Leu His Ala Leu Val Met Ile Ser
                245                 250                 255

Asp Asn Ser Ala Glu Asn Ile Ala Leu Val Thr Ser Met Tyr Asp Gly
            260                 265                 270

Leu Leu Gln Ala Gly Ala Arg Leu Cys Pro Thr Val Gln Leu Glu Asp
        275                 280                 285

Ile Arg Asn Leu Gln Asp Leu Thr Pro Leu Lys Leu Ala Ala Lys Glu
    290                 295                 300

Gly Lys Ile Glu Ile Phe Arg His Ile Leu Gln Arg Glu Phe Ser Gly
305                 310                 315                 320

Leu Ser His Leu Ser Arg Lys Phe Thr Glu Trp Cys Tyr Gly Pro Val
                325                 330                 335

Arg Val Ser Leu Tyr Asp Leu Ala Ser Val Asp Ser Cys Glu Glu Asn
            340                 345                 350

Ser Val Leu Glu Ile Ile Ala Phe His Cys Lys Ser Pro His Arg His
        355                 360                 365
```

Arg Met Val Val Leu Glu Pro Leu Asn Lys Leu Leu Gln Ala Lys Trp
    370                 375                 380

Asp Leu Leu Ile Pro Lys Phe Phe Leu Asn Phe Leu Cys Asn Leu Ile
385                 390                 395                 400

Tyr Met Phe Ile Phe Thr Ala Val Ala Tyr His Gln Pro Thr Leu Lys
                405                 410                 415

Lys Gln Ala Ala Pro His Leu Lys Ala Glu Val Gly Asn Ser Met Leu
            420                 425                 430

Leu Thr Gly His Ile Leu Ile Leu Gly Gly Ile Tyr Leu Leu Val
        435                 440                 445

Gly Gln Leu Trp Tyr Phe Trp Arg Arg His Val Phe Ile Trp Ile Ser
    450                 455                 460

Phe Ile Asp Ser Tyr Phe Glu Ile Leu Phe Leu Phe Gln Ala Leu Leu
465                 470                 475                 480

Thr Val Val Ser Gln Val Leu Cys Phe Leu Ala Ile Glu Trp Tyr Leu
                485                 490                 495

Pro Leu Leu Val Ser Ala Leu Val Leu Gly Trp Leu Asn Leu Leu Tyr
            500                 505                 510

Tyr Thr Arg Gly Phe Gln His Thr Gly Ile Tyr Ser Val Met Ile Gln
        515                 520                 525

Lys Val Ile Leu Arg Asp Leu Leu Arg Phe Leu Leu Ile Tyr Leu Val
    530                 535                 540

Phe Leu Phe Gly Phe Ala Val Ala Leu Val Ser Leu Ser Gln Glu Ala
545                 550                 555                 560

Trp Arg Pro Glu Ala Pro Thr Gly Pro Asn Ala Thr Glu Ser Val Gln
                565                 570                 575

Pro Met Glu Gly Gln Glu Asp Glu Gly Asn Gly Ala Gln Tyr Arg Gly
            580                 585                 590

Ile Leu Glu Ala Ser Leu Glu Leu Phe Lys Phe Thr Ile Gly Met Gly
        595                 600                 605

Glu Leu Ala Phe Gln Glu Gln Leu His Phe Arg Gly Met Val Leu Leu
    610                 615                 620

Leu Leu Leu Ala Tyr Val Leu Leu Thr Tyr Ile Leu Leu Leu Asn Met
625                 630                 635                 640

Leu Ile Ala Leu Met Ser Glu Thr Val Asn Ser Val Ala Thr Asp Ser
                645                 650                 655

Trp Ser Ile Trp Lys Leu Gln Lys Ala Ile Ser Val Leu Glu Met Glu
            660                 665                 670

Asn Gly Tyr Trp Trp Cys Arg Lys Lys Gln Arg Ala Gly Val Met Leu
        675                 680                 685

Thr Val Gly Thr Lys Pro Asp Gly Ser Pro Asp Glu Arg Trp Cys Phe
    690                 695                 700

Arg Val Glu Glu Val Asn Trp Ala Ser Trp Glu Gln Thr Leu Pro Thr
705                 710                 715                 720

Leu Cys Glu Asp Pro Ser Gly Ala Gly Val Pro Arg Thr Leu Glu Asn
                725                 730                 735

Pro Val Leu Ala Ser Pro Pro Lys Glu Asp Glu Asp Gly Ala Ser Glu
            740                 745                 750

Glu Asn Tyr Val Pro Val Gln Leu Leu Gln Ser Asn
        755                 760

<210> SEQ ID NO 6
<211> LENGTH: 2292
<212> TYPE: DNA

<213> ORGANISM: Homo sapiens
<220> FEATURE:
<221> NAME/KEY: CDS
<222> LOCATION: (1)..(2292)

<400> SEQUENCE: 6

```
atg acc tca ccc tcc agc tct cca gtt ttc agg ttg gag aca tta gat      48
Met Thr Ser Pro Ser Ser Ser Pro Val Phe Arg Leu Glu Thr Leu Asp
  1               5                  10                  15 gga ggc caa gaa gat ggc tct gag gcg gac aga gga aag ctg gat ttt      96
Gly Gly Gln Glu Asp Gly Ser Glu Ala Asp Arg Gly Lys Leu Asp Phe
             20                  25                  30 ggg agc ggg ctg cct ccc atg gag tca cag ttc cag ggc gag gac cgg     144
Gly Ser Gly Leu Pro Pro Met Glu Ser Gln Phe Gln Gly Glu Asp Arg
         35                  40                  45 aaa ttc gcc cct cag ata aga gtc aac ctc aac tac cga aag gga aca     192
Lys Phe Ala Pro Gln Ile Arg Val Asn Leu Asn Tyr Arg Lys Gly Thr
     50                  55                  60 ggt gcc agt cag ccg gat cca aac cga ttt gac cga gat cgg ctc ttc     240
Gly Ala Ser Gln Pro Asp Pro Asn Arg Phe Asp Arg Asp Arg Leu Phe
 65                  70                  75                  80 aat gcg gtc tcc cgg ggt gtc ccc gag gat ctg gct gga ctt cca gag     288
Asn Ala Val Ser Arg Gly Val Pro Glu Asp Leu Ala Gly Leu Pro Glu
                 85                  90                  95 tac ctg agc aag acc agc aag tac ctc acc gac tcg gaa tac aca gag     336
Tyr Leu Ser Lys Thr Ser Lys Tyr Leu Thr Asp Ser Glu Tyr Thr Glu
            100                 105                 110 ggc tcc aca ggt aag acg tgc ctg atg aag gct gtg ctg aac ctt aag     384
Gly Ser Thr Gly Lys Thr Cys Leu Met Lys Ala Val Leu Asn Leu Lys
        115                 120                 125 gac gga gtc aat gcc tgc att ctg cca ctg ctg cag atc gac agg gac     432
Asp Gly Val Asn Ala Cys Ile Leu Pro Leu Leu Gln Ile Asp Arg Asp
    130                 135                 140 tct ggc aat cct cag ccc ctg gta aat gcc cag tgc aca gat gac tat     480
Ser Gly Asn Pro Gln Pro Leu Val Asn Ala Gln Cys Thr Asp Asp Tyr
145                 150                 155                 160 tac cga ggc cac agc gct ctg cac atc gcc att gag aag agg agt ctg     528
Tyr Arg Gly His Ser Ala Leu His Ile Ala Ile Glu Lys Arg Ser Leu
                165                 170                 175 cag tgt gtg aag ctc ctg gtg gag aat ggg gcc aat gtg cat gcc cgg     576
Gln Cys Val Lys Leu Leu Val Glu Asn Gly Ala Asn Val His Ala Arg
            180                 185                 190 gcc tgc ggc cgc ttc ttc cag aag ggc caa ggg act tgc ttt tat ttc     624
Ala Cys Gly Arg Phe Phe Gln Lys Gly Gln Gly Thr Cys Phe Tyr Phe
        195                 200                 205 ggt gag cta ccc ctc tct ttg gcc gct tgc acc aag cag tgg gat gtg     672
Gly Glu Leu Pro Leu Ser Leu Ala Ala Cys Thr Lys Gln Trp Asp Val
    210                 215                 220 gta agc tac ctc ctg gag aac cca cac cag ccc gcc agc ctg cag gcc     720
Val Ser Tyr Leu Leu Glu Asn Pro His Gln Pro Ala Ser Leu Gln Ala
225                 230                 235                 240 act gac tcc cag ggc aac aca gtc ctg cat gcc cta gtg atg atc tcg     768
Thr Asp Ser Gln Gly Asn Thr Val Leu His Ala Leu Val Met Ile Ser
                245                 250                 255 gac aac tca gct gag aac att gca ctg gtg acc agc atg tat gat ggg     816
Asp Asn Ser Ala Glu Asn Ile Ala Leu Val Thr Ser Met Tyr Asp Gly
            260                 265                 270 ctc ctc caa gct ggg gcc cgc ctc tgc cct acc gtg cag ctt gag gac     864
Leu Leu Gln Ala Gly Ala Arg Leu Cys Pro Thr Val Gln Leu Glu Asp
        275                 280                 285 atc cgc aac ctg cag gat ctc acg cct ctg aag ctg gcc gcc aag gag     912
Ile Arg Asn Leu Gln Asp Leu Thr Pro Leu Lys Leu Ala Ala Lys Glu
```

```
                                          -continued

Ile Arg Asn Leu Gln Asp Leu Thr Pro Leu Lys Leu Ala Ala Lys Glu
    290                 295                 300 ggc aag atc gag att ttc agg cac atc ctg cag cgg gag ttt tca gga    960
Gly Lys Ile Glu Ile Phe Arg His Ile Leu Gln Arg Glu Phe Ser Gly
305                 310                 315                 320 ctg agc cac ctt tcc cga aag ttc acc gag tgg tgc tat ggg cct gtc   1008
Leu Ser His Leu Ser Arg Lys Phe Thr Glu Trp Cys Tyr Gly Pro Val
                325                 330                 335 cgg gtg tcg ctg tat gac ctg gct tct gtg gac agc tgt gag gag aac   1056
Arg Val Ser Leu Tyr Asp Leu Ala Ser Val Asp Ser Cys Glu Glu Asn
            340                 345                 350 tca gtg ctg gag atc att gcc ttt cat tgc aag agc ccg cac cga cac   1104
Ser Val Leu Glu Ile Ile Ala Phe His Cys Lys Ser Pro His Arg His
        355                 360                 365 cga atg gtc gtt ttg gag ccc ctg aac aaa ctg ctg cag gcg aaa tgg   1152
Arg Met Val Val Leu Glu Pro Leu Asn Lys Leu Leu Gln Ala Lys Trp
    370                 375                 380 gat ctg ctc atc ccc aag ttc ttc tta aac ttc ctg tgt aat ctg atc   1200
Asp Leu Leu Ile Pro Lys Phe Phe Leu Asn Phe Leu Cys Asn Leu Ile
385                 390                 395                 400 tac atg ttc atc ttc acc gct gtt gcc tac cat cag cct acc ctg aag   1248
Tyr Met Phe Ile Phe Thr Ala Val Ala Tyr His Gln Pro Thr Leu Lys
                405                 410                 415 aag cag gcc gcc cct cac ctg aaa gcg gag gtt gga aac tcc atg ctg   1296
Lys Gln Ala Ala Pro His Leu Lys Ala Glu Val Gly Asn Ser Met Leu
            420                 425                 430 ctg acg ggc cac atc ctt atc ctg cta ggg ggg atc tac ctc ctc gtg   1344
Leu Thr Gly His Ile Leu Ile Leu Leu Gly Gly Ile Tyr Leu Leu Val
        435                 440                 445 ggc cag ctg tgg tac ttc tgg cgg cgc cac gtg ttc atc tgg atc tcg   1392
Gly Gln Leu Trp Tyr Phe Trp Arg Arg His Val Phe Ile Trp Ile Ser
    450                 455                 460 ttc ata gac agc tac ttt gaa atc ctc ttc ctg ttc cag gcc ctg ctc   1440
Phe Ile Asp Ser Tyr Phe Glu Ile Leu Phe Leu Phe Gln Ala Leu Leu
465                 470                 475                 480 aca gtg gtg tcc cag gtg ctg tgt ttc ctg gcc atc gag tgg tac ctg   1488
Thr Val Val Ser Gln Val Leu Cys Phe Leu Ala Ile Glu Trp Tyr Leu
                485                 490                 495 ccc ctg ctt gtg tct gcg ctg gtg ctg ggc tgg ctg aac ctg ctt tac   1536
Pro Leu Leu Val Ser Ala Leu Val Leu Gly Trp Leu Asn Leu Leu Tyr
            500                 505                 510 tat aca cgt ggc ttc cag cac aca ggc atc tac agt gtc atg atc cag   1584
Tyr Thr Arg Gly Phe Gln His Thr Gly Ile Tyr Ser Val Met Ile Gln
        515                 520                 525 aag gtc atc ctg cgg gac ctg ctg cgc ttc ctt ctg atc tac tta gtc   1632
Lys Val Ile Leu Arg Asp Leu Leu Arg Phe Leu Leu Ile Tyr Leu Val
    530                 535                 540 ttc ctt ttc ggc ttc gct gta gcc ctg gtg agc ctg agc cag gag gct   1680
Phe Leu Phe Gly Phe Ala Val Ala Leu Val Ser Leu Ser Gln Glu Ala
545                 550                 555                 560 tgg cgc ccc gaa gct cct aca ggc ccc aat gcc aca gag tca gtg cag   1728
Trp Arg Pro Glu Ala Pro Thr Gly Pro Asn Ala Thr Glu Ser Val Gln
                565                 570                 575 ccc atg gag gga cag gag gac gag ggc aac ggg gcc cag tac agg ggt   1776
Pro Met Glu Gly Gln Glu Asp Glu Gly Asn Gly Ala Gln Tyr Arg Gly
            580                 585                 590 atc ctg gaa gcc tcc ttg gag ctc ttc aaa ttc acc atc ggc atg ggc   1824
Ile Leu Glu Ala Ser Leu Glu Leu Phe Lys Phe Thr Ile Gly Met Gly
        595                 600                 605 gag ctg gcc ttc cag gag cag ctg cac ttc cgc ggc atg gtg ctg ctg   1872
```

-continued

| | | |
|---|---|---|
| Glu Leu Ala Phe Gln Glu Gln Leu His Phe Arg Gly Met Val Leu Leu<br>610                     615                     620 | | |
| ctg ctg ctg gcc tac gtg ctg ctc acc tac atc ctg ctg ctc aac atg<br>Leu Leu Leu Ala Tyr Val Leu Leu Thr Tyr Ile Leu Leu Leu Asn Met<br>625                     630                     635                     640 | 1920 | |
| ctc atc gcc ctc atg agc gag acc gtc aac agt gtc gcc act gac agc<br>Leu Ile Ala Leu Met Ser Glu Thr Val Asn Ser Val Ala Thr Asp Ser<br>                     645                     650                     655 | 1968 | |
| tgg agc atc tgg aag ctg cag aaa gcc atc tct gtc ctg gag atg gag<br>Trp Ser Ile Trp Lys Leu Gln Lys Ala Ile Ser Val Leu Glu Met Glu<br>                        660                     665                     670 | 2016 | |
| aat ggc tat tgg tgg tgc agg aag aag cag cgg gca ggt gtg atg ctg<br>Asn Gly Tyr Trp Trp Cys Arg Lys Lys Gln Arg Ala Gly Val Met Leu<br>             675                     680                     685 | 2064 | |
| acc gtt ggc act aag cca gat ggc agc ccg gat gag cgc tgg tgc ttc<br>Thr Val Gly Thr Lys Pro Asp Gly Ser Pro Asp Glu Arg Trp Cys Phe<br>       690                     695                     700 | 2112 | |
| agg gtg gag gag gtg aac tgg gct tca tgg gag cag acg ctg cct acg<br>Arg Val Glu Glu Val Asn Trp Ala Ser Trp Glu Gln Thr Leu Pro Thr<br>705                     710                     715                     720 | 2160 | |
| ctg tgt gag gac ccg tca ggg gca ggt gtc cct cga act ctc gag aac<br>Leu Cys Glu Asp Pro Ser Gly Ala Gly Val Pro Arg Thr Leu Glu Asn<br>                        725                     730                     735 | 2208 | |
| cct gtc ctg gct tcc cct ccc aag gag gat gag gat ggt gcc tct gag<br>Pro Val Leu Ala Ser Pro Pro Lys Glu Asp Glu Asp Gly Ala Ser Glu<br>             740                     745                     750 | 2256 | |
| gaa aac tat gtg ccc gtc cag ctc ctc cag tcc aac<br>Glu Asn Tyr Val Pro Val Gln Leu Leu Gln Ser Asn<br>755                     760 | 2292 | |

<210> SEQ ID NO 7
<211> LENGTH: 1489
<212> TYPE: DNA
<213> ORGANISM: Homo sapiens
<220> FEATURE:
<221> NAME/KEY: CDS
<222> LOCATION: (3)..(1310)

<400> SEQUENCE: 7

| | | |
|---|---|---|
| gc ggc cgc ttc ttc cag aag ggc caa ggg act tgc ttt tat ttc ggt<br>    Gly Arg Phe Phe Gln Lys Gly Gln Gly Thr Cys Phe Tyr Phe Gly<br>    1                 5                     10                   15 | 47 | |
| gag cta ccc ctc tct ttg gcc gct tgc acc aag cag tgg gat gtg gta<br>Glu Leu Pro Leu Ser Leu Ala Ala Cys Thr Lys Gln Trp Asp Val Val<br>                   20                   25                     30 | 95 | |
| agc tac ctc ctg gag aac cca cac cag ccc gcc agc ctg cag gcc act<br>Ser Tyr Leu Leu Glu Asn Pro His Gln Pro Ala Ser Leu Gln Ala Thr<br>         35                     40                     45 | 143 | |
| gac tcc cag ggc aac aca gtc ctg cat gcc cta gtg atg atc tcg gac<br>Asp Ser Gln Gly Asn Thr Val Leu His Ala Leu Val Met Ile Ser Asp<br>50                     55                     60 | 191 | |
| aac tca gct gag aac att gca ctg gtg acc agc atg tat gat ggg ctc<br>Asn Ser Ala Glu Asn Ile Ala Leu Val Thr Ser Met Tyr Asp Gly Leu<br>65                     70                     75 | 239 | |
| ctc caa gct ggg gcc cgc ctc tgc cct acc gtg cag ctt gag gac atc<br>Leu Gln Ala Gly Ala Arg Leu Cys Pro Thr Val Gln Leu Glu Asp Ile<br>80                     85                     90                   95 | 287 | |
| cgc aac ctg cag gat ctc acg cct ctg aag ctg gcc gcc aag gag ggc<br>Arg Asn Leu Gln Asp Leu Thr Pro Leu Lys Leu Ala Ala Lys Glu Gly<br>                 100                   105                  110 | 335 | |
| aag atc gag att ttc agg cac atc ctg cag cgg gag ttt tca gga ctg<br>Lys Ile Glu Ile Phe Arg His Ile Leu Gln Arg Glu Phe Ser Gly Leu | 383 | |

```
                115                     120                     125
agc cac ctt tcc cga aag ttc acc gag tgg tgc tat ggg cct gtc cgg        431
Ser His Leu Ser Arg Lys Phe Thr Glu Trp Cys Tyr Gly Pro Val Arg
        130                     135                     140 gtg tcg ctg tat gac ctg gct tct gtg gac agc tgt gag gag aac tca        479
Val Ser Leu Tyr Asp Leu Ala Ser Val Asp Ser Cys Glu Glu Asn Ser
145                     150                     155 gtg ctg gag atc att gcc ttt cat tgc aag agc ccg cac cga cac cga        527
Val Leu Glu Ile Ile Ala Phe His Cys Lys Ser Pro His Arg His Arg
160                     165                     170                     175 atg gtc gtt ttg gag ccc ctg aac aaa ctg ctg cag gcg aaa tgg gat        575
Met Val Val Leu Glu Pro Leu Asn Lys Leu Leu Gln Ala Lys Trp Asp
                180                     185                     190 ctc ctc atc ccc aag ttc ttc tta aac ttc ctg tgt aat ctg atc tac        623
Leu Leu Ile Pro Lys Phe Phe Leu Asn Phe Leu Cys Asn Leu Ile Tyr
                195                     200                     205 atg ttc atc ttc acc gct gtt gcc tac cat cag cct acc ctg aag aag        671
Met Phe Ile Phe Thr Ala Val Ala Tyr His Gln Pro Thr Leu Lys Lys
        210                     215                     220 cag gcc gcc cct cac ctg aaa gcg gag gtt gga aac tcc atg ctg ctg        719
Gln Ala Ala Pro His Leu Lys Ala Glu Val Gly Asn Ser Met Leu Leu
225                     230                     235 acg ggc cac atc ctt atc ctg cta ggg ggg atc tac ctc ctc gtg ggc        767
Thr Gly His Ile Leu Ile Leu Leu Gly Gly Ile Tyr Leu Leu Val Gly
240                     245                     250                     255 cag ctg tgg tac ttc tgg cgg cgc cac gtg ttc atc tgg atc tcg ttc        815
Gln Leu Trp Tyr Phe Trp Arg Arg His Val Phe Ile Trp Ile Ser Phe
                260                     265                     270 ata gac agc tac ttt gaa atc ctc ttc ctg ttc cag gcc ctg ctc aca        863
Ile Asp Ser Tyr Phe Glu Ile Leu Phe Leu Phe Gln Ala Leu Leu Thr
                275                     280                     285 gtg gtg tcc cag gtg ctg tgt ttc ctg gcc atc gag tgg tac ctg ccc        911
Val Val Ser Gln Val Leu Cys Phe Leu Ala Ile Glu Trp Tyr Leu Pro
        290                     295                     300 ctg ctt gtg tct gcg ctg gtg ctg ggc tgg ctg aac ctg ctt tac tat        959
Leu Leu Val Ser Ala Leu Val Leu Gly Trp Leu Asn Leu Leu Tyr Tyr
305                     310                     315 aca cgt ggc ttc cag cac aca ggc atc tac agt gtc atg atc cag aag       1007
Thr Arg Gly Phe Gln His Thr Gly Ile Tyr Ser Val Met Ile Gln Lys
320                     325                     330                     335 aaa gcc atc tct gtc ctg gag atg gag aat ggc tat tgg tgg tgc agg       1055
Lys Ala Ile Ser Val Leu Glu Met Glu Asn Gly Tyr Trp Trp Cys Arg
                340                     345                     350 aag aag cag cgg gca ggt gtg atg ctg acc gtt ggc act aag cca gat       1103
Lys Lys Gln Arg Ala Gly Val Met Leu Thr Val Gly Thr Lys Pro Asp
                355                     360                     365 ggc agc ccg gat gag cgc tgg tgc ttc agg gtg gag gag gtg aac tgg       1151
Gly Ser Pro Asp Glu Arg Trp Cys Phe Arg Val Glu Glu Val Asn Trp
        370                     375                     380 gct tca tgg gag cag acg ctg cct acg ctg tgt gag gac ccg tca ggg       1199
Ala Ser Trp Glu Gln Thr Leu Pro Thr Leu Cys Glu Asp Pro Ser Gly
385                     390                     395 gca ggt gtc cct cga act ctc gag aac cct gtc ctg gct tcc cct ccc       1247
Ala Gly Val Pro Arg Thr Leu Glu Asn Pro Val Leu Ala Ser Pro Pro
400                     405                     410                     415 aag gag gat gag gat ggt gcc tct gag gaa aac tat gtg ccc gtc cag       1295
Lys Glu Asp Glu Asp Gly Ala Ser Glu Glu Asn Tyr Val Pro Val Gln
                420                     425                     430 ctc ctc cag tcc aac tgatggccca gatgcagcag gaggccagag gacagagcag       1350
Leu Leu Gln Ser Asn
```

-continued

```
                    435
aggatctttc caaccacatc tgctggctct ggggtcccag tgaattctgg tggcaaatat    1410
atattttcac taactcaaaa aaaaaaaaaa aaaaaaaaaa aaaaaaaaaa aaaaaaaagg    1470
agcggacgcg tgggtcgac                                                 1489

<210> SEQ ID NO 8
<211> LENGTH: 436
<212> TYPE: PRT
<213> ORGANISM: Homo sapiens

<400> SEQUENCE: 8

Gly Arg Phe Phe Gln Lys Gly Gln Gly Thr Cys Phe Tyr Phe Gly Glu
  1               5                  10                  15

Leu Pro Leu Ser Leu Ala Ala Cys Thr Lys Gln Trp Asp Val Val Ser
                 20                  25                  30

Tyr Leu Leu Glu Asn Pro His Gln Pro Ala Ser Leu Gln Ala Thr Asp
             35                  40                  45

Ser Gln Gly Asn Thr Val Leu His Ala Leu Val Met Ile Ser Asp Asn
         50                  55                  60

Ser Ala Glu Asn Ile Ala Leu Val Thr Ser Met Tyr Asp Gly Leu Leu
 65                  70                  75                  80

Gln Ala Gly Ala Arg Leu Cys Pro Thr Val Gln Leu Glu Asp Ile Arg
                 85                  90                  95

Asn Leu Gln Asp Leu Thr Pro Leu Lys Leu Ala Ala Lys Glu Gly Lys
            100                 105                 110

Ile Glu Ile Phe Arg His Ile Leu Gln Arg Glu Phe Ser Gly Leu Ser
        115                 120                 125

His Leu Ser Arg Lys Phe Thr Glu Trp Cys Tyr Gly Pro Val Arg Val
    130                 135                 140

Ser Leu Tyr Asp Leu Ala Ser Val Asp Ser Cys Glu Glu Asn Ser Val
145                 150                 155                 160

Leu Glu Ile Ile Ala Phe His Cys Lys Ser Pro His Arg His Arg Met
                165                 170                 175

Val Val Leu Glu Pro Leu Asn Lys Leu Leu Gln Ala Lys Trp Asp Leu
            180                 185                 190

Leu Ile Pro Lys Phe Phe Leu Asn Phe Leu Cys Asn Leu Ile Tyr Met
        195                 200                 205

Phe Ile Phe Thr Ala Val Ala Tyr His Gln Pro Thr Leu Lys Lys Gln
    210                 215                 220

Ala Ala Pro His Leu Lys Ala Glu Val Gly Asn Ser Met Leu Leu Thr
225                 230                 235                 240

Gly His Ile Leu Ile Leu Leu Gly Gly Ile Tyr Leu Leu Val Gly Gln
                245                 250                 255

Leu Trp Tyr Phe Trp Arg Arg His Val Phe Ile Trp Ile Ser Phe Ile
            260                 265                 270

Asp Ser Tyr Phe Glu Ile Leu Phe Leu Phe Gln Ala Leu Leu Thr Val
        275                 280                 285

Val Ser Gln Val Leu Cys Phe Leu Ala Ile Glu Trp Tyr Leu Pro Leu
    290                 295                 300

Leu Val Ser Ala Leu Val Leu Gly Trp Leu Asn Leu Leu Tyr Tyr Thr
305                 310                 315                 320

Arg Gly Phe Gln His Thr Gly Ile Tyr Ser Val Met Ile Gln Lys Lys
                325                 330                 335

Ala Ile Ser Val Leu Glu Met Glu Asn Gly Tyr Trp Trp Cys Arg Lys
```

```
                           340                 345                 350
Lys Gln Arg Ala Gly Val Met Leu Thr Val Gly Thr Lys Pro Asp Gly
                355                 360                 365

Ser Pro Asp Glu Arg Trp Cys Phe Arg Val Glu Glu Val Asn Trp Ala
            370                 375                 380

Ser Trp Glu Gln Thr Leu Pro Thr Leu Cys Glu Asp Pro Ser Gly Ala
385                 390                 395                 400

Gly Val Pro Arg Thr Leu Glu Asn Pro Val Leu Ala Ser Pro Pro Lys
                405                 410                 415

Glu Asp Glu Asp Gly Ala Ser Glu Glu Asn Tyr Val Pro Val Gln Leu
            420                 425                 430

Leu Gln Ser Asn
        435

<210> SEQ ID NO 9
<211> LENGTH: 1308
<212> TYPE: DNA
<213> ORGANISM: Homo sapiens
<220> FEATURE:
<221> NAME/KEY: CDS
<222> LOCATION: (1)..(1308)

<400> SEQUENCE: 9 ggc cgc ttc ttc cag aag ggc caa ggg act tgc ttt tat ttc ggt gag       48
Gly Arg Phe Phe Gln Lys Gly Gln Gly Thr Cys Phe Tyr Phe Gly Glu
  1               5                  10                  15 cta ccc ctc tct ttg gcc gct tgc acc aag cag tgg gat gtg gta agc       96
Leu Pro Leu Ser Leu Ala Ala Cys Thr Lys Gln Trp Asp Val Val Ser
             20                  25                  30 tac ctc ctg gag aac cca cac cag ccc gcc agc ctg cag gcc act gac      144
Tyr Leu Leu Glu Asn Pro His Gln Pro Ala Ser Leu Gln Ala Thr Asp
         35                  40                  45 tcc cag ggc aac aca gtc ctg cat gcc cta gtg atg atc tcg gac aac      192
Ser Gln Gly Asn Thr Val Leu His Ala Leu Val Met Ile Ser Asp Asn
     50                  55                  60 tca gct gag aac att gca ctg gtg acc agc atg tat gat ggg ctc ctc      240
Ser Ala Glu Asn Ile Ala Leu Val Thr Ser Met Tyr Asp Gly Leu Leu
 65                  70                  75                  80 caa gct ggg gcc cgc ctc tgc cct acc gtg cag ctt gag gac atc cgc      288
Gln Ala Gly Ala Arg Leu Cys Pro Thr Val Gln Leu Glu Asp Ile Arg
                 85                  90                  95 aac ctg cag gat ctc acg cct ctg aag ctg gcc gcc aag gag ggc aag      336
Asn Leu Gln Asp Leu Thr Pro Leu Lys Leu Ala Ala Lys Glu Gly Lys
            100                 105                 110 atc gag att ttc agg cac atc ctg cag cgg gag ttt tca gga ctg agc      384
Ile Glu Ile Phe Arg His Ile Leu Gln Arg Glu Phe Ser Gly Leu Ser
        115                 120                 125 cac ctt tcc cga aag ttc acc gag tgg tgc tat ggg cct gtc cgg gtg      432
His Leu Ser Arg Lys Phe Thr Glu Trp Cys Tyr Gly Pro Val Arg Val
    130                 135                 140 tcg ctg tat gac ctg gct tct gtg gac agc tgt gag gag aac tca gtg      480
Ser Leu Tyr Asp Leu Ala Ser Val Asp Ser Cys Glu Glu Asn Ser Val
145                 150                 155                 160 ctg gag atc att gcc ttt cat tgc aag agc ccg cac cga cac cga atg      528
Leu Glu Ile Ile Ala Phe His Cys Lys Ser Pro His Arg His Arg Met
                165                 170                 175 gtc gtt ttg gag ccc ctg aac aaa ctg ctg cag gcg aaa tgg gat ctg      576
Val Val Leu Glu Pro Leu Asn Lys Leu Leu Gln Ala Lys Trp Asp Leu
            180                 185                 190 ctc atc ccc aag ttc ttc tta aac ttc ctg tgt aat ctg atc tac atg      624
```

```
Leu Ile Pro Lys Phe Phe Leu Asn Phe Leu Cys Asn Leu Ile Tyr Met
        195                 200                 205 ttc atc ttc acc gct gtt gcc tac cat cag cct acc ctg aag aag cag       672
Phe Ile Phe Thr Ala Val Ala Tyr His Gln Pro Thr Leu Lys Lys Gln
        210                 215                 220 gcc gcc cct cac ctg aaa gcg gag gtt gga aac tcc atg ctg ctg acg       720
Ala Ala Pro His Leu Lys Ala Glu Val Gly Asn Ser Met Leu Leu Thr
225                 230                 235                 240 ggc cac atc ctt atc ctg cta ggg ggg atc tac ctc ctc gtg ggc cag       768
Gly His Ile Leu Ile Leu Leu Gly Gly Ile Tyr Leu Leu Val Gly Gln
                245                 250                 255 ctg tgg tac ttc tgg cgg cgc cac gtg ttc atc tgg atc tcg ttc ata       816
Leu Trp Tyr Phe Trp Arg Arg His Val Phe Ile Trp Ile Ser Phe Ile
                260                 265                 270 gac agc tac ttt gaa atc ctc ttc ctg ttc cag gcc ctg ctc aca gtg       864
Asp Ser Tyr Phe Glu Ile Leu Phe Leu Phe Gln Ala Leu Leu Thr Val
            275                 280                 285 gtg tcc cag gtg ctg tgt ttc ctg gcc atc gag tgg tac ctg ccc ctg       912
Val Ser Gln Val Leu Cys Phe Leu Ala Ile Glu Trp Tyr Leu Pro Leu
        290                 295                 300 ctt gtg tct gcg ctg gtg ctg ggc tgg ctg aac ctg ctt tac tat aca       960
Leu Val Ser Ala Leu Val Leu Gly Trp Leu Asn Leu Leu Tyr Tyr Thr
305                 310                 315                 320 cgt ggc ttc cag cac aca ggc atc tac agt gtc atg atc cag aag aaa      1008
Arg Gly Phe Gln His Thr Gly Ile Tyr Ser Val Met Ile Gln Lys Lys
                325                 330                 335 gcc atc tct gtc ctg gag atg gag aat ggc tat tgg tgg tgc agg aag      1056
Ala Ile Ser Val Leu Glu Met Glu Asn Gly Tyr Trp Trp Cys Arg Lys
                340                 345                 350 aag cag cgg gca ggt gtg atg ctg acc gtt ggc act aag cca gat ggc      1104
Lys Gln Arg Ala Gly Val Met Leu Thr Val Gly Thr Lys Pro Asp Gly
            355                 360                 365 agc ccg gat gag cgc tgg tgc ttc agg gtg gag gag gtg aac tgg gct      1152
Ser Pro Asp Glu Arg Trp Cys Phe Arg Val Glu Glu Val Asn Trp Ala
        370                 375                 380 tca tgg gag cag acg ctg cct acg ctg tgt gag gac ccg tca ggg gca      1200
Ser Trp Glu Gln Thr Leu Pro Thr Leu Cys Glu Asp Pro Ser Gly Ala
385                 390                 395                 400 ggt gtc cct cga act ctc gag aac cct gtc ctg gct tcc cct ccc aag      1248
Gly Val Pro Arg Thr Leu Glu Asn Pro Val Leu Ala Ser Pro Pro Lys
                405                 410                 415 gag gat gag gat ggt gcc tct gag gaa aac tat gtg ccc gtc cag ctc      1296
Glu Asp Glu Asp Gly Ala Ser Glu Glu Asn Tyr Val Pro Val Gln Leu
                420                 425                 430 ctc cag tcc aac                                                      1308
Leu Gln Ser Asn
        435

<210> SEQ ID NO 10
<211> LENGTH: 1794
<212> TYPE: DNA
<213> ORGANISM: Rattus sp.
<220> FEATURE:
<221> NAME/KEY: CDS
<222> LOCATION: (2)..(1663)

<400> SEQUENCE: 10 g tcg acc cac gcg tcc gct ctt tct ctg gct gcg tgc acc aag cag tgg     49
  Ser Thr His Ala Ser Ala Leu Ser Leu Ala Ala Cys Thr Lys Gln Trp
  1               5                   10                  15 gat gtg gtg acc tac ctc ctg gag aac cca cac cag ccg gcc agc ctg       97
Asp Val Val Thr Tyr Leu Leu Glu Asn Pro His Gln Pro Ala Ser Leu
```

-continued

```
            20                  25                  30 gag gcc acc gac tcc ctg ggc aac aca gtc ctg cat gct ctg gta atg    145
Glu Ala Thr Asp Ser Leu Gly Asn Thr Val Leu His Ala Leu Val Met
         35                  40                  45 att gca gat aac tcg cct gag aac agt gcc ctg gtg atc cac atg tac    193
Ile Ala Asp Asn Ser Pro Glu Asn Ser Ala Leu Val Ile His Met Tyr
 50                  55                  60 gac ggg ctt cta caa atg ggg gcg cgc ctc tgc ccc act gtg cag ctt    241
Asp Gly Leu Leu Gln Met Gly Ala Arg Leu Cys Pro Thr Val Gln Leu
 65                  70                  75                  80 gag gaa atc tcc aac cac caa ggc ctc aca ccc ctg aaa cta gcc gcc    289
Glu Glu Ile Ser Asn His Gln Gly Leu Thr Pro Leu Lys Leu Ala Ala
                 85                  90                  95 aag gaa ggc aaa atc gag att ttc agg cac att ctg cag cgg gaa ttc    337
Lys Glu Gly Lys Ile Glu Ile Phe Arg His Ile Leu Gln Arg Glu Phe
            100                 105                 110 tca gga ccg tac cag ccc ctt tcc cga aag ttt act gag tgg tgt tac    385
Ser Gly Pro Tyr Gln Pro Leu Ser Arg Lys Phe Thr Glu Trp Cys Tyr
        115                 120                 125 ggt cct gtg cgg gta tcg ctg tac gac ctg tcc tct gtg gac agc tgg    433
Gly Pro Val Arg Val Ser Leu Tyr Asp Leu Ser Ser Val Asp Ser Trp
    130                 135                 140 gaa aag aac tcg gtg ctg gag atc atc gct ttt cat tgc aag agc ccg    481
Glu Lys Asn Ser Val Leu Glu Ile Ile Ala Phe His Cys Lys Ser Pro
145                 150                 155                 160 aac cgg cac cgc atg gtg gtt tta gaa cca ctg aac aag ctt ctg cag    529
Asn Arg His Arg Met Val Val Leu Glu Pro Leu Asn Lys Leu Leu Gln
                165                 170                 175 gag aaa tgg gat cgg ctc gtc tca aga ttc ttc ttc aac ttc gcc tgc    577
Glu Lys Trp Asp Arg Leu Val Ser Arg Phe Phe Phe Asn Phe Ala Cys
            180                 185                 190 tac ttg gtc tac atg ttc atc ttc acc gtc gtt gcc tac cac cag cct    625
Tyr Leu Val Tyr Met Phe Ile Phe Thr Val Val Ala Tyr His Gln Pro
        195                 200                 205 tcc ctg gat cag cca gcc atc ccc tca tca aaa gcg act ttt ggg gaa    673
Ser Leu Asp Gln Pro Ala Ile Pro Ser Ser Lys Ala Thr Phe Gly Glu
    210                 215                 220 tcc atg ctg ctg ctg ggc cac att ctg atc ctg ctt ggg ggt att tac    721
Ser Met Leu Leu Leu Gly His Ile Leu Ile Leu Leu Gly Gly Ile Tyr
225                 230                 235                 240 ctc tta ctg ggc cag ctg tgg tac ttt tgg cgg cgg cgc ctg ttt atc    769
Leu Leu Leu Gly Gln Leu Trp Tyr Phe Trp Arg Arg Arg Leu Phe Ile
                245                 250                 255 tgg atc tca ttc atg gac agc tac ttt gaa atc ctc ttt ctc ctt cag    817
Trp Ile Ser Phe Met Asp Ser Tyr Phe Glu Ile Leu Phe Leu Leu Gln
            260                 265                 270 gct ctc ctc aca gtg ctg tcc cag gtg ctg cgc ttc atg gag act gaa    865
Ala Leu Leu Thr Val Leu Ser Gln Val Leu Arg Phe Met Glu Thr Glu
        275                 280                 285 tgg tac cta ccc ctg cta gtg tta tcc cta gtg ctg ggc tgg ctg aac    913
Trp Tyr Leu Pro Leu Leu Val Leu Ser Leu Val Leu Gly Trp Leu Asn
    290                 295                 300 ctg ctt tac tac aca cgg ggc ttt cag cac aca ggc atc tac agt gtc    961
Leu Leu Tyr Tyr Thr Arg Gly Phe Gln His Thr Gly Ile Tyr Ser Val
305                 310                 315                 320 atg atc cag aag gtc atc ctt cga gac ctg ctc cgt ttc ctg ctg gtc   1009
Met Ile Gln Lys Val Ile Leu Arg Asp Leu Leu Arg Phe Leu Leu Val
                325                 330                 335 tac ctg gtc ttc ctt ttc ggc ttt gct gta gcc cta gta agc ttg agc   1057
Tyr Leu Val Phe Leu Phe Gly Phe Ala Val Ala Leu Val Ser Leu Ser
```

```
                        340                 345                 350
aga gag gcc cga agt ccc aaa gcc cct gaa gat aac aac tcc aca gtg        1105
Arg Glu Ala Arg Ser Pro Lys Ala Pro Glu Asp Asn Asn Ser Thr Val
            355                 360                 365 acg gaa cag ccc acg gtg ggc cag gag gag gag cca gct cca tat cgg        1153
Thr Glu Gln Pro Thr Val Gly Gln Glu Glu Glu Pro Ala Pro Tyr Arg
370                 375                 380 agc att ctg gat gcc tcc cta gag ctg ttc aag ttc acc att ggt atg        1201
Ser Ile Leu Asp Ala Ser Leu Glu Leu Phe Lys Phe Thr Ile Gly Met
385                 390                 395                 400 ggg gag ctg gct ttc cag gaa cag ctg cgt ttt cgt ggg gtg gtc ctg        1249
Gly Glu Leu Ala Phe Gln Glu Gln Leu Arg Phe Arg Gly Val Val Leu
            405                 410                 415 ctg ttg ctg ttg gcc tac gtc ctt ctc acc tac gtc ctg ctc ctc aac        1297
Leu Leu Leu Leu Ala Tyr Val Leu Leu Thr Tyr Val Leu Leu Leu Asn
                420                 425                 430 atg ctc att gct ctc atg agc gaa act gtc aac cac gtt gct gac aac        1345
Met Leu Ile Ala Leu Met Ser Glu Thr Val Asn His Val Ala Asp Asn
            435                 440                 445 agc tgg agc atc tgg aag ttg cag aaa gcc atc tct gtc ttg gag atg        1393
Ser Trp Ser Ile Trp Lys Leu Gln Lys Ala Ile Ser Val Leu Glu Met
450                 455                 460 gag aat ggt tac tgg tgg tgc cgg agg aag aaa cat cgt gaa ggg agg        1441
Glu Asn Gly Tyr Trp Trp Cys Arg Arg Lys Lys His Arg Glu Gly Arg
465                 470                 475                 480 ctg ctg aaa gtc ggc acc agg ggg gat ggt acc cct gat gag cgc tgg        1489
Leu Leu Lys Val Gly Thr Arg Gly Asp Gly Thr Pro Asp Glu Arg Trp
            485                 490                 495 tgc ttc agg gtg gag gaa gta aat tgg gct gct tgg gag aag act ctt        1537
Cys Phe Arg Val Glu Glu Val Asn Trp Ala Ala Trp Glu Lys Thr Leu
                500                 505                 510 ccc acc tta tct gag gat cca tca ggg cca ggc atc act ggt aat aaa        1585
Pro Thr Leu Ser Glu Asp Pro Ser Gly Pro Gly Ile Thr Gly Asn Lys
            515                 520                 525 aag aac cca acc tct aaa ccg ggg aag aac agt gcc tca gag gaa gac        1633
Lys Asn Pro Thr Ser Lys Pro Gly Lys Asn Ser Ala Ser Glu Glu Asp
530                 535                 540 cat ctg ccc ctt cag gtc ctc cag tcc ccc tgatggccca gatgcagcag         1683
His Leu Pro Leu Gln Val Leu Gln Ser Pro
545                 550 caggctggca ggatggagta gggaatcttc ccagccacac cagaggctac tgaattttgg    1743
tggaaatata aatattttt ttgcataaaa aaaaaaaaa agggcggccg c                1794

<210> SEQ ID NO 11
<211> LENGTH: 554
<212> TYPE: PRT
<213> ORGANISM: Rattus sp.

<400> SEQUENCE: 11

Ser Thr His Ala Ser Ala Leu Ser Leu Ala Ala Cys Thr Lys Gln Trp
1               5                   10                  15

Asp Val Val Thr Tyr Leu Leu Glu Asn Pro His Gln Pro Ala Ser Leu
            20                  25                  30

Glu Ala Thr Asp Ser Leu Gly Asn Thr Val Leu His Ala Leu Val Met
        35                  40                  45

Ile Ala Asp Asn Ser Pro Glu Asn Ser Ala Leu Val Ile His Met Tyr
    50                  55                  60

Asp Gly Leu Leu Gln Met Gly Ala Arg Leu Cys Pro Thr Val Gln Leu
65                  70                  75                  80
```

-continued

```
Glu Glu Ile Ser Asn His Gln Gly Leu Thr Pro Leu Lys Leu Ala Ala
                 85                  90                  95

Lys Glu Gly Lys Ile Glu Ile Phe Arg His Ile Leu Gln Arg Glu Phe
            100                 105                 110

Ser Gly Pro Tyr Gln Pro Leu Ser Arg Lys Phe Thr Glu Trp Cys Tyr
            115                 120                 125

Gly Pro Val Arg Val Ser Leu Tyr Asp Leu Ser Ser Val Asp Ser Trp
130                 135                 140

Glu Lys Asn Ser Val Leu Glu Ile Ile Ala Phe His Cys Lys Ser Pro
145                 150                 155                 160

Asn Arg His Arg Met Val Val Leu Glu Pro Leu Asn Lys Leu Leu Gln
                165                 170                 175

Glu Lys Trp Asp Arg Leu Val Ser Arg Phe Phe Asn Phe Ala Cys
            180                 185                 190

Tyr Leu Val Tyr Met Phe Ile Phe Thr Val Val Ala Tyr His Gln Pro
            195                 200                 205

Ser Leu Asp Gln Pro Ala Ile Pro Ser Ser Lys Ala Thr Phe Gly Glu
210                 215                 220

Ser Met Leu Leu Leu Gly His Ile Leu Ile Leu Leu Gly Gly Ile Tyr
225                 230                 235                 240

Leu Leu Leu Gly Gln Leu Trp Tyr Phe Trp Arg Arg Leu Phe Ile
                245                 250                 255

Trp Ile Ser Phe Met Asp Ser Tyr Phe Glu Ile Leu Phe Leu Leu Gln
            260                 265                 270

Ala Leu Leu Thr Val Leu Ser Gln Val Leu Arg Phe Met Glu Thr Glu
            275                 280                 285

Trp Tyr Leu Pro Leu Leu Val Leu Ser Leu Val Leu Gly Trp Leu Asn
            290                 295                 300

Leu Leu Tyr Tyr Thr Arg Gly Phe Gln His Thr Gly Ile Tyr Ser Val
305                 310                 315                 320

Met Ile Gln Lys Val Ile Leu Arg Asp Leu Leu Arg Phe Leu Leu Val
                325                 330                 335

Tyr Leu Val Phe Leu Phe Gly Phe Ala Val Ala Leu Val Ser Leu Ser
                340                 345                 350

Arg Glu Ala Arg Ser Pro Lys Ala Pro Glu Asp Asn Asn Ser Thr Val
            355                 360                 365

Thr Glu Gln Pro Thr Val Gly Gln Glu Glu Pro Ala Pro Tyr Arg
            370                 375                 380

Ser Ile Leu Asp Ala Ser Leu Glu Leu Phe Lys Phe Thr Ile Gly Met
385                 390                 395                 400

Gly Glu Leu Ala Phe Gln Glu Gln Leu Arg Phe Arg Gly Val Val Leu
                405                 410                 415

Leu Leu Leu Leu Ala Tyr Val Leu Leu Thr Tyr Val Leu Leu Leu Asn
            420                 425                 430

Met Leu Ile Ala Leu Met Ser Glu Thr Val Asn His Val Ala Asp Asn
            435                 440                 445

Ser Trp Ser Ile Trp Lys Leu Gln Lys Ala Ile Ser Val Leu Glu Met
450                 455                 460

Glu Asn Gly Tyr Trp Trp Cys Arg Arg Lys His Arg Glu Gly Arg
465                 470                 475                 480

Leu Leu Lys Val Gly Thr Arg Gly Asp Gly Thr Pro Asp Glu Arg Trp
                485                 490                 495

Cys Phe Arg Val Glu Glu Val Asn Trp Ala Ala Trp Glu Lys Thr Leu
```

```
                    500             505             510
Pro Thr Leu Ser Glu Asp Pro Ser Gly Pro Gly Ile Thr Gly Asn Lys
            515                 520                 525

Lys Asn Pro Thr Ser Lys Pro Gly Lys Asn Ser Ala Ser Glu Glu Asp
        530                 535                 540

His Leu Pro Leu Gln Val Leu Gln Ser Pro
545                 550

<210> SEQ ID NO 12
<211> LENGTH: 1662
<212> TYPE: DNA
<213> ORGANISM: Rattus sp.
<220> FEATURE:
<221> NAME/KEY: CDS
<222> LOCATION: (1)..(1662)

<400> SEQUENCE: 12 tcg acc cac gcg tcc gct ctt tct ctg gct gcg tgc acc aag cag tgg     48
Ser Thr His Ala Ser Ala Leu Ser Leu Ala Ala Cys Thr Lys Gln Trp
  1               5                  10                  15 gat gtg gtg acc tac ctc ctg gag aac cca cac cag ccg gcc agc ctg     96
Asp Val Val Thr Tyr Leu Leu Glu Asn Pro His Gln Pro Ala Ser Leu
                 20                  25                  30 gag gcc acc gac tcc ctg ggc aac aca gtc ctg cat gct ctg gta atg    144
Glu Ala Thr Asp Ser Leu Gly Asn Thr Val Leu His Ala Leu Val Met
             35                  40                  45 att gca gat aac tcg cct gag aac agt gcc ctg gtg atc cac atg tac    192
Ile Ala Asp Asn Ser Pro Glu Asn Ser Ala Leu Val Ile His Met Tyr
         50                  55                  60 gac ggg ctt cta caa atg ggg gcg cgc ctc tgc ccc act gtg cag ctt    240
Asp Gly Leu Leu Gln Met Gly Ala Arg Leu Cys Pro Thr Val Gln Leu
 65                  70                  75                  80 gag gaa atc tcc aac cac caa ggc ctc aca ccc ctg aaa cta gcc gcc    288
Glu Glu Ile Ser Asn His Gln Gly Leu Thr Pro Leu Lys Leu Ala Ala
                 85                  90                  95 aag gaa ggc aaa atc gag att ttc agg cac att ctg cag cgg gaa ttc    336
Lys Glu Gly Lys Ile Glu Ile Phe Arg His Ile Leu Gln Arg Glu Phe
                100                 105                 110 tca gga ccg tac cag ccc ctt tcc cga aag ttt act gag tgg tgt tac    384
Ser Gly Pro Tyr Gln Pro Leu Ser Arg Lys Phe Thr Glu Trp Cys Tyr
             115                 120                 125 ggt cct gtg cgg gta tcg ctg tac gac ctg tcc tct gtg gac agc tgg    432
Gly Pro Val Arg Val Ser Leu Tyr Asp Leu Ser Ser Val Asp Ser Trp
         130                 135                 140 gaa aag aac tcg gtg ctg gag atc atc gct ttt cat tgc aag agc ccg    480
Glu Lys Asn Ser Val Leu Glu Ile Ile Ala Phe His Cys Lys Ser Pro
145                 150                 155                 160 aac cgg cac cgc atg gtg gtt tta gaa cca ctg aac aag ctt ctg cag    528
Asn Arg His Arg Met Val Val Leu Glu Pro Leu Asn Lys Leu Leu Gln
                165                 170                 175 gag aaa tgg gat cgg ctc gtc tca aga ttc ttc ttc aac ttc gcc tgc    576
Glu Lys Trp Asp Arg Leu Val Ser Arg Phe Phe Phe Asn Phe Ala Cys
                180                 185                 190 tac ttg gtc tac atg ttc atc ttc acc gtc gtt gcc tac cac cag cct    624
Tyr Leu Val Tyr Met Phe Ile Phe Thr Val Val Ala Tyr His Gln Pro
             195                 200                 205 tcc ctg gat cag cca gcc atc ccc tca tca aaa gcg act ttt ggg gaa    672
Ser Leu Asp Gln Pro Ala Ile Pro Ser Ser Lys Ala Thr Phe Gly Glu
         210                 215                 220 tcc atg ctg ctg ctg ggc cac att ctg atc ctg ctt ggg ggt att tac    720
Ser Met Leu Leu Leu Gly His Ile Leu Ile Leu Leu Gly Gly Ile Tyr
```

```
                225                 230                 235                 240 ctc tta ctg ggc cag ctg tgg tac ttt tgg cgg cgg cgc ctg ttt atc          768
Leu Leu Leu Gly Gln Leu Trp Tyr Phe Trp Arg Arg Arg Leu Phe Ile
                        245                 250                 255 tgg atc tca ttc atg gac agc tac ttt gaa atc ctc ttt ctc ctt cag          816
Trp Ile Ser Phe Met Asp Ser Tyr Phe Glu Ile Leu Phe Leu Leu Gln
                        260                 265                 270 gct ctg ctc aca gtg ctg tcc cag gtg ctg cgc ttc atg gag act gaa          864
Ala Leu Leu Thr Val Leu Ser Gln Val Leu Arg Phe Met Glu Thr Glu
                        275                 280                 285 tgg tac cta ccc ctg cta gtg tta tcc cta gtg ctg ggc tgg ctg aac          912
Trp Tyr Leu Pro Leu Leu Val Leu Ser Leu Val Leu Gly Trp Leu Asn
                        290                 295                 300 ctg ctt tac tac aca cgg ggc ttt cag cac aca ggc atc tac agt gtc          960
Leu Leu Tyr Tyr Thr Arg Gly Phe Gln His Thr Gly Ile Tyr Ser Val
305                     310                 315                 320 atg atc cag aag gtc atc ctt cga gac ctg ctc cgt ttc ctg ctg gtc          1008
Met Ile Gln Lys Val Ile Leu Arg Asp Leu Leu Arg Phe Leu Leu Val
                        325                 330                 335 tac ctg gtc ttc ctt ttc ggc ttt gct gta gcc cta gta agc ttg agc          1056
Tyr Leu Val Phe Leu Phe Gly Phe Ala Val Ala Leu Val Ser Leu Ser
                        340                 345                 350 aga gag gcc cga agt ccc aaa gcc cct gaa gat aac aac tcc aca gtg          1104
Arg Glu Ala Arg Ser Pro Lys Ala Pro Glu Asp Asn Asn Ser Thr Val
                        355                 360                 365 acg gaa cag ccc acg gtg ggc cag gag gag gag cca gct cca tat cgg          1152
Thr Glu Gln Pro Thr Val Gly Gln Glu Glu Glu Pro Ala Pro Tyr Arg
                370                 375                 380 agc att ctg gat gcc tcc cta gag ctg ttc aag ttc acc att ggt atg          1200
Ser Ile Leu Asp Ala Ser Leu Glu Leu Phe Lys Phe Thr Ile Gly Met
385                     390                 395                 400 ggg gag ctg gct ttc cag gaa cag ctg cgt ttt cgt ggg gtg gtc ctg          1248
Gly Glu Leu Ala Phe Gln Glu Gln Leu Arg Phe Arg Gly Val Val Leu
                        405                 410                 415 ctg ttg ctg ttg gcc tac gtc ctt ctc acc tac gtc ctg ctc aac            1296
Leu Leu Leu Leu Ala Tyr Val Leu Leu Thr Tyr Val Leu Leu Leu Asn
                        420                 425                 430 atg ctc att gct ctc atg agc gaa act gtc aac cac gtt gct gac aac          1344
Met Leu Ile Ala Leu Met Ser Glu Thr Val Asn His Val Ala Asp Asn
                        435                 440                 445 agc tgg agc atc tgg aag ttg cag aaa gcc atc tct gtc ttg gag atg          1392
Ser Trp Ser Ile Trp Lys Leu Gln Lys Ala Ile Ser Val Leu Glu Met
        450                 455                 460 gag aat ggt tac tgg tgg tgc cgg agg aag aaa cat cgt gaa ggg agg          1440
Glu Asn Gly Tyr Trp Trp Cys Arg Arg Lys Lys His Arg Glu Gly Arg
465                     470                 475                 480 ctg ctg aaa gtc ggc acc agg ggg gat ggt acc cct gat gag cgc tgg          1488
Leu Leu Lys Val Gly Thr Arg Gly Asp Gly Thr Pro Asp Glu Arg Trp
                        485                 490                 495 tgc ttc agg gtg gag gaa gta aat tgg gct gct tgg gag aag act ctt          1536
Cys Phe Arg Val Glu Glu Val Asn Trp Ala Ala Trp Glu Lys Thr Leu
                        500                 505                 510 ccc acc tta tct gag gat cca tca ggg cca ggc atc act ggt aat aaa          1584
Pro Thr Leu Ser Glu Asp Pro Ser Gly Pro Gly Ile Thr Gly Asn Lys
                        515                 520                 525 aag aac cca acc tct aaa ccg ggg aag aac agt gcc tca gag gaa gac          1632
Lys Asn Pro Thr Ser Lys Pro Gly Lys Asn Ser Ala Ser Glu Glu Asp
                        530                 535                 540 cat ctg ccc ctt cag gtc ctc cag tcc ccc                                   1662
His Leu Pro Leu Gln Val Leu Gln Ser Pro
```

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: synthetic peptide

<400> SEQUENCE: 13

Ala Phe His Cys Lys Ser Pro His Arg His Arg Met Val Val Leu Glu
 1               5                  10                  15

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: synthetic peptide

<400> SEQUENCE: 14

Arg Pro Glu Ala Pro Thr Gly Pro Asn Ala Thr Glu Ser Val Gln Pro
 1               5                  10                  15

Met Glu Gly Gln Glu Asp Glu Gly Asn
            20                  25

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: synthetic peptide

<400> SEQUENCE: 15

Ser Val Leu Glu Met Glu Asn Gly Tyr Trp Trp Cys Arg Lys Lys Gln
 1               5                  10                  15

Arg Ala Gly

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
taggagaccc cgttgccacg                                              20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 17
gattcacttg gggacagtga cg                                           22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 18
ttaagctccc gttctccacc g                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 19
gctgcgggag gaagtgaagc                                                20

<210> SEQ ID NO 20
<211> LENGTH: 630
<212> TYPE: PRT
<213> ORGANISM: Homo sapiens

<400> SEQUENCE: 20

```
Met Thr Ser Pro Ser Ser Pro Val Phe Arg Leu Glu Thr Leu Asp
 1               5                  10                  15

Gly Gly Gln Glu Asp Gly Ser Glu Ala Asp Arg Gly Lys Leu Asp Phe
            20                  25                  30

Gly Ser Gly Leu Pro Pro Met Glu Ser Gln Phe Gln Gly Glu Asp Arg
        35                  40                  45

Lys Phe Ala Pro Gln Ile Arg Val Asn Leu Asn Tyr Arg Lys Gly Thr
    50                  55                  60

Gly Ala Ser Gln Pro Asp Pro Asn Arg Phe Asp Arg Asp Arg Leu Phe
65                  70                  75                  80

Asn Ala Val Ser Arg Gly Val Pro Glu Asp Leu Ala Gly Leu Pro Glu
                85                  90                  95

Tyr Leu Ser Lys Thr Ser Lys Tyr Leu Thr Asp Ser Glu Tyr Thr Glu
            100                 105                 110

Gly Ser Thr Gly Lys Thr Cys Leu Met Lys Ala Val Leu Asn Leu Lys
        115                 120                 125

Asp Gly Val Asn Ala Cys Ile Leu Pro Leu Leu Gln Ile Asp Arg Asp
    130                 135                 140

Ser Gly Asn Pro Gln Pro Leu Val Asn Ala Gln Cys Thr Asp Asp Tyr
145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Arg
            180                 185                 190

Ala Cys Gly Arg Phe Phe Gln Lys Gly Gln Gly Thr Cys Phe Tyr Phe
        195                 200                 205

Gly Glu Leu Pro Leu Ser Leu Ala Ala Cys Thr Lys Gln Trp Asp Val
    210                 215                 220

Val Ser Tyr Leu Leu Glu Asn Pro His Gln Pro Ala Ser Leu Gln Ala
225                 230                 235                 240

Thr Asp Ser Gln Gly Asn Thr Val Leu His Ala Leu Val Met Ile Ser
                245                 250                 255

Asp Asn Ser Ala Glu Asn Ile Ala Leu Val Thr Ser Met Tyr Asp Gly
            260                 265                 270

Leu Leu Gln Ala Gly Ala Arg Leu Cys Pro Thr Val Gln Leu Glu Asp
        275                 280                 285

Ile Arg Asn Leu Gln Asp Leu Thr Pro Leu Lys Leu Ala Ala Lys Glu
```

```
                    290                 295                 300
Gly Lys Ile Glu Ile Phe Arg His Ile Leu Gln Arg Glu Phe Ser Gly
305                 310                 315                 320

Leu Ser His Leu Ser Arg Lys Phe Thr Glu Trp Cys Tyr Gly Pro Val
                    325                 330                 335

Arg Val Ser Leu Tyr Asp Leu Ala Ser Val Asp Ser Cys Glu Glu Asn
                    340                 345                 350

Ser Val Leu Glu Ile Ile Ala Phe His Cys Lys Ser Pro His Arg His
                    355                 360                 365

Arg Met Val Val Leu Glu Pro Leu Asn Lys Leu Leu Gln Ala Lys Trp
            370                 375                 380

Asp Leu Leu Ile Pro Lys Phe Phe Leu Asn Phe Leu Cys Asn Leu Ile
385                 390                 395                 400

Tyr Met Phe Ile Phe Thr Ala Val Ala Tyr His Gln Pro Thr Leu Lys
                405                     410                 415

Lys Gln Ala Ala Pro His Leu Lys Ala Glu Val Gly Asn Ser Met Leu
                420                 425                 430

Leu Thr Gly His Ile Leu Ile Leu Leu Gly Gly Ile Tyr Leu Leu Val
                435                 440                 445

Gly Gln Leu Trp Tyr Phe Trp Arg Arg His Val Phe Ile Trp Ile Ser
    450                 455                 460

Phe Ile Asp Ser Tyr Phe Glu Ile Leu Phe Leu Phe Gln Ala Leu Leu
465                 470                 475                 480

Thr Val Val Ser Gln Val Leu Cys Phe Leu Ala Ile Glu Trp Tyr Leu
                485                 490                 495

Pro Leu Leu Val Ser Ala Leu Val Leu Gly Trp Leu Asn Leu Leu Tyr
                500                 505                 510

Tyr Thr Arg Gly Phe Gln His Thr Gly Ile Tyr Ser Val Met Ile Gln
        515                 520                 525

Lys Lys Ala Ile Ser Val Leu Glu Met Glu Asn Gly Tyr Trp Trp Cys
530                 535                 540

Arg Lys Lys Gln Arg Ala Gly Val Met Leu Thr Val Gly Thr Lys Pro
545                 550                 555                 560

Asp Gly Ser Pro Asp Glu Arg Trp Cys Phe Arg Val Glu Glu Val Asn
                565                 570                 575

Trp Ala Ser Trp Glu Gln Thr Leu Pro Thr Leu Cys Glu Asp Pro Ser
                580                 585                 590

Gly Ala Gly Val Pro Arg Thr Leu Glu Asn Pro Val Leu Ala Ser Pro
                595                 600                 605

Pro Lys Glu Asp Glu Asp Gly Ala Ser Glu Glu Asn Tyr Val Pro Val
    610                 615                 620

Gln Leu Leu Gln Ser Asn
625                 630
```